US007928060B2

(12) United States Patent
Erickson et al.

(10) Patent No.: US 7,928,060 B2
(45) Date of Patent: Apr. 19, 2011

(54) AMYLIN FAMILY POLYPEPTIDE-6 (AFP-6) ANALOGS AND METHODS OF MAKING AND USING THEM

(75) Inventors: Mary Erickson, San Diego, CA (US); Ved Srivastava, San Diego, CA (US); Sarah McQuaid, San Diego, CA (US); Andrew Young, Rancho Santa Fe, CA (US); Richard Pittner, San Diego, CA (US); Soumitra Ghosh, San Diego, CA (US)

(73) Assignee: Amylin Pharmaceuticals, Inc., San Diego, CA (US)

( * ) Notice: Subject to any disclaimer, the term of this patent is extended or adjusted under 35 U.S.C. 154(b) by 611 days.

(21) Appl. No.: 11/664,750

(22) PCT Filed: Oct. 11, 2005

(86) PCT No.: PCT/US2005/036456
§ 371 (c)(1),
(2), (4) Date: Mar. 12, 2008

(87) PCT Pub. No.: WO2006/042242
PCT Pub. Date: Apr. 20, 2006

(65) Prior Publication Data
US 2008/0207501 A1  Aug. 28, 2008

Related U.S. Application Data

(60) Provisional application No. 60/617,468, filed on Oct. 8, 2004.

(51) Int. Cl.
*A61K 38/22* (2006.01)
*C07K 14/575* (2006.01)

(52) U.S. Cl. .......... 514/5.3; 514/6.7; 514/6.9; 514/21.3; 530/324

(58) Field of Classification Search ........................ None
See application file for complete search history.

(56) References Cited

U.S. PATENT DOCUMENTS

| | | | |
|---|---|---|---|
| 5,264,372 | A | 11/1993 | Beaumont et al. |
| 5,686,511 | A | 11/1997 | Bobo |
| 5,849,883 | A | 12/1998 | Boone et al. |
| 5,998,367 | A | 12/1999 | Gaeta et al. |
| 6,630,169 | B1 | 10/2003 | Bot et al. |
| 6,965,013 | B2 | 11/2005 | Hsu |

(Continued)

FOREIGN PATENT DOCUMENTS

WO    WO8304053 A1    11/1983

(Continued)

OTHER PUBLICATIONS

Becker, et al, "Procalcitonin and the Calcitonin Gene Family of Peptides in Inflammation, Infection and Sepsis: A Journey from Calcitonin Back to Its Precursors," Journal of Clinical Endocrinology & Metabolism (2004) 89 (4) 1512-1525.

(Continued)

*Primary Examiner* — Jeffrey E Russel

(57) ABSTRACT

The present invention relates to Amylin Family Polypeptide-6 (AFP-6) analogs, which include derivatives and fragments, related nucleic acids, expression constructs, host cells, and processes for recombinant production of the AFP-6 analogs. The AFP-6 analogs of the invention include one or more amino acid sequence modifications. In addition, methods and compositions are disclosed to treat and prevent conditions such as metabolic and cardiovascular disorders, e.g., obesity, diabetes, metabolic syndrome, myocardial ischemia, and increased cardiovascular risk.

16 Claims, 12 Drawing Sheets

Food Intake Assay: cumulative food intake

• $p<0.05$ vs. vehicle control; ANOVA, Dunnett's test

U.S. PATENT DOCUMENTS

| | | |
|---|---|---|
| 2004/0170568 A1 | 9/2004 | Weers et al. |
| 2005/0197287 A1 | 9/2005 | Mack et al. |
| 2006/0063716 A1 | 3/2006 | Hsu |
| 2006/0094652 A1 | 5/2006 | Levy et al. |
| 2006/0094653 A1 | 5/2006 | Levy et al. |

FOREIGN PATENT DOCUMENTS

| | | |
|---|---|---|
| WO | WO9907404 A1 | 2/1999 |
| WO | WO9925727 A2 | 5/1999 |
| WO | WO9925728 A1 | 5/1999 |
| WO | WO03026591 A2 | 4/2003 |
| WO | WO03057235 A2 | 7/2003 |
| WO | WO2004048547 A2 | 6/2004 |

OTHER PUBLICATIONS

Beltowski, et al, Adrenomedullin—What Do We Know 10 Years Since Its Discovery? Polish Journal of Pharmacology (2004) 56:5-27.

Campfield, et al, "Recombinant Mouse OB Protein: Evidence for a Peripheral Signal Linking Adiposity and Central Neural Networks" Science (1995) 269:546-549.

Chang, et al, "Intermedin, A Novel Calcitonin Family Peptide That Exists In Teleosts as Well as in Mammals: A Comparison With Other Calcitonin/INtermedin Family Peptides in Vertebrates," Peptides (2004) 25(10):1633-1642.

D'Santos, et al, "Stimulation of Adenylate Cyclase by Amylin in CHO-K1 Cells," Mol. Pharmacol. (1992) 41 (5):894-899.

Dumont, et al, "Receptor Autoradiography as Mean to Explore the Possible Functional Relevance of Neuropeptides: Focus on New Agonists and Antagonists to Study Natriuretic Peptides, Neuropeptide Y and Calcitonin Gene-Related Peptides," (2004) 25:365-391.

Halaas, et al, "Weight-Reducing Effects of the Plasma Protein Encoded by the Obese Gene," Science (1995) 269 (5223):543-546.

Hinson, et al, "Andrenomedullin, a Multifunctional Regulatory Peptide," Endocrin Reviews 21(2):138-167, (2000).

Kato, et al, "Receptors for adrenomedullin in human vascular endothelial cells," Eur J Pharmacol. (1995) 289:383-385.

Kozak M., "At least six nucleotides preceding the AUG initiator codon enhance translation in mammalian cells," J Mol Biol. Aug. 20, 1987;196(4):947-950.

Kozak M., "An analysis of 5'-noncoding sequences from 699 vertebrate messenger RNAs," Nucleic Acids Res. Oct. 26, 1987;15(20):8125-8148.

Kuestner, et al, "Cloning and characterization of an abundant subtype of the human calcitonin receptor," Mol Pharmacol (1994) 46: 246-255.

Kurihara, et al, "Targeted Disruption of Adrenomedullin and αCGRP Genes Reveals Their Distinct Biological Roles," Hypertens. Res. (2003) 26 Suppl:S 105-108.

Muff, et al, "Comparison of a Calcitonin Gene-Related Peptide Receptor in a Human Neuroblastoma Cell Line (SK-N-MC) and a Calcitonin Receptor in a Human Breast Carcinoma Cell Line (T47D)α," Annals New York Academy of Science (1992) 657:106-116.

Nagaya, et al, "Repeated inhalation of adrenomedullin ameliorates pulmonary hypertension and survival in monocrotaline rats," Am J Physiol Heart Circ Physiol (2003) 285: H2125-H2131.

Nicholls, et al, "Bioactivity of adrenomedullin and proadrenomedullin N-terminal 20 peptide in man" Peptides (2001) 22:1745-1752.

Ogoshi, M., et al, "Identification of a Novel Adrenomedullin Gene Family in Teleost Fish," Biochemical and Biophysical Research Communications (2003) 311(4):1072-1077.

Pelleymounter, et al, "Effects of the Obese Gene Product on Body Weight Regulation in Ob/Ob Mice," Science (1995) 269(5223):540-543.

Roh, et al, "Intermedin Is a Calcitonin/Calcitonin Gene-related Peptide Family Peptide Acting Throught the Calcitonin Receptor-like Receptor/Receptor Activity-modifying Protein Receptor Complexes," J. Biol. Chem. (2004) 279(8):7264-7274.

Sandberg, et al, "New Chemical Descriptors Relevant for the Design of Biologically Active Peptides, A Multivariate characterization of 87 Amino Acids," J. Med. Chem. (1998) 41:2481-2491.

Sexton, et al, "Calcitonin," Current Medicinal Chemistry (1999) 6:1067-1093.

Takei, et al. "Identification of Novel Adrenomedullin in Mammals: A Potent Cardiovascular and Renal Regulator," FEBS Letters (2004) 556(1):53-58.

Taylor, et al, "Adrenomedullin Inhibits Feeding in the Rat by a Mechanism Involving Calcitonin Gene-related Peptide Receptors," Endocrinology (1996) 137: 3260-3264.

Wimalawansa, S. J., "Amylin, Calcitonin Gene-Related Peptide, Calcitonin, and Adrenomedullin: a Peptide Superfamily," Critical Reviews in Neurobiology (1997) 11(2&3):167-239.

Figure 1A

>gi|20903165|ref|XPM_147916) hypothetical protein XP_147916 [Mus musculus] Length = 150

Score = 32.3 bits (72), Expect = 0.23, Identities = 24/74 (32%), Positives = 33/74 (44%), Gaps = 11/74 (14%)

```
Query:  75  GASRSPEDSSPDAARIRVKRYRQSMNNFQGLRSFGCRFGTCTVQKLAHQIYQFT-DKDKD  133
            G SR P    P  +R  + + Q      L   GC  GTC VQ L+H+++Q      +
Sbjct:  87  GGSRHPGPQRPTGSR---RPHAQ------LLRVGCVLGTCQVQNLSHRLWQLVRPAGRR  136

Query: 134  NVAPRSKISPQGYG  147
            + AP    SP  YG
Sbjct: 137  DSAPVDPSSPHSYG  150
```

Figure 1B

```
hAdm P35318    1    MKLVSVALMYLGSLAFLGADTARLDVASEFRKKWNKWALSRGKRELRMSSSYPTGLADVK
XP_147916      1    MAQLLMVTVTLGCISLLYLLPGTLSGSLGKGLRHSRPREPPAKIPSSNLQPGHPSLQPWV hAdm P35318   61    AGPAQTLIRPQDMKGASRSPEDSSPDAARIR..VKRYRQSMNNFQGLRSFGCRFGTCTVQ
XP_147916     61    WKSRRHAPQPQGRGNRALAMVHLPQGGGSRHPGPQRPTGSRRPHAQLLRVGCVLGTCQVQ hAdm P35318  119    KLAHQIYQFT.DKDKDNVAPRSKISPQGYGRRRRRSLPEAGPGRTLVSSKPQAHGAPAPP
XP_147916    121    NLSHRLWQLVRPAGRRDSAPVDPSSPHSYG...............................

hAdm P35318  178    SGSAPHFL
XP_147916           ........
```

Figure 2

>gi|20903165|ref|XP_147916.11 hypothetical protein XP_147916 [Mus musculus]

MAQLLMVTVTLGCISLLYLLPGTLSGSLGKGLRHSRPREPPAKIPSSNLQPGHPSLQPWWKSRRHAPQP
QGRGNRALAMVHLPQGGGSRHPGPQRPTGSRRPHAQLLRVGCVLGTCQVQNLSHRLWQLVRPAGRRDS
APVDPSSPHSYG

Figure 3

```
Mouse AFP-6        1  MAQLLMVTVTLGCTSLLYL.LPGTLSGSLGKGLRHSRPREPPAKIPSSNLQPGHPSLQPV
Human AFP-6 long   1  ..MARIPTAALGCISLLCLQLPGSLSRSLGGDPRPVKPREPPARSPSSSLQPRHPAPRPV
Human AFP-6 short  1  ..MARIPTAALGCISLLCLQLPGSLSRSLGGDPRPVKPREPPARSPSSSLQPRHPAPRPV Mouse AFP-6       60  VWKSRRHAPQPQGRGNRALAMVHLPQGGGSRHPGPQRPTGSRRPHAQLLRVGCVLGTCQV
Human AFP-6 long  59  VWKLHRALQAQRGAG.LAPVMGQPLRDGGRQHSGPRRHGPRRTQAQLLRVGCVLGTCQV
Human AFP-6 short 59  VWKLHRALQAQRGAG.LAPVMGQPLRDGGRQHSGP......RRTQAQLLRVGCVLGTCQV Mouse AFP-6      120  QNLSHRLWQLVRPAGRRDSAPVDPSSPHSYG
Human AFP-6 long 118  QNLSHRLWQLMGPAGRQDSAPVDPSSPHSYG
Human AFP-6 short 112 QNLSHRLWQLMGPAGRQDSAPVDPSSPHSYG
```

Figure 4

```
hAdm P35318       1  .MKLVSVALMYLGSLAFLGADTARLDVASEFRKKWNKWALSRGKRELRMSSSYPTGLADV
Human AFP-6 short 1  MARIPTAALGCISLLCLQLPGSLSRSLGGDPRPVKPREPPARSP.....SSSLQPRHPAP hAdm P35318      60  KAGPAQTLIRPQDMKGASRSPEDSSPDAARIRVKRYRQSMNNFQGLRSFGCRFGTCTVQK
Human AFP-6 short 56 RPVVWKLHRALQAQRGAGLAP..VMGQPLRDGGRQHSGPRRTQAQLLRVGCVLGTCQVQN hAdm P35318     120  LAHQIYQFT.DKDKDNVAPRSKISPQGYGRRRRRSLPEAGPGRTLVSSKPQAHGAPAPPS
Human AFP-6 short 114 LSHRLWQLMGPAGRQDSAPVDPSSPHSYG...............................

hAdm P35318     179  GSAPHFL
Human AFP-6 short    .......
```

Figure 5

```
hs_AFP6          1  ......TQAQLLRVGC.VLGTCQVQNLSHRLWQLMGPAGRQDSAPVDPSSPHSYG
hs_adrenomedullin 1 YRQSMNNFQGLRSFGC.RFGTCTVQKLAHQIYQFT.DKDKDNVAPRSKISPQGYG
hs_Amylin        1  .............KC.NTATCATQRLANFLVHSSN.NFGAILSSTN.VGSNTYG
hs_CGRP1         1  .............AC.DTATCVTHRLAGLLSRSG.GVVKNNFVPTN.VGSKAFG
hs_Calcitonin    1  .............CGNLSTCM...LGTYTQDFN....KFHTFPQTAIGVGAPG
```

Figure 6

Human
TQAQLLRVGCVLGTCQVQNLSHRLWQLMGPAGRQDSAPVDPSSPHSY-NH2    (SEQ ID NO:1)

VGCVLGTCQVQNLSHRLWQLMGPAGRQDSAPVDPSSPHSY-NH2    (SEQ ID NO:2)

Mouse
PHAQLLRVGCVLGTCQVQNLSHRLWQLVRPAGRRDSAPVDPSSPHSY-NH2    (SEQ ID NO:3)

VGCVLGTCQVQNLSHRLWQLVRPAGRRDSAPVDPSSPHSY-NH2    (SEQ ID NO:4)

Figure 7

```
AFP-6_5'200bp     1  ..............................................................
NM_024866         1  ATTCAGCCCTGGAGGTGCCATCCCGGGCCGCGACTCCGCTCCAGGCAGGACCCCCAACCC

AFP-6_5'200bp     1  ..............................................................
NM_024866        61  GCCCAGCCCGCTCCGCCTTGCGCCCCGGACCCGCGGCCGACCCCAGACCCGCTGCCCGCT

AFP-6_5'200bp     1  ........................GACGGACGCCCGTGCCCAGCTTGCCACGCCCACGCCCG
NM_024866       121  TCGCGCCCGAGGCCTGCGCCCCGACGGACGCCCGTGCCCAGCTTGCCACGCCCACGCCCG

AFP-6_5'200bp    39  GCGCCCCGACCGCGGAGGACTCCCCGAG..................................
NM_024866       181  GCGCCCCGACCGCGGAGGACTCCCCGAGGTGCCGGCGGAGGGGGTGGCTCGCGGCTCAGG

AFP-6_5'200bp    67  ................................CCCCGCCCGCCATGGCCCG
NM_024866       241  CTGCCCCCGACGTGCCCGGCTCACCGCCCCCTCCCCTGCAGCCCCGCCCGCCATGGCCCG

AFP-6_5'200bp    86  GATCCCGACGGCCGCCCTGGGTTGCATCAGCCTCCTCTGCCTGCAGCTCCCTGGCTCGCT
NM_024866       301  GATCCCGACGGCCGCCCTGGGTTGCATCAGCCTCCTCTGCCTGCAGCTCCCTGGCTCGCT

AFP-6_5'200bp   146  GTCCCGCAGCCTGGGCGGGGACCCGCGACCCGTCAAACCCAGGGAGCCCCCAGCCCG...
NM_024866       361  GTCCCGCAGCCTGGGCGGGGACCCGCGACCCGTCAAACCCAGGGAGCCCCCAGCCCGGAG

AFP-6_5'200bp        ..............................................................
NM_024866       421  CCCTTCCAGCAGCCTGCAGCCCAGGCACCCCGCACCCCGACCTGTGGTCTGGAAGCTTCA
```

• p<0.05 vs. vehicle control; ANOVA, Dunnett's test

• p<0.05 vs. vehicle control; ANOVA, Dunnett's test $p<0.05$ vs. vehicle control; ANOVA, Dunnett's test $p < 0.05$ vs. vehicle control; ANOVA, Dunnett's test

*P<0.05 compared to Vehicle group

AMYLIN FAMILY POLYPEPTIDE-6 (AFP-6) ANALOGS AND METHODS OF MAKING AND USING THEM

CROSS-REFERENCE TO RELATED APPLICATION

This application is a national stage filing of International Application No. PCT/US2005/036456, filed 11 Oct. 2005, which claims the benefit of priority under 35 U.S.C. §119(e) of U.S. provisional patent application No. 60/617,468, filed 8 Oct. 2004, which are herein incorporated by reference in their entirety.

FIELD OF THE INVENTION

The present invention relates to novel compounds having an activity of a member of the Amylin Family of polypeptides. These compounds are useful for treating or preventing conditions such as metabolic disorders, vascular disorders, renal disorders, and/or gastrointestinal disorders. An exemplary condition is one in which the reduction of caloric intake is of value, e.g., obesity, Type II diabetes, eating disorders, metabolic syndrome and insulin-resistance syndrome.

BACKGROUND OF THE INVENTION

Amylin Family Polypeptide-6 (AFP-6) is a member of the Amylin Family, which includes amylin, adrenomedullin (ADM), calcitonin (CT), and calcitonin gene related peptide (CGRP). The human AFP-6 gene, also known as intermedin, encodes a 148 amino acid open reading frame with a 24 amino acid signal peptide for secretion at the N-terminus and a mature amidated peptide having an amino acid sequence of (SEQ ID NO: 1)
TQAQLLRVGCVLGTCQVQNLSHRLWQLMGPAGRQDSAPVDPSSPHSY-
NH2.

Other AFP-6 polypeptides include:

(SEQ ID NO: 2)
VGCVLGTCQVQNLSHRLWQLMGPAGRQDSAPVDPSSPHSY-NH2;

(SEQ ID NO: 3)
PHAQLLRVGCVLGTCQVQNLSHRLWQLVRPAGRRDSAPVDPSSPHSY-
NH2;
and (SEQ ID NO: 4)
VGCVLGTCQVQNLSHRLWQLVRPAGRRDSAPVDPSSPHSY-NH2.

Still other Amylin Family polypeptides include:

(SEQ ID NO: 5)
KCNTATCATQRLANFLVHSSNNFGAILSSTNVGSNTY-NH2;

(SEQ ID NO: 6)
CGNLSTCMLGTYTQDFNKFHTFPQTAIGVGAP-NH2;

(SEQ ID NO: 7)
ACDTATCVTHRLAGLLSRSGGWKNNFVPTNVGSKAF-NH2;

(SEQ ID NO: 8)
ACNTATCVTHRLAGLLSRSGGMVKSNFVPTNVGSKAF-NH2;

(SEQ ID NO: 9)
YRQSMNNFQGLRSFGCRFGTCTVQKLAHQIYQFTDKDKDNVAPRSKISPQ
GY-NH2.

Table 1 shows the polypeptide corresponding to the SEQ ID NOs. shown above. SEQ ID NOs: 1-4 relate to forms of human and mouse AFP-6. SEQ ID NOs: 5-9 relate to human Amylin Family polypeptides of amylin, calcitonin, CGRP α, CGRP β, and adrenomedullin.

TABLE 1

| | |
|---|---|
| SEQ ID NO: 1 | Human AFP-6 [1-47] |
| SEQ ID NO: 2 | Human AFP-6 [8-47] |
| SEQ ID NO: 3 | Mouse AFP-6 [1-47] |
| SEQ ID NO: 4 | Mouse AFP-6 [8-47] |
| SEQ ID NO: 5 | Human Amylin |
| SEQ ID NO: 6 | Human Calcitonin |
| SEQ ID NO: 7 | Human CGRP α |
| SEQ ID NO: 8 | Human CGRP β |
| SEQ ID NO: 9 | Human Adrenomedullin |

It has been reported that the biological actions of these Amylin Family polypeptides are mediated via binding to two closely related type II G protein-coupled receptors (GPCRs), the calcitonin receptor (CTR) and the calcitonin receptor like receptor (CRLR). Cloning and functional studies have shown that CGRP, ADM, and amylin interact with different combinations of CTR or the CRLR and the receptor activity modifying protein (RAMP). Many cells express multiple RAMPs. It is believed that co-expression of RAMPs and either the CTR or CRLR is required to generate functional receptors for calcitonin, CGRP, ADM, and amylin. The RAMP family comprises three members (RAMP1, -2, and -3), which share less then 30% sequence identity, but have a common topological organization. Co-expression of CRLR and RAMP 1 leads to the formation of a receptor for CGRP. Co-expression of CRLR and RAMP2 leads to the formation of a receptor for ADM. Co-expression of CRLR and RAMP3 leads to the formation of a receptor for ADM and CGRP. Co-expression of hCTR2 and RAMP1 leads to the formation of a receptor for amylin and CGRP. Co-expression of hCTR2 and RAMP3 leads to the formation of a receptor for amylin.

Amylin regulates gastric emptying and suppresses glucagon secretion and food intake, thus regulating the rate of glucose appearance in the circulation. It appears to complement the actions of insulin, which regulates the rate of glucose disappearance from the circulation and its uptake by peripheral tissues. These actions are supported by experimental findings in rodents and humans, which indicate that amylin complements the effects of insulin in postprandial glucose control by at least three independent mechanisms, all of which affect the rate of glucose appearance. First, amylin suppresses postprandial glucagon secretion. Compared to healthy adults, patients with type 1 diabetes have no circulating amylin and patients with type 2 diabetes have diminished postprandial amylin concentrations. Furthermore, infusion of an amylin specific monoclonal antibody, which bound circulating amylin, again resulted in greatly elevated glucagon concentrations relative to controls. Both of these results point to a physiological role of endogenous amylin in the regulation of postprandial glucagon secretion. Second, amylin slows gastrointestinal motility and gastric emptying. Finally, intra-hypothalamic injections of rat amylin were shown to reduce feeding in rats and alter neurotransmitter metabolism in the hypothalamus. In certain studies, food intake was significantly reduced for up to eight hours following the intrahypothalamic injection of rat amylin and rat CGRP. In human trials, an amylin analog, pramlintide, has been shown to reduce weight or weight gain. Amylin may be beneficial in treating metabolic conditions such as diabetes and obesity. Amylin may also be used to treat pain, bone disorders, gastritis, to modulate lipids, in particular triglycerides, or to affect body composition such as the preferential loss of fat and sparing of lean tissue.

The hormone calcitonin (CT) was named for its secretion in response to induced hypercalcemia and its rapid hypocalcemic effect. It is produced in and secreted from neuroendocrine cells in the thyroid that have since been termed C cells. The best-studied action of CT(1-32) is its effect on the osteoclast. In vitro effects of CT include the rapid loss of ruffled borders and decreased release of lysosomal enzymes. Ultimately, the inhibition of osteoclast functions by CT results in a decrease in bone resorption. However, neither a chronic reduction of serum CT in the case of thyroidectomy nor the increased serum CT found in medullary thyroid cancer appears to be associated with changes in serum calcium or bone mass. It is thus most likely that a major function of CT(1-32) is to combat acute hypercalcemia in emergency situations and/or protect the skeleton during periods of "calcium stress" such as growth, pregnancy, and lactation. Reviewed, for example, in Becker (2004) *JCEM* 89(4):1512-1525 and Sexton (1999) *Current Medicinal Chemistry* 6:1067-1093. Consistent with this is recent data from the calcitonin gene knockout mouse, which removes both the calcitonin and the CGRP-I peptides, that revealed that the mouse had normal levels of basal calcium-related values, but an increased calcemic response (Kurihara et al. (2003) *Hypertens Res.* 26 Suppl:S 105-108).

CT has an effect on plasma calcium levels and inhibits osteoclast function and is widely used for the treatment of osteoporosis. Therapeutically, salmon CT appears to increase bone density and decrease fracture rates with minimal adverse effects. CT has also been successfully used over the past 25 years as a therapy for Paget's disease of bone, which is a chronic skeletal disorder that may result in enlarged or deformed bones in one or more regions of the skeleton. CT is also widely used for its analgesic effect on bone pain experienced during osteoporosis, although the mechanism for this effect is not clearly understood.

Calcitonin gene related peptide (CGRP) is a neuropeptide whose receptors are widely distributed in the body, including the nervous system and the cardiovascular system. This peptide seems to modulate sensory neurotransmission and is one of the most potent endogenous vasodilatory peptides discovered to date. Reported biological effects for CGRP include: modulation of substance P in inflammation, nicotinic receptor activity at the neuromuscular junction, stimulation of pancreatic enzyme secretion, a reduction of gastric acid secretion, peripheral vasodilation, cardiac acceleration, neuromodulation, regulation of calcium metabolism, osteogenic stimulation, insulin secretion, an increase in body temperature and a decrease in food intake. Wimalawansa (1997) *Crit. Rev. Neurobiol.* 11(2-3):167-239. An important role of CGRP is to control blood flow to various organs by its potent vasodilatory actions, as evidenced by a decrease of mean arterial pressure following intravenous administration of α-CGRP. The vasodilatory actions are also supported by recent analysis of homozygous knockout CGRP mice, which demonstrated elevated peripheral vascular resistance and high blood pressure caused by increased peripheral sympathetic activity (Kurihara (2003), Supra). Thus, CGRP appears to elicit vasodilatory effects, hypotensive effects and an increase in heart rate among other actions.

Prolonged infusion of CGRP into patients with congestive cardiac failure has shown a sustained beneficial effect on hemodynamic functions without adverse effects, suggesting a use in heart failure. Other indications of CGRP use include renal failure, acute and chronic coronary artery ischemia, treatment of cardiac arrhythmia, other peripheral vascular disease such as Raynaud's phenomenon, subarachnoid hemorrhage, hypertension, and pulmonary hypertension. Preeclamptic toxemia of pregnancy and preterm labor is also potentially treatable. (Wimalawansa (1997) Supra). Recent therapeutic uses include the use of CGRP antagonists for the treatment of migraine headaches.

Adrenomedullin is almost ubiquitously expressed with many more tissues containing the peptide than not. A published review of ADM details its effects on the cardiovascular system, cellular growth, the central nervous system and the endocrine system, with a range of biological actions including vasodilation, cell growth, regulation of hormone secretion, and natriuresis (Hinson et al. (2000) *Endocrine Reviews* 21(2): 138-167). Studies in rats, cats, sheep, and man confirm that intravenous infusion of ADM results in potent and sustained hypotension that is comparable to that of CGRP. However, the hypotensive effect of ADM on mean arterial pressure in the anesthetized rat is not inhibited by the CGRP antagonist CGRP8-37 suggesting that this effect is not mediated via CGRP receptors. Acute or chronic administration of human ADM in rats, anesthetized, conscious or hypertensive, results in a significant decrease in total peripheral resistance accompanied by a fall in blood pressure, with a concomitant rise in heart rate, cardiac output and stroke volume.

ADM has also been proposed as an important factor in embryogenesis and differentiation and as an apoptosis survival factor for rat endothelial cells. This is supported by recent mouse ADM knockout studies, in which mice homozygous for loss of the ADM gene demonstrated defective vascular formation during embryogenesis and thus died midgestation. It was reported that ADM+/−heterozygous mice had high blood pressure along with susceptibility to tissue injury (Kurihara (2003), Supra.).

ADM affects such endocrine organs as the pituitary, the adrenal gland, reproductive organs and the pancreas. The peptide appears to have a role in inhibiting ACTH release from the pituitary. In the adrenal gland, it appears to affect the secretory activity of the adrenal cortex in both rat and human and it increases adrenal blood flow, acting as a vasodilator in the adrenal vascular bed in intact rats. ADM has been shown to be present throughout the female reproductive tract and plasma levels are elevated in normal pregnancy. Studies in a rat model of preeclampsia show that ADM can reverse hypertension and decrease pup mortality when given to rats during late gestation. Because it did not have a similar effect in animals in early gestation or nonpregnant rats in the preeclampsia model, this suggests that ADM may play an important regulatory role in the utero-placental cardiovascular system. In the pancreas, ADM most likely plays an inhibitory role since it attenuated and delayed insulin response to an oral glucose challenge, resulting in initial elevated glucose levels. ADM can also affect renal function. A bolus administered peripherally can significantly lower mean arterial pressure and raise renal blood flow, glomerular filtration rate and urine flow. In some cases, there is also an increase in Na+ excretion.

ADM also has other peripheral effects on bone and on the lung. For bone, studies have supported a role beyond the cardiovascular system and fluid homeostasis and have demonstrated that ADM acts on fetal and adult rodent osteoblasts to increase cell growth comparable to those of known osteoblast growth factors such as transforming growth factor-β. This is important clinically as one of the major challenges in osteoporosis research is to develop a therapy that increases bone mass via osteoblastic stimulation. In the lung, ADM not only causes pulmonary vasodilation, but also inhibits bronchoconstriction induced by histamine or acetylcholine.

Recent studies using aerosolized ADM to treat pulmonary hypertension in a rat model indicate that inhalation treatment of this condition is effective, as evidenced by the fact that mean pulmonary arterial pressure and total pulmonary resistance were markedly lower in rats treated with ADM than in those given saline. This result was achieved without an alteration in systemic arterial pressure or heart rate (Nagaya et al. (2003) *Am. J. Physiol. Heart Circ. Physiol.* 285:H2125-2131).

A review published by Nicholls et al. (*Peptides* (2001) 22:1745-1752) summarizes the effects of infusion of ADM. In healthy volunteers, i.v. infusion reduced arterial pressure and stimulated heart rate, cardiac output, plasma levels of cAMP, prolactin, norepinephrine and rennin. In these patients, there was little or no increase in urine volume or sodium excretion observed. In patients with heart failure or chronic renal failure, i.v. ADM had similar effects to those seen in normal subjects and also induced diuresis and natriuresis, depending on the dose administered. Experimental ADM treatment has also been shown to be beneficial in arterial and pulmonary hypertension, septic shock and ischemia/reperfusion injury (Beltowski (2004) *Pol. J Pharmacol.* 56:5-27). Other indications for ADM treatment include: peripheral vascular disease, subarachnoid hemorrhage, hypertension, preeclamptic toxemia of pregnancy and preterm labor, and osteoporosis.

As the newest member of the Amylin Family of peptides, the biological function of AFP-6 is less well characterized than the members discussed above. However, the expression data obtained from Northern blots of human and mouse tissue is shown in Table 4, in the Example section below, and is consistent with reported data indicating that expression is primarily in the pituitary and gastrointestinal tract. A specific receptor for AFP-6 has not been reported; however, binding studies indicate that AFP-6 binds to all the known receptors of the Amylin Family. AFP-6 has been shown to increase cAMP production in SK-N-MC and L6 cells expressing endogenous CGRP receptors and competes with labeled CGRP for binding to its receptors in these cells. In published in vivo studies, AFP-6 administration led to blood pressure reduction in both normal and spontaneously hypertensive rats, most likely via interactions with the CRLR/RAMP receptors. In vivo administration in mice led to a suppression of gastric emptying and food intake (Roh et al (2004) *J. Biol. Chem.* 279(8):7264-7274).

Studies using mutant mice deficient for a CGRP, ADM, or amylin have indicated that, in different systems, CRLR can be important for cardiovascular morphogenesis, sensory neurotransmission, inflammatory reactions, nociceptive behavior, and glucose homeostasis. Thus, the physiological functions of polypeptides in this family are determined by receptor-binding specificity and the tissue expression profiles of individual ligands. AFP-6 appears to be unique in that it binds to all the receptors of the Amylin Family. For example, while amylin binds to the amylin, calcitonin and CGRP receptors with 0.05 nM to 20 nM affinity, it does not bind with very high affinity to the adrenomedullin receptor (several hundred nM affinity). In bovine studies, AFP-6 was shown to bind the adrenomedullin receptor (around 1-5 nM) in addition to having between 3-30 mM binding at the other 3 receptors, giving it amylin, CT, CGRP and/or ADM properties. See also Table 3 herein for receptor binding data.

Amylin Family proteins in general, and AFP-6 polypeptides in particular, have a variety of biological activities that are of use in the treatment or prevention of a variety of diseases, conditions, and disorders. There remains a need to develop such polypeptides, as well as derivatives and analogs thereof, for use in treating and/or preventing the described diseases, conditions, and disorders.

SUMMARY OF THE INVENTION

In one general aspect, the invention is drawn to novel AFP-6 analogs. It has been discovered that certain regions of the AFP-6 polypeptide are desirable for binding and/or activity. In certain embodiments, novel AFP-6 analogs are compounds comprising an amino acid sequence of formula (I):

$X_1$-$X_2$-$X_3$-$X_4$-$X_5$-$X_6$-$X_7$-$X_8$-QVQNLSHRLWQL-$X_{21}$-$X_{22}$-$X_{23}$-$X_{24}$-$X_{25}$-$X_{26}$-$X_{27}$-$X_{28}$-SAPV-$X_{33}$-PSSPHSY (SEQ ID NO: 41) wherein $X_1$ is absent, TQAQLLRVG (SEQ ID NO: 42), any of one or more consecutive amino acids of SEQ ID NO:42, N-aryl, or N-acyl with a substituent selected from a C1-C18 alkyl, a substituted alkyl or a heteroaryl moiety;

$X_2$ is M, S, C, substituted L, K, D or E, where the side chain can be linked via an amide bond, or any amino acid that can form a bond with $X_8$, for example a disulfide or an amide bond;

$X_3$ is V, D, L, G, N, A, or S;

$X_4$ is V, D, L, G, N, A, S or T;

$X_5$ is V, D, L, G, N, A, or S;

$X_6$ is V, D, L, G, N, A, S, or absent;

$X_7$ is T, S, homoserine, (S)-2-Amino-3-hydroxy-3-methylbutanoic acid (Ab) or (2R,3R)-2-Amino-3-hydroxy-4-methylpentanoic acid (Ap);

$X_8$ is M, S, C, substituted L, K, D or E, or any amino acid that can form a bond with $X_2$, for example a disulfide or an amide bond;

$X_{21}$ is M, G, P, A, or absent;
$X_{22}$ is M, G, P, A, or absent;
$X_{23}$ is M, G, P, A, or absent;
$X_{24}$ is M, G, P, A, or absent;
$X_{25}$ is M, G, P, A, or absent;
$X_{26}$ is R or absent, wherein when $X_{26}$ is absent, $X_{27}$ is absent;
$X_{27}$ is Q or absent, wherein when $X_{27}$ is absent, $X_{26}$ is absent;
$X_{28}$ is D or E;
$X_{33}$ is D or E; and
biologically active fragments thereof; however, it is contemplated that the AFP-6 analog of this genus does not include SEQ ID NOs: 1 or 2.

In other embodiments, novel AFP-6 analogs comprise, or the active region consists of, an amino acid sequence of formula (II):

$X_1$-$X_2$-QNLSHRLWQL-$X_{13}$-$X_{14}$-$X_{15}$-$X_{16}$-$X_{17}$-$X_{18}$-$X_{19}$-$X_{20}$-SAPV-$X_{25}$-PSSPHSY (SEQ ID NO: 56) wherein $X_1$ is Q or absent;
$X_2$ is V or absent;
$X_{13}$ is M, G, P, A, or absent;
$X_{14}$ is M, G, P, A, or absent
$X_{15}$ is M, G, P, A, or absent;
$X_{16}$ is M, G, P, A, or absent;
$X_{17}$ is M, G, P, A, or absent,
$X_{18}$ is R or absent, wherein when $X_{18}$ is absent, $X_{19}$ is absent;
$X_{19}$ is Q or absent, wherein when $X_{19}$ is absent, $X_{18}$ is absent
$X_{20}$ is D or E;
$X_{25}$ is D or E; and
biologically active fragments thereof, wherein the amino acid sequence is not SEQ ID NOs: 13 or 14.

In still other embodiments, AFP-6 analogs comprise the amino acid sequence of SEQ ID NO: 10-12, 16-33 and 35-40.

In yet other embodiments, AFP-6 analogs comprise or the active region consists of the amino acid sequence of SEQ ID NOs: 15 or 34.

In certain embodiments, AFP-6 analogs may be characterized by having no more than 25, 30, 35, 40, or 45 amino acids. In other embodiments, AFP-6 analogs may have 23 to 49 amino acids. In certain embodiments, AFP-6 analogs comprise at least 80, 82, 84, 86, 88, 90, 92, 94, 96, 97, or 98% amino acid sequence identity to SEQ ID NOs: 1-4 and 10-12, 16-33 and 35-40 and having at least one Amylin Family activity, wherein the compound is not SEQ ID NOs:1-4. In other embodiments, AFP-6 analogs comprise, or the active region consists of, at least 80, 82, 84, 86, 88, 90, 92, 94, 96, 97, or 98% amino acid sequence identity to the sequence of SEQ ID NOs:15 and 34 and having an antagonist activity to an Amylin Family polypeptide, wherein the compound is not SEQ ID NOs:13 or 14.

In another general aspect, the invention provides methods of using AFP-6, AFP-6 agonists or AFP-6 analogs. In certain embodiments, the invention contemplates methods of treating or preventing a condition or disease that can be alleviated by reducing caloric or nutrient intake or availability in a subject. Methods of the invention can include, but are not limited to, conditions and diseases of obesity, insulin resistance, metabolic syndrome and diabetes mellitus. In other embodiments, the invention contemplates methods of treating or preventing a cardiovascular condition or disease in a subject. Non-limiting examples of a cardiovascular condition or disease are hypertension, myocardial ischemia, and myocardial reperfusion.

In yet other embodiments, the methods of the invention contemplate use of AFP-6 analogs having antagonist activity. Thus, exemplary uses include treating or preventing anorexia, cachexia, bulimia, and other wasting diseases characterized by loss of appetite, diminished food intake, body weight loss, gastric hypomotility, or hypotension in a subject.

Additional embodiments include administration of the compounds at a dose in the range of from about 0.05 mg/kg to about 2 mg/kg, exemplary modes of delivery such as injection, infusion, absorption (e.g., mucosal, transmucosal, transdermal), and inhalation, nucleotides that encode the amino acid sequence herein described, vectors containing the nucleotides, host cells for propagating nucleotides and/or expressing the polypeptides encoded by the nucleotides, antibodies directed to the AFP-6, AFP-6 agonists and AFP-6 analogs, and their uses in screening or detection/diagnosis in a subject. In another embodiment, the invention provides methods for preparing AFP-6 analogs, including methods comprising culturing host cells containing an expression vector encoding an AFP-6 analog under conditions that provide for expression of the AFP-6 analog and isolating the expressed AFP-6 analog.

All documents described herein are incorporated by reference in their entirety.

BRIEF DESCRIPTION OF THE DRAWINGS

FIGS. 1A and 1B show the BLAST alignment of adrenomedullin peptide query sequence (SEQ ID NO: 43) with the hypothetical protein XP_147916 (SEQ ID NO: 44) and alignment of the human adrenomedullin precursor (SEQ ID NO: 46) with the full-length hypothetical mouse protein XP_147916 (SEQ ID NO: 45), respectively. Like residues are shaded in dark gray while residues with similar chemical nature are shaded in light gray.

FIG. 2 shows the sequence of the entire protein XP_147916 (SEQ ID NO: 45), now renamed mouse AFP-6, in FASTA format.

FIG. 3 shows the alignment of mouse (SEQ ID NO: 45) and human AFP-6 precursor proteins (SEQ ID NOs: 50 and 51) performed by AlignX® (Vector NTI®; Invitrogen) and exported to BOXSHADE for shading. Like residues are shaded in dark gray while residues with similar chemical nature are shaded in gray.

FIG. 4 shows the alignment of human adrenomedullin (SEQ ID NO: 46) and human AFP-6 precursor (SEQ ID NO: 51) proteins performed by AlignX® (Vector NTI®; Invitrogen) and exported to BOXSHADE for shading. Like residues are shaded in dark gray while residues with similar chemical nature are shaded in light gray.

FIG. 5 shows the alignment by AlignX® (Vector NTI®; Invitrogen) of Amylin Family polypeptides: hAFP-6 (SEQ ID NO: 1), hAdrenomedullin (SEQ ID NO: 9), hAmylin (SEQ ID NO: 5), hCGRP 1 (SEQ ID NO: 7), and hCalcitonin (SEQ ID NO: 6). Like residues are shaded in dark gray while residues with similar chemical nature are shaded in light gray.

FIG. 6 shows predicted mature bioactive peptides from human and mouse AFP-6 precursors based on homology with Adrenomedullin.

FIG. 7 shows the alignment of the 5' UTR of human prostate AFP-6 cDNA (SEQ ID NO: 57) aligned with database sequence NM024866 (SEQ ID NO: 58).

DETAILED DESCRIPTION OF THE INVENTION

Figures 8A, 8B, 8C, 8D, 8E, 8F, 8G, 8H, 8I:
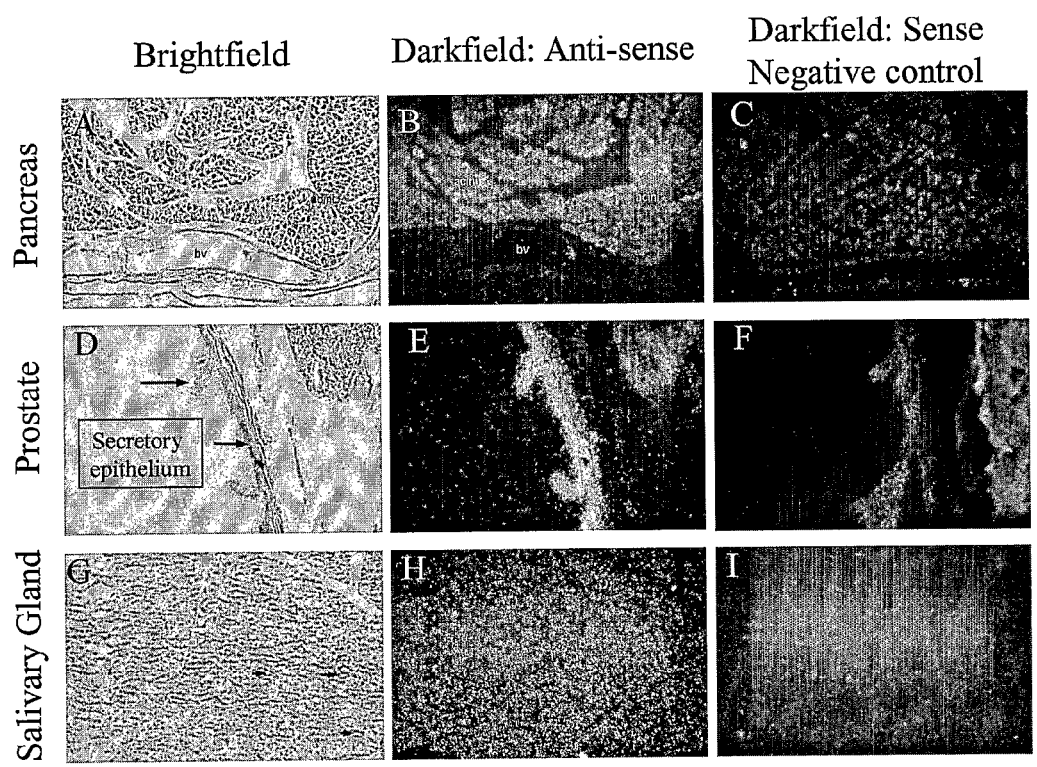
FIGS. 8A-8I show selected in situ hybridization data from the pancreas, prostate and salivary gland.

The present invention relates to the discovery of novel AFP-6 analogs. Through research efforts designed to understand the structure and function of AFP-6, in combination with an understanding of the other Amylin Family polypeptides, novel compounds and their uses are herein described. These compounds, termed AFP-6 analogs, are useful in the treatment and prevention of, among other things, metabolic conditions and disorders. One desirable characteristic of AFP-6 analogs is that they can be designed to favor certain Amylin Family receptors over others (e.g., possess a certain binding profile), which may lead to more effective treatments, fewer side effects, increased stability or solubility, increased activity, increased ease of manufacturing or use of the peptide, for example, making it more economical to produce. Accordingly, peptide analogs are of great interest for clinical use and the development of therapies of conditions involving physiologies which include, but are not limited to, hypertension and maintenance of cardiovascular homeostasis; pulmonary diseases, pregnancy (or infertility) and lactation; gastrointestinal; glucose regulation, obesity, metabolic syndrome and other metabolic disorders.

In certain embodiments, the AFP-6 analogs of the invention may have comparable or higher potency in the treatment and/or prevention of hypertension and cardiovascular conditions; fertility (or infertility) and lactation; pulmonary disorders; and gastrointestinal conditions and conditions associated with hyper- or hypoglycemia, as compared to native AFP-6 polypeptides. In other embodiments, the AFP-6 analogs of the invention may have weaker, though still effective, potency in the treatment and/or prevention of the above described conditions, but may possess other desirable characteristics over native AFP-6, e.g., increased stability or solubility, less side effects, combination of biological activities, and/or ease in manufacturing, formulating, or use. In still other embodiments, AFP-6 analogs of the invention have antagonist activity that blocks, or reduces, AFP-6 activity. Accordingly, the AFP-6 antagonist analogs of the invention are of use, for example, in the prevention or treatment of wasting diseases or disorders.

Section headings are used herein for organizational purposes only and are not to be construed as in any way limiting the subject matter described.

AFP-6 Analogs

AFP-6 analogs of the invention include, but are not limited to, compounds having at least amino acids 18-27 and 41-47 of SEQ ID NO:1; amino acids 18-27 and 33-47 of SEQ ID NO:1, wherein the amino acid at positions 35 and 40 is either D or E; amino acids 18-27, 36-39 and 41-47 of SEQ ID NO:1; or any of the aforementioned compounds further having a loop at the N terminal end, such as a disulfide or amide loop, provided that the AFP-6 analog is not SEQ ID NOs:1-4 or amino acids 16-47 or 17-47 of SEQ ID NO:1. In certain embodiments, AFP-6 analogs may be characterized by having no more than 28, 29, 30, 31, 32, 33, 34, 35, 36, 37, 38, 39, 40, 41, 42, 43, 44, 45, or 46 amino acids. In other embodiments, AFP-6 analogs may have 47, 48, 49 amino acids or more. In some embodiments, AFP-6 analogs have an Amylin Family activity, such as amylin, calcitonin, CGRP, adrenomedullin, or AFP-6 activity, such as those described herein. In some embodiments, AFP-6 analogs have Amylin Family antagonist activity. Thus, "AFP-6 analog" refers to peptide with either agonist or antagonist activity. Whether an AFP-6 analog is an agonist or an antagonist can be determined by using any of the biological assays described herein.

AFP-6 analogs of the invention may include compounds having at least formula (I)

$X_1$-$X_2$-$X_3$-$X_4$-$X_5$-$X_6$-$X_7$-$X_8$-QVQNLSHRLWQL-$X_{21}$-$X_{22}$-$X_{23}$-$X_{24}$-$X_{25}$-$X_{26}$-$X_{27}$-$X_{28}$-SAPV-$X_{33}$-PSSPHSY (SEQ ID NO: 41) wherein $X_1$ is absent, TQAQLLRVG (SEQ ID NO: 42), any of one or more consecutive amino acids of SEQ ID NO: 42, N-aryl, or N-acyl with a substituent selected from a C1-C18 alkyl, a substituted alkyl or a heteroaryl moiety;

$X_2$ is M, S, C, substituted L, K, D, or E, where the side chain can be linked via an amide bond, or any amino acid that can form a bond with $X_8$, for example a disulfide or an amide bond;

$X_3$ is V, D, L, G, N, A, or S;
$X_4$ is V, D, L, G, N, A, S or T;
$X_5$ is V, D, L, G, N, A, or S;
$X_6$ is V, D, L, G, N, A, S, or absent;
$X_7$ is T, S, homoserine, (S)-2-Amino-3-hydroxy-3-methybutanoic acid (Ab) or (2R,3R)-2-Amino-3-hydroxy-4-methylpentanoic acid (Ap);
$X_8$ is M, S, C, substituted L, K, D, or E, or any amino acid that can form a bond with $X_2$, for example a disulfide or an amide bond;
$X_{21}$ is M, G, P, A, or absent;
$X_{22}$ is M, G, P, A, or absent;
$X_{23}$ is M, G, P, A, or absent;
$X_{24}$ is M, G, P, A, or absent;
$X_{25}$ is M, G, P, A, or absent;
$X_{26}$ is R or absent, wherein when $X_{26}$ is absent, $X_{27}$ is absent;
$X_{27}$ is Q or absent, wherein when $X_{27}$ is absent, $X_{26}$ is absent;
$X_{28}$ is D or E;
$X_{33}$ is D or E;
wherein the AFP-6 analog is not SEQ ID NOs: 1 or 2.

In other embodiments, novel AFP-6 analogs comprise, or the active region consists of, an amino acid sequence of formula (II):

$X_1$-$X_2$-QNLSHRLWQL-$X_{13}$-$X_{14}$-$X_{15}$-$X_{16}$-$X_{17}$-$X_{18}$-$X_{19}$-$X_{20}$-SAPV-$X_{25}$-PSSPHSY (SEQ ID NO: 56) wherein $X_1$ is Q or absent;
$X_2$ is V or absent;
$X_{13}$ is M, G, P, A, or absent;
$X_{14}$ is M, G, P, A, or absent
$X_{15}$ is M, G, P, A, or absent;
$X_{16}$ is M, G, P, A, or absent;
$X_{17}$ is M, G, P, A, or absent,
$X_{18}$ is R or absent, wherein when $X_{18}$ is absent, $X_{19}$ is absent;
$X_{19}$ is Q or absent, wherein when $X_{19}$ is absent, $X_{18}$ is absent
$X_{20}$ is D or E;
$X_{25}$ is D or E; and
biologically active fragments thereof, wherein the amino acid sequence is not SEQ ID NOs: 13 or 14.

The AFP-6 analogs may or may not be amidated at the C-terminal end. AFP-6 analogs encompassed by certain variations of formula (I) are further contemplated. For example, in certain embodiments, $X_1$ is absent. In other embodiments, $X_1$ is RVG. In yet other embodiments, $X_1$ is VG. In still other embodiments, $X_1$ is Gly. In still other embodiments, $X_1$ is Val. In certain embodiments, $X_2$ and $X_8$ are Cys. In other embodiments, $X_2$ and $X_8$ are substituted Leu, Lys, or Asp. In yet other embodiments, $X_2$ and $X_8$ are Met. In yet other embodiments, $X_2$ and/or $X_8$ are Glu. In still other embodiments, $X_2$ and $X_8$ are amino acids having side chains that can be chemically bonded to each other to form an intramolecular linkage. Such side chains for $X_2$ and $X_8$ include groups derived from alkyl sulfhydryls which may form disulfide bonds; alkyl acids and alkyl amines which may form cyclic lactams; alkyl aldehydes or alkyl halides and alkylamines which may condense and be reduced to form an alkyl amine bridge; or side chains which may be connected to form an alkyl, alkenyl, alkynyl, ether or thioether bond.

In certain embodiments of AFP-6 analogs encompassed by formula (I), $X_3$ is Val. In other embodiments, $X_3$ is Asn. In still other embodiments, $X_3$ is Gly. In certain embodiments, $X_4$ is Leu. In other embodiments, $X_4$ is Thr. In still other embodiments, $X_4$ is Asn. In certain embodiments, $X_5$ is Gly. In other embodiments, $X_5$ is Ala. In still other embodiments, $X_5$ is Leu. In certain embodiments, $X_6$ is absent. In other embodiments, $X_6$ is Ser. In certain embodiments, $X_3$ is Val, $X_4$ is Leu, Xs is Gly, and $X_6$ is absent. In other embodiments, $X_3$ is Asn, $X_4$ is Thr, Xs is Ala, and $X_6$ is absent. In still other embodiments, $X_3$ is Gly, $X_4$ is Asn, Xs is Leu, $X_6$ is Ser.

In certain embodiments of AFP-6 analogs encompassed by formula (I), $X_7$ is Thr. In certain embodiments, $X_{21}$ to $X_{25}$ are absent. In other embodiments, $X_{21}$ is Met. In other embodiments, $X_{22}$ is Gly. In other embodiments, $X_{23}$ is Pro. In other embodiments, $X_{24}$ is Ala. In other embodiments, $X_{25}$ is Gly. In certain embodiments, $X_{26}$ is R and $X_{27}$ is Q. In other embodiments, $X_{26}$ and $X_{27}$ are absent. In certain embodiments, $X_{28}$ and/or $X_{33}$ are Asp. In other embodiments, $X_{28}$ and/or $X_{33}$ are Glu.

AFP-6 analogs encompassed by certain variations of formula (II) are further contemplated. In certain embodiments, $X_{13}$ to $X_{17}$ are absent. In other embodiments, $X_{13}$ is Met. In other embodiments, $X_{14}$ is Gly. In other embodiments, $X_{15}$ is Pro. In other embodiments, $X_{16}$ is Ala. In other embodiments, $X_{17}$ is Gly. In certain embodiments, $X_{18}$ is R and $X_{19}$ is Q. In other embodiments, $X_{18}$ and $X_{19}$ are absent. In certain embodiments, $X_{20}$ and/or $X_{25}$ are Asp. In other embodiments, $X_{20}$ and/or $X_{25}$ are Glu.

In certain embodiments, the AFP-6 analog is 30 or 31 amino acids in length. In other embodiments, the AFP-6 analog is 32 amino acids in length. In yet other embodiments, the AFP-6 analog is 33, 34, 35, 36, 37, 38, 39, 40, 41, 42, 43, 44, 45, or 46 amino acids in length. In still other embodiments, the AFP-6 analog is 47 or 48 amino acids or more in length. In certain embodiments, the AFP-6 analog is 23, 24, 25, 26, 27, 28, or 29 amino acids in length.

AFP-6 analogs having antagonist activity may include, for example, compounds of formula (I) wherein $X_1$ to $X_5$ are deleted. Other AFP-6 analogs having antagonist activity may include compounds of formula (II) with the proviso that the AFP-6 analog antagonist is not SEQ ID NO: 13 or 14 (amino acids 16-47 or 17-47 of SEQ ID NO: 1). Other AFP-6 analogs having antagonist activity may include compounds of formula (II) wherein $X_1$ and/or $X_2$ are deleted, with the proviso that the AFP-6 analog antagonist is not SEQ ID NO: 13 or 14. Exemplary AFP-6 analog antagonists include SEQ ID NOs: 13, 14, and 34. Moreover, AFP-6 analog antagonists may include internal substitutions or deletions. For example, the Trp at position 9 of SEQ ID NO: 14 is deleted creating the peptide of SEQ ID NO: 15. An exemplary AFP-6 analog antagonist is SEQ ID NO: 15.

Exemplary AFP-6 analogs of the present invention include:

```
                                              (SEQ ID NO: 10)
RVGCVLGTCQVQNLSHRLWQLMGPAGRQDSAPVDPSSPHSY-NH2

(SEQ ID NO: 11)
GCVLGTCQVQNLSHRLWQLMGPAGRQDSAPVDPSSPHSY-NH2

(SEQ ID NO: 12)
CVLGTCQVQNLSHRLWQLMGPAGRQDSAPVDPSSPHSY-NH2

(SEQ ID NO: 13)
QVQNLSHRLWQLMGPAGRQDSAPVDPSSPHSY-NH2

(SEQ ID NO: 14)
VQNLSHRLWQLMGPAGRQDSAPVDPSSPHSY-NH2

(SEQ ID NO: 15)
VQNLSHRL-QLMGPAGRQDSAPVDPSSPHSY-NH2

(SEQ ID NO: 16)
TQAQLLRVGCVLGTCQVQNLSHRLWQL----RQDSAPVDPSSPHSY-NH2

(SEQ ID NO: 17)
TQAQLLRVGCVLGTCQVQNLSHRLWQL------DSAPVDPSSPHSY-NH2

(SEQ ID NO: 18)
VGCVLGTCQVQNLSHRLWQL-----RQDSAPVDPSSPHSY-NH2

(SEQ ID NO: 19)
CVLGTCQVQNLSHRLWQL-----RQESAPVEPSSPHSY-NH2

(SEQ ID NO: 20)
TQAQLLRVGCSNLSTCQVQNLSHRLWQLMGPAGRQDSAPVDPSSPHSY-
NH2

(SEQ ID NO: 21)
TQAQLLRVGCNTATCQVQNLSHRLWQLMGPAGRQDSAPVDPSSPHSY-
NH2

(SEQ ID NO: 22)
RVGCGNLSTCQVQNLSHRLWQLMGPAGRQDSAPVDPSSPHSY-NH2

(SEQ ID NO: 23)
TQAQLLRVGCDTATCQVQNLSHRLWQLMGPAGRQDSAPVDPSSPHSY-
NH2

(SEQ ID NO: 24)
TQAQLLRVGCGNLSTCQVQNLSHRLWQLMGPAGRQDSAPVDPSSPHSY-
NH2

(SEQ ID NO: 25)
TQAQLLRVGMVLGTMQVQNLSHRLWQLMGPAGRQDSAPVDPSSPHSY-
NH2

(SEQ ID NO: 26)
GMVLGTMQVQNLSHRLWQLMGPAGRQDSAPVDPSSPHSY-NH2

(SEQ ID NO: 27)
VGMVLGTMQVQNLSHRLWQL-----RQDSAPVDPSSPHSY-NH2

(SEQ ID NO: 28)
RVGCGNLSTCQVQNLSHRLWQLMGPAGRQDSAPVDPSSPHSY-NH2

(SEQ ID NO: 29)
VGCGNLSTCQVQNLSHRLWQL-----RQDSAPVDPSSPHSY-NH2

(SEQ ID NO: 30)
V-CNTA-TCQVQNLSHRLWQL-----RQDSAPVDPSSPHSY-NH2

(SEQ ID NO: 31)
GCNTATCQVQNLSHRLWQL-----RQDSAPVDPSSPHSY-NH2

(SEQ ID NO: 32)
TQAQLLRVGCVLGTCQVQNLSHRLWQLMGPAGRQESAPVEPSSPHSY-
NH2

(SEQ ID NO: 33)
TQAQLLRVGCVLGTCQVQNLSHRLWQLMGPAGRQDSAPVEPSSPHSY-
NH2

(SEQ ID NO: 34)
GTMQVQNLSHRLWQL-----RQDSAPVEPSSPHSY-NH2

(SEQ ID NO: 35)
VGCVLGTCQVQNLSHRLWQLMGPAGRQDSAPVEPSSPHSY-NH2

(SEQ ID NO: 36)
VGCVLGTCQVQNLSHRLWQL-----RQDSAPVEPSSPHSY-NH2

(SEQ ID NO: 37)
GCNTATCQVQNLSHRLWQL-----RQDSAPVEPSSPHSY-NH2
```

```
                                             (SEQ ID NO: 38)
GCSNLSTCQVQNLSHRLWQL-----RQDSAPVEPSSPHSY-NH2

(SEQ ID NO: 39)
GCGNLSTCQVQNLSHRLWQL-----RQDSAPVEPSSPHSY-NH2

(SEQ ID NO: 40)
GCVLGTCQVQNLSHRLWQL-----RQESAPVEPSSPHSY-NH2.
```

AFP-6 analogs may also include polypeptides having an amino acid sequence with at least 80, 82, 84, 86, 88, 90, 92, 94, 96, 97, or 98% amino acid identity to any amino acid sequence of SEQ ID NOs: 1-4 and 10 to 40 and having 1) a similar activity to any one of SEQ ID NOs: 1 to 40, or an Amylin Family activity or 2) an antagonist activity of the aforementioned activity, wherein the AFP-6 analog is not SEQ ID NOs: 1-9, or known species variants thereof, or SEQ ID NOs: 13 or 14. Percent identity is determined by analysis with the AlignX® module in Vector NTI® (Invitrogen; Carlsbad Calif.).

Compounds of the invention may further include additional amino acids, chemicals, or moieties that do not affect the biological activity or function of the peptide but may perform other functions, such as aiding purification (e.g., histidine tag), detection (e.g., biotin), or expression (e.g., expression cassettes/vectors and promoters).

The AFP-6 analogs of the invention may also be further derivatized by chemical alterations such as amidation, glycosylation, acylation, sulfation, phosphorylation, acetylation, and cyclization. Such chemical alterations may be obtained through chemical or biochemical methodologies, as well as through in vivo processes, or any combination thereof. Derivatives of the analog polypeptides of the invention may also include conjugation to one or more polymers or small molecule substituents. One type of polymer conjugation is linkage or attachment of polyethylene glycol ("PEG") polymers, polyamino acids (e.g., poly-his, poly-arg, poly-lys, etc.) and/or fatty acid chains of various lengths to the N- or C-terminus or amino acid residue side chains of an AFP-6 analog. Small molecule substituents include short alkyls and constrained alkyls (e.g., branched, cyclic, fused, adamantyl), and aromatic groups. In addition, basic residues such as R and K may be replaced with homoR and homoK, citrulline, or ornithine to improve metabolic stability of the peptide. AFP-6 analogs also include acid as well as amide forms of the peptides.

AFP-6 analogs also include biologically active fragments of the larger peptides described herein. Examples of the desired activity include (1) having activity in a food intake, gastric emptying, pancreatic secretion, blood pressure, heart rate or weight loss assay similar to an AFP-6 polypeptide or Amylin Family polypeptide of the present invention, and/or (2) binding in a receptor binding assay for an Amylin Family receptor (e.g., amylin receptor, calcitonin receptor). Exemplary binding assays of Amylin Family receptors are described herein and described in U.S. Pat. No. 5,264,372, the entirety of which is incorporated herein by reference.

In one embodiment, AFP-6 analogs will bind in such assays with an affinity of greater than 1 µM, and, in another embodiment, with an affinity of greater than 1-10 nM. It is also contemplated that AFP-6 analogs may also possess the desired activity by indirectly interacting with an amylin-family receptor (e.g., amylin, calcitonin, CGRP or adrenomedullin) or bind to other receptor or receptors with which an AFP-6 polypeptide itself may interact to elicit a biological response.

The agonist polypeptides of the present invention will generally retain, at least in part, a biological Amylin Family activity, such as an AFP-6 activity. In other words, Amylin Family activity includes amylin activity, calcitonin activity, adrenomedullin activity, CGRP activity or AFP-6 activity. Table 2 provides a summary of Amylin Family biological effects as published in Wimalawansa (1997) *Critical Reviews in Neurobiology* 11:167-239.

TABLE 2

Summary of Biological effect of CGRP, CT, Amylin, and Adrenomedullin

| Biological effect | CGRP | Calcitonin | Amylin | ADM |
|---|---|---|---|---|
| Vasodilation | ++++ | +/− | ++ | ++ |
| Chronotropic | ++ | − | ++ | + |
| Inotropic | ++ | − | ++ | + |
| Inhibit bone resorption | + | ++++ | ++ | +/− |
| Stimulate bone formation | − | − | + | − |
| Calcium-lowering effect | − | +++ | ++ | − |
| Growth factor-like effect | + | − | + | + |
| Neural regeneration | ++ | +/− | − | − |
| Thermoregulation | + | − | + | +/− |
| Inflammation | ++ | +/− | − | − |
| Gastric mucosal protection | ++ | − | − | − |
| Effects on β cells | + | +/− | ++ | − |
| Skeletal muscle | + | − | + | − |
| Glucose metabolism | + | − | + | − |
| Anorectic effect | + | ++ | ++ | + |
| Analgesic effect | − | ++ | + | − |

By a polypeptide having "amylin activity" is meant that the polypeptide demonstrates similar physiological characteristics as amylin, such as those known in the art as well as those described in the instant specification, for example, in reducing food intake. The polypeptides of the present invention may be capable of binding to or otherwise directly or indirectly interacting with an amylin receptor, or other receptor or receptors with which amylin itself may interact to elicit a biological response, e.g., reducing food intake.

By a polypeptide having "calcitonin activity" is meant that the polypeptide demonstrates similar physiological characteristics as calcitonin, such as those known in the art as well as those described in the instant specification, for example, inhibiting osteoclast function. The polypeptides of the present invention may be capable of binding to or otherwise directly or indirectly interacting with a CT receptor, or other receptor or receptors with which calcitonin itself may interact to elicit a biological response, e.g., inhibiting osteoclast function.

By a polypeptide having "CGRP activity" is meant that the polypeptide demonstrates similar physiological characteristics as CGRP, such as those known in the art as well as those described in the instant specification, for example, eliciting a vasodilatory effect. The polypeptides of the present invention may be capable of binding to or otherwise directly or indirectly interacting with a CGRP receptor, or other receptor or receptors with which CGRP itself may interact to elicit a biological response, e.g., eliciting a vasodilatory effect.

By a polypeptide having "adrenomedullin activity" is meant that the polypeptide demonstrates similar physiological characteristics as ADM, such as those known in the art as well as those described in the instant specification, for example, eliciting a hypotensive effect. The polypeptides of the present invention may be capable of binding to or otherwise directly or indirectly interacting with an ADM receptor, or other receptor or receptors with which ADM itself may interact to elicit a biological response, e.g., eliciting a hypotensive effect.

By a polypeptide having "AFP-6 activity" is meant that the polypeptide demonstrates similar physiological characteristics as AFP-6, such as those known in the art as well as those described in the instant specification, for example, eliciting a hypotensive effect. The polypeptides of the present invention are capable of binding to or otherwise directly or indirectly interacting with receptor or receptors with which AFP-6 itself may interact to elicit a biological response, e.g., eliciting a hypotensive effect.

In another aspect of the invention, AFP-6 analogs with antagonist activity will generally inhibit or reduce, at least in part, a biological Amylin Family activity, such as AFP-6 activity. In other words, the amylin, calcitonin, CGRP, adrenomedullin and/or AFP-6 activity is blocked by the antagonist analog.

Table 3 summarizes the results for Amylin Family polypeptides in a food intake assay and various Amylin Family receptor-binding assays. Tables 6 and 7, in the Example section, summarize the results of some AFP-6 analog Food Intake and binding assay results, respectively.

TABLE 3

Amylin Family Food Intake (FI) and Receptor Binding data

| Compound | FI 30 min ED$_{50}$ nmole/kg | FI 60 min ED$_{50}$ nmole/kg | Amylin RBA | IC$_{50}$ nM rCalcitonin RBA | CGRP RBA |
|---|---|---|---|---|---|
| AFP-6 | 9-14 | 14-19 | 13 | 32 | 3 |
| r/h Amylin | 11-25 | 25-33 | 0.16 | 2.8 | 12 |
| r/h CGRP | 0.9 | 4.2 | 0.57 | 104.8 | 0.02 |
| r/h Calcitonin | >270 | >270 | 100 | 1.3-3.4 | 1000 |
| r/h Adreno-medullin | 18 | 13 | 123 | 33-68 | 0.3 |

Given the biological activity and/or receptor binding activity described herein, the present invention provides AFP-6 analogs and AFP-6 analog compositions for use in a medicament for treating a disease or disorder in a subject in need thereof. The present invention also provides methods for use of AFP-6 analogs and AFP-6 analog compositions in treating a disease or disorder in a subject.

As such, in one aspect, the present invention provides AFP-6 agonist analog compositions and methods of using them to reduce weight in a subject; affect body composition; treat diabetes, including type 2 or non-insulin dependent diabetes, type 1 diabetes and gestational diabetes; and to treat eating disorders, pain, insulin-resistance syndrome, metabolic syndrome, cardiovascular disease, pulmonary disease, infertility, or conditions affecting bone.

In yet another aspect, the present invention provides AFP-6 antagonist analog compositions and methods of using them, such that their ability to block the effects of amylin, calcitonin, CGRP, adrenomedullin, or AFP-6 can be beneficial to the subject in treating, for example, anorexia, cachexia, bulimia, and other wasting diseases characterized by loss of appetite, diminished food intake, body weight loss, or hypotension.

By "AFP-6" is meant an AFP-6 polypeptide obtained or derived from any species. Thus, the term "AFP-6" includes the human full-length amino acid peptide, and species variations of AFP-6, including e.g., murine, hamster, chicken, bovine, rat, and dog AFP-6 polypeptide. In this sense, "AFP-6 polypeptide" and "wild-type AFP-6 polypeptide" or "native AFP-6 polypeptide," i.e., unmodified AFP-6 polypeptide, are used interchangeably.

By "AFP-6 agonist" is meant any compound, including peptide, peptide-like compounds and small molecules, that elicits similar biological activities as AFP-6.

By "amino acid" and "amino acid residue" is meant natural amino acids, unnatural amino acids, and modified amino acid, all in their D and L stereoisomers if their structure allows such stereoisomeric forms. Natural amino acids include alanine (Ala), arginine (Arg), asparagine (Asn), aspartic acid (Asp), cysteine (Cys), glutamine (Gln), glutamic acid (Glu), glycine (Gly), histidine (His), isoleucine (Ile), leucine (Leu), Lysine (Lys), methionine (Met), phenylalanine (Phe), proline (Pro), serine (Ser), threonine (Thr), typtophan (Trp), tyrosine (Tyr) and valine (Val). Unnatural amino acids include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisobutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homolysine, homoproline, homoserine, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, norleucine, ornithine, pentylglycine, pipecolic acid and thioproline, homolysine, homoarginine, homoserine, citrulline, ornithine, Ne-formyllysine. Modified amino acid include the natural and unnatural amino acids which are chemically blocked, reversibly or irreversibly, or modified on their N-terminal amino group or their side chain groups, as for example, methionine sulfoxide, methionine sulfone, S (carbo amino group or side chain functional group has been chemically codified to another functional group. For example, aspartic acid-(beta-methyl ester) is a modified amino acid of aspartic acid; N-ethylglycine is a modified amino acid of glycine; or alanine carboxamide is a modified amino acid of alanine. Additional residues that can be incorporated are described by Sandberg et. al. (1998) *J. Med. Chem.* 41:2481-2491.

In one embodiment, the AFP-6 agonist analogs of the invention retain or affect, by at least about 25%, about 30%, 40%, 50%, 60%, 70%, 80%, 90%, 95%, 98%, or 99%, the biological activity of an AFP-6 polypeptide or another polypeptide of the Amylin Family. In another embodiment, the agonist analog polypeptides of the invention exhibit improved activity over at least one of the other Amylin Family polypeptides. For example, the agonist analog polypeptides of the invention exhibit at least about 110%, 125%, 130%, 140%, 150%, 200%, or more of the biological activity of an AFP polypeptide or another polypeptide of the Amylin Family. An exemplary function of AFP-6 is the reduction of food intake or blood pressure.

Exemplary AFP-6 analogs are those having a potency in one of the assays described herein (for example, receptor binding assays, food intake, and/or weight reduction assays) which is greater than or equal to the potency of human AFP-6 polypeptide in that same assay. For example, the AFP-6 analogs may bind to at least one of the receptors with an affinity of greater than 30 nM, 20 nM, 10 nM, or more, alternatively with an affinity of greater than that of a native adrenomedullin or one of the other Amylin Family polypeptides. However, it is also contemplated that AFP-6 analogs of the invention can have less potency in the assays. AFP-6 analogs may further possess desirable characteristics, such as a specific binding profile, stability, solubility, or ease in manufacturing or formulation.

In one example, the polypeptides of the present invention may demonstrate activity in food intake assays. Such polypeptides demonstrate the ability to reduce cumulative food intake by more than 5% over administration of the vehicle, more than 15%, more than 25%, more than 35%, or more than 50% over the vehicle. In a one embodiment, the AFP-6 analog reduces food intake by more than 75 or even 90%.

In another general aspect, the invention includes nucleic acids that can encode the AFP-6 analogs herein described. Such nucleic acids can be determined from the amino acid sequences provided herein using standard coding table well known in the art.

Uses of AFP-6, AFP-6 Agonists and AFP-6 Analogs

Given the biological activity and/or receptor binding activity described herein, the present invention provides AFP-6 analogs and AFP-6 analog compositions for use in a medicament for treating a disease or disorder in a subject in need thereof. The present invention also provides methods for use of AFP-6 analogs and AFP-6 analog compositions in treating a disease or disorder in a subject.

As used herein, and as well-understood in the art, "treatment" is an approach for obtaining beneficial or desired results, including clinical results. "Treating" a disease, disorder, or condition means that the extent and/or undesirable clinical manifestations of a condition, disorder, or a disease state are lessened and/or time course of the progression is slowed or lengthened, as compared to not treating the disorder. For example, in treating obesity, a decrease in body weight, e.g., a 5% decrease in body weight, is an example of a desirable treatment result. For purposes of this invention, beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment. Further, treating does not necessarily occur by administration of one dose, but often occurs upon administration of a series of doses. Thus, a therapeutically effective amount or an amount sufficient to treat a disease, disorder, or condition may be administered in one or more administrations.

As such, in one aspect, the present invention provides AFP-6 agonist analog compositions and methods of using them to reduce weight in a subject; affect body composition; treat diabetes, including type 2 or non-insulin dependent diabetes, type 1 diabetes and gestational diabetes; and to treat eating disorders, pain, insulin-resistance syndrome, metabolic syndrome, cardiovascular disease, pulmonary disease, infertility, and/or conditions affecting bone.

In yet another aspect, the present invention provides AFP-6 antagonist analog compositions and methods of using them, such that their ability to block the effects of amylin, calcitonin, CGRP, adrenomedullin, or AFP-6 can be beneficial to the subject in treating, for example, anorexia, cachexia, bulimia, and/or other wasting diseases characterized by loss of appetite, diminished food intake, body weight loss, or hypotension.

Based upon the pharmacologic activities described herein, AFP-6, AFP-6 agonists and AFP-6 analogs may be useful for the treatment of metabolic diseases (including various manifestations of diabetes mellitus and dysglycemia, insulin resistance and insulin resistance syndrome, obesity, dyslipidemia); the treatment of gastrointestinal disorders, including gastritis, Barrett's and other esophagitis, pancreatitis, and irritable bowel syndrome; the treatment of disorders related to or that can be ameliorated by regulating the rate of gastric emptying (e.g., dumping syndrome, moderating postprandial glucose levels and gastric hypomotility); the treatment of cardiovascular and renal disorders, including hypertension, renal failure, vascular occlusive disorders (including ischemia-reperfusion injury and stroke); the treatment of congestive heart failure and other ventricular dysfunctions and cardiac dysrhythmias and as a cardioprotective and/or myoprotective agent, especially in association with myocardial infarction; the treatment of pulmonary disorders, including pulmonary hypertension, bronchospasm, chronic obstructive pulmonary disease and disorders of ventilation-perfusion mismatch; the treatment of pain, including bone pain, migraine, and other conditions where opiate-sparing is desired; the treatment of bone disorders, including osteomalacia or disorders of mineralization, for the promotion of osteogenesis and fracture repair; the treatment of ghrelin related disorders, including relative growth-hormone and/or IGF1 excess; the treatment of glucagon-related disorders; and for the release of prolactin, which has effects on the uterus and pregnancy, in growth hormone release, and in ovarian follicle survival and growth.

In particular, AFP-6, AFP-6 agonists and AFP-6 agonist analogs may be used to treat conditions or disorders which can be alleviated by reducing caloric (or nutrient) intake or availability. This would include any condition or disorder in a subject that is either caused by, complicated by, or aggravated by a relatively high nutrient intake or availability, or that can be alleviated by reducing nutrient intake or availability, for example by decreasing food intake. Such conditions or disorders include, but are not limited to, obesity, diabetes mellitus, including type 2 diabetes, eating disorders, and insulin-resistance syndromes.

Obesity and its associated disorders are common and very serious public health problems in the United States and throughout the world. Upper body obesity is the strongest risk factor known for type 2 diabetes mellitus, and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia (see, e.g., Kopelman, Nature 404: 635-43 (2000)). It reduces life-span and carries a serious risk of co-morbidities as listed above, as well as disorders such as infections, varicose veins, acanthosis nigricans, eczema, exercise intolerance, insulin resistance, hypertension hypercholesterolemia, cholelithiasis, orthopedic injury, and thromboembolic disease (Rissanen et al, BMJ 301: 835-7 (1990)).

Obesity is also a risk factor for the group of conditions called insulin resistance syndrome, or "Syndrome X." Recent estimates for the medical cost of obesity and associated disorders is $150 billion worldwide. The pathogenesis of obesity is believed to be multifactorial but the basic problem is that in obese subjects nutrient availability and energy expenditure do not come into balance until there is excess adipose tissue. Obesity is currently a poorly treatable, chronic, essentially intractable metabolic disorder.

It is now disclosed that AFP-6, AFP-6 agonists and AFP-6 agonist analogs may be administered to treat obesity and related conditions or prevent/reduce the risk of other disease states as described herein. Related conditions include, but are not limited to, insulin resistance, diabetes mellitus, hypertension, cardiovascular disease, pseudotumor, cerebri, hyperlipidemia, sleep apnea, cancer, pulmonary hypertension, cardiovascular disease, cholecystitis, and osteoarthritis.

AFP-6, AFP-6 agonists, and AFP-6 agonist analogs are useful for regulating gastric emptying. These compounds that delay gastric emptying find use in radiological examinations or magnetic resonance imaging. Alternatively, these compounds may be used to reduce gastric motility in a subject suffering from a gastrointestinal disorder, for example, spasm, which may be associated with acute diverticulitis, a disorder of the biliary tract or a disorder of the Sphincter of Oddi. The compounds may also be used to treat post-prandial dumping syndrome or treat post-prandial hyperglycemia.

AFP-6 antagonists that block activity would be useful in disorders that include, but are not limited to anorexia, cachexia, bulimia, and other wasting diseases characterized by loss of appetite, diminished food intake, or body weight loss in addition to hypotension and gastric hypomotility. Accordingly, AFP-6 analogs having antagonist activity to that of an Amylin Family polypeptide, such as AFP-6, and their uses are also contemplated as being part of the invention.

AFP-6, AFP-6 agonists and AFP-6 analogs may also be used to modify body composition, for example, reducing body fat, but not lean body mass or creating a better (larger) lean body to fat ratio. The change in body composition can be by weight (e.g., loss or gain by grams) or by percent body fat and percent lean body mass or protein. Without wishing to be bound by any particular theory, AFP-6, AFP-6 agonists and AFP-6 analogs may have a metabolic effect leading to the desirable loss of body fat, yet preserving lean body mass or minimizing its loss.

While "obesity" is generally defined as a body mass index over 30, for purposes of this disclosure, any subject, including those with a body mass index of less than 30, who needs or wishes to reduce body weight is included in the scope of "obese." In other words, the compounds of the invention are intended to be used in all subjects without regard to their body mass index as long as the desired effect is achieved. For example, the subjects to whom these methods may be of interest include not only those individuals who are overweight or obese, but also those with lean body composition, e.g., body builders and other athletes. It may be desirable for these individuals to reduce or maintain their body weight, e.g., to stay in a certain weight class range, yet preserve or increase their lean body mass for greater strength, stamina, endurance and/or a more muscular appearance. As such in certain embodiments, methods of the invention include reducing body fat or preventing body fat gain. Other embodiments include maintaining or increasing lean body mass. Still other embodiments include controlling body weight and/or sculpting a body's appearance. Such methods may also be used on any animal for which a greater lean body mass to fat ratio is desired. Examples of such use include, but are not limited to, creating a superior show dog, creating a superior racehorse, or meatier, less fatty livestock. These concepts are set forth in more detail in U.S. patent application Ser. No. 10/851,574, filed May 20, 2004, incorporated herein by reference in its entirety.

Another condition, systemic hypertension, is a disease that, if untreated, strongly predisposes one to atherosclerotic cardiovascular disease. It is estimated that as many as 1 in 4 adult Americans have hypertension. Hypertension is usually diagnosed when the average diastolic blood pressure is 90 mm Hg or greater, or systolic blood pressure is 140 mm Hg or greater. Hypertension is approximately twice as common in persons with diabetes as in those without. Special care is warranted in diagnosing hypertension in persons with diabetes because of greater variability of blood pressure and a much greater likelihood of isolated systolic hypertension. The prevalence of hypertension increases with age. AFP-6, AFP-6 agonists and AFP-6 agonist analogs may be administered to reduce arterial blood pressure and, thereby, also reduce edema and inflammatory exudates volume. Hypertension in the pulmonary circulation is less common, but is a serious condition, resulting in significant mortality. AFP-6, AFP-6 agonists and AFP-6 agonist analogs may be useful in the treatment of pulmonary hypertension.

Local hypoxia in the pulmonary vascular physiologically elicits a vasoconstrictive response, to shunt blood away and towards better-ventilated lung segments. However, this mechanism can be overwhelmed in chronic obstructive pulmonary disease, with the resulting pulmonary hypertension and sub-optimal matching of ventilation and perfusion (so called ventilation/perfusion mismatch), sub-optimal oxygen loading, and chronic dyspnoea and exercise intolerance. In general, it is important to match gas (ventilation) to blood flow (perfusion) in local lung regions to obtain optimal gas exchange. Blood flow to unventilated regions of the lung is wasted effort, as is ventilation of unperfused regions since no gas exchange between air and blood can occur in such regions. It has been reported that mismatching of ventilation and perfusion can reduce the effectiveness of the lungs as gas exchange organs to as little as one-tenth normal.

Ventilation/perfusion mismatching is a prevalent cause of pulmonary disability, and may also be present in such conditions as asthma, chronic obstructive pulmonary disease, interstitial lung disease, alveolar disease and pulmonary vascular disease. It is theorized that the combination of (1) bronchodilation, leading to increased regional lung ventilation, (2) vasodilation, leading to increased local lung perfusion, and/or (3) activation of carbonic anhydrase, leading to more rapid outgassing of $CO_2$ (carried in the blood as bicarbonate) would be beneficial in pulmonary disorders where ventilation-perfusion mismatching is a feature.

It is therefore, contemplated that AFP-6, AFP-6 agonists and AFP-6 analogs may be useful in treating conditions such as acute respiratory distress syndrome, asthma, chronic obstructive pulmonary disease, interstitial lung disease, alveolar disease and pulmonary vascular disease and conditions associated with ventilation/perfusion mismatch. It is further contemplated that these compounds may be delivered by inhalation. The peptides may follow the air-flow to the alveoli. Such delivery of the peptides may include delivery as low or ultra-low density particles, such as "whiffle balls," for example US2004-0170568 and U.S. Pat. No. 6,630,169 (incorporated herein by reference in their entirety) or TECHNOSPHERES™ (Pharmaceutical Discovery Corporation, Elmsford, N.Y.). These peptides may increase perfusion (for example, via pulmonary vasodilation) to comparatively better-ventilated parts of the lung, and may increase ventilation via inhibition of bronchospasm. It is further contemplated that ADM or CGRP, agonists and analogs thereof, may also be used either alone or in combination with AFP-6, AFP-6 agonists or AFP-6 analogs to treat conditions such as acute respiratory distress syndrome, asthma, chronic obstructive pulmonary disease, interstitial lung disease, alveolar disease, pulmonary vascular disease or conditions associated with ventilation/perfusion mismatch. In such situations, the teachings in the Pharmaceutical Compositions section of the instant application also apply to ADM and CGRP, their agonists and analogs.

AFP-6, AFP-6 agonists and AFP-6 analogs may stimulate Na/K-ATPase, restoring the ionic milieu in excitable tissues (muscle, including myocardium, and nerves) following ischemic insult and depolarization, and reducing the frequency and severity of abnormal electrical events, such as dysrhythmias.

AFP-6, AFP-6 agonists and AFP-6 analogs may be used as cardioprotective agents, for example to ameliorate ischemic injury, reduce myocardial infarct size consequent to myocardial ischemia or to otherwise limit the extent of myocardial injury. Interest in therapies capable of providing additional myocardial protection which could be administered in conjunction with thrombolytic therapy, or alone, since retrospective epidemiological studies have shown that mortality during the first few years following infarction appears to be related to original infarct size.

Myocardial ischemia is the result of myocardial oxygen supply and demand and includes exertional and vasospastic myocardial dysfunction. Exertional ischemia is generally ascribed to the presence of critical atherosclerotic stenosis involving large coronary arteries resulting in a reduction in subendocardial flow. Vasospastic ischemia is associated with a spasm of focal variety, whose onset is not associated with exertion or stress. The spasm is better defined as an abrupt increase in vascular tone.

Congestive heart failure describes a pump function that is insufficient to deliver enough oxygen to peripheral tissues. This can sometimes be a result of decreased oxygen carrying capacity in the blood (e.g., in severe anemia). It is most commonly a result in reduced cardiac performance (e.g., after myocardial damage) or as a result of increased myocardial work demand (e.g., in the face of increased peripheral resistance with systemic hypertension). Toxic hypervolemia can exacerbate failure by increased filling pressures resulting in cardiac dilatation and suboptimal contractility. AFP-6, AFP-6 agonists and AFP-6 analogs may be useful in the treatment of congestive heart failure through a variety of mechanisms that include reduction of cardiac afterload (vasodilation, shown herein), an increase in cardiaccontractility (exemplified by an increase in dP/dt, shown herein), an amelioration of toxic hypervolemia, an amelioration of ionic disequilibrium.

AFP-6, AFP-6 agonists and AFP-6 analogs may find use in the reduction of edema, for example in rheumatoid arthritis, edema secondary to brain tumors or irradiation for cancer, edema resulting from stroke, head trauma or spinal cord injury, post-surgical edema, asthma and other respiratory diseases and cystoid macular edema of the eye.

AFP-6, AFP-6 agonists and AFP-6 analogs may further be useful in the treatment of renal failure, nephropathy and may be useful as a trophic factor in kidney.

AFP-6, AFP-6 agonists and AFP-6 analogs may be useful in the treatment of pain, and may decrease the need for opiates. It may especially be useful in pain that is associated with vasomotor disturbance, including migraine headache, and in the treatment of inflammation. AFP-6, AFP-6 agonists and AFP-6 analogs may be useful in the treatment of certain gastrointestinal disorders, especially those that can be ameliorated by inhibition of secretions. Such disorders include gastritis, esophagitis (including Barrett's with combined bile and acid reflux) and pancreatitis. It may additionally be useful in the treatment of pain associated with those disorders.

AFP-6, AFP-6 agonists and AFP-6 analogs may be useful in the treatment of demineralization disorders of bone, including osteoporosis, diabetic and other osteopenia. It may additionally promote osteogenesis and be useful in accelerating fracture repair.

AFP-6, AFP-agonist and AFP-6 analog administration may also result in the release of prolactin and regulation of growth hormone release. Prolactin is a polypeptide hormone that is synthesized in and secreted from specialized cells of the anterior pituitary gland, the lactotrophs. Prolactin serves multiple roles in reproduction, but it also plays multiple homeostatic roles in the organism. Synthesis and secretion of prolactin is not restricted to the anterior pituitary gland, other organs and tissues in the body have this capability. The varied effects of prolactin on the mammary gland include growth and development of the mammary gland, synthesis of milk, and maintenance of milk secretion. Lactogenesis clearly requires pituitary prolactin, since hypophysectomy during pregnancy prevents subsequent lactation.

Actions of prolactin on luteal function depend on species and the stage of the estrous cycle. Prolactin acts as a luteotrophic hormone by maintaining the structural and functional integrity of the corpus luteum. This "luteotrophic" action of prolactin is characterized by enhanced progesterone secretion. Prolactin enhances progesterone secretion in two ways: prolactin potentiates the steroidogenic effects of luteinizing hormone (LH) in granulose-luteal cells and inhibits the 20 a hydroxysteroid dehydrogenase enzyme, which inactivates progesterone. In humans, high levels of prolatin inhibit granulose cell luteinization and steroidogenesis. Prolactin is essential for progesterone biosynthesis and luteal cell hypertrophy during pregnancy. In addition to luteal function, the prolactin-R mediates numerous functions in granulose cells and oocytes as well.

Aside from its action on reproductive processes, prolactin plays a role in maintaining the constancy of the internal environment by regulation of the immune system, osmotic balance, and angiogenesis. Prolactin is a common mediator of the immunoneuroendocrine network, where nervous, endocrine, and immune systems communicate with each other. Its main feature is cooperation with cytokines and hemopoietins, and it has been implicated as a "stress hormone," functioning to restore hemapoietic homeostasis under conditions of dysregulation. Prolactin plays a significant role in regulation of the humoral and cellular immune responses in physiological as well as pathological states, such as autoimmune diseases. Immune responses in vivo are enhance by prolactin, including T cell proliferation and mitogenesis; maturation of dendritic cells, etc. Circulating prolactin is elevated in a number of autoimmune diseases, and about 20% of systemic lupus erythematosus (SLE) patients are hyperprolactinemic. Prolactin also regulates solute and water transport across mammalian cell membranes. For example, prolactin exerts a host of activities on transport of solute across mammary epithelial cell membranes. Prolactin decreases the transport of sodium and increases the transport of potassium across mammary epithelial cells. Prolactin also affects chloride, and calcium transport across intestinal epithelial membranes. Prolactin has angiogenic activities; however, angiogenesis is inhibited by proteolytic fragments of native prolactin. Understanding the physiological role of prolactin, as described above, and methods of regulating it, such as by AFP-6, AFP-6 agonists and AFP-6 analogs, can lead to new therapies in regulating imbalances as contemplated herein.

AFP-6, AFP-6 agonists and AFP-6 analogs may secondarily mediate other hormonal responses, including the suppression of ghrelin secretion. It may be useful in the treatment of ghrelin-related disorders, and disorders of the ghrelin-growth hormone-IGF axis, including the treatment of retinopathy.

Moreover, while the mechanism of islet neogenesis remains poorly understood (for review see Bouwen (2004)

Cell Biochem Biophys. 40(3 Suppl): 81-88), it has been hypothesized that de-differentiated or metaplastic exocrine cells (acinar and ductal), acquire a multipotential state and can serve as islet precursors. Since AFP-6 mRNA is in acinar cells and SAGE analysis found the RNA in pancreas epithelium ductal adenocarcinoma, it is possible that AFP-6, AFP-6 agonists, and AFP-6 analogs could be useful for islet neogenesis.

Further, given the expression of AFP-6 mRNA in the secretory epithelium, AFP-6 may be involved in normal prostate function and, thus, it, its agonists and its analogs could be useful in treating various prostate disorders.

AFP-6, AFP-6 agonists and AFP-6 analogs may further be used for screening other compounds having a property of the AFP-6 analogs described herein. Exemplary screening methods are described in PCT application WO 2004/048547, the contents of which are incorporated by reference in its entirety. The present invention provides for antibodies specific for an AFP-6, AFP-6 agonist or AFP-6 analog. Moreover, AFP-6, AFP-6 agonists and AFP-6 analogs and/or their antibodies can also be used in diagnostic applications for determining, or propensity for developing, conditions or disorders as described herein. It is also contemplated that the antibodies may be used as antagonists.

Making AFP-6 Antagonists

The AFP-6 analogs described herein may be prepared using standard recombinant techniques or chemical peptide synthesis techniques known in the art, e.g., using an automated or semi-automated peptide synthesizer, or both. Likewise, the derivatives of the polypeptides of the invention may be produced using standard chemical, biochemical, or in vivo methodologies.

The AFP-6 analogs of the invention can be synthesized in solution or on a solid support in accordance with conventional techniques. Various automatic synthesizers are commercially available and can be used in accordance with known protocols. See, e.g., Stewart and Young, Solid Phase Peptide Synthesis, 2d. ed., Pierce Chemical Co. (1984); Tam et al, *J. Am. Chem. Soc.* 105: 6442 (1983); Merrifield, *Science* 232: 341-7 (1986); and Barany and Merrifield, The Peptides, Gross and Meienhofer, eds., Academic Press, New York, 1-284 (1979).

The AFP-6 analogs of the present invention may alternatively be produced by recombinant techniques well known in the art. See, e.g., Sambrook et al, Molecular Cloning: A Laboratory Manual, 2d ed., Cold Spring Harbor (1989). These polypeptides produced by recombinant technologies may be expressed from a polynucleotide, e.g., a DNA or RNA molecule. These polynucleotide sequences may incorporate codons facilitating transcription and translation of mRNA in host cells. Such manufacturing sequences may readily be constructed according to the methods well known in the art. See, e.g., WO 83/04053. A variety of expression vector/host systems may be utilized to contain and express an AFP-6 analog coding sequence.

As such, the amino acid sequences of the AFP-6 analogs determine the polynucleotide sequences that are useful in generating new and useful viral and plasmid DNA vectors, new and useful transformed and transfected prokaryotic and eukaryotic host cells (including bacterial, yeast, algae, plant, insect, avian, and mammalian cells grown in culture), and new and useful methods for cultured growth of such host cells capable of expression of the present polypeptides. The polynucleotide sequences encoding the AFP-6 analogs, either agonist or antagonist, may also be useful for gene therapy.

DNA sequences encoding the AFP-6 analog may be created using well known molecular biology (or recombinant) techniques such as amplification by PCR or site directed mutagenesis and cloning into an appropriate vector, for example, pGEX-3X (Pharmacia, Piscataway, N.J.).

The present invention also provides for processes for the production of the present AFP-6 analogs. Provided is a process for producing the polypeptides from a host cell containing nucleic acids encoding such AFP-6 analogs comprising: (a) culturing said host cell containing polynucleotides encoding AFP-6 analogs under conditions facilitating the expression of such DNA molecules; and (b) obtaining such AFP-6 analogs. Host cells may be prokaryotic or eukaryotic, such as bacterial, yeast, algae, plant, insect, avian, and mammalian cells. Mammalian host cells include, for example, human cells cultured in vitro. Also contemplated are processes of producing polypeptides using a cell free system. An example of a cell free protein expression system is the Rapid Translation System (RTS) by Roche Diagnostics Corp.

A variety of expression vector/host systems may be utilized to contain and express an AFP-6 analog coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, tobacco mosaic virus) or transformed with bacterial expression vectors (e.g., Ti or pBR322 plasmid); or mammalian cell systems. Mammalian cells that are useful in recombinant protein productions include, but are not limited to, VERO cells, HeLa cells, Chinese hamster ovary (CHO) cell lines, COS cells (such as COS-7), WI 38, BHK, HepG2, 3T3, RIN, MDCK, A549, PC12, K562 and 293 cells. Exemplary protocols for the recombinant expression of the protein in any of these expression/host systems, as well as other expression/host systems, are well known in the art.

It may be desirable to purify the AFP-6 analogs generated by the present invention. Peptide purification techniques are well known to those of skill in the art. These techniques may involve the crude fractionation of the cellular milieu to polypeptide and non-polypeptide fractions. The polypeptides of interest may be further purified using chromatographic and electrophoretic techniques to achieve partial or complete purification (or purification to homogeneity). Analytical methods particularly suited to the preparation of a pure peptide are ion-exchange chromatography, exclusion chromatography, polyacrylamide gel electrophoresis, and isoelectric focusing. A particularly efficient and preferred method of purifying peptides is reverse phase HPLC, followed by characterization of purified product by liquid chromatography/mass spectrometry (LC/MS) and Matrix-Assisted Laser Desorption Ionization (MALDI) mass spectrometry. Additional confirmation of purity is obtained by determining amino acid analysis.

The term "purified peptide" as used herein, is intended to refer to a composition, isolatable from other components, wherein the peptide is purified to any degree relative to its naturally obtainable state. A purified peptide therefore refers to a peptide, free from the environment in which it may naturally occur. The term "substantially purified" is used to refer to a composition in which the peptide forms the major component of the composition, such as constituting at least about 50%, about 60%, about 70%, about 80%, about 90%, about 95% or more of the peptides in the composition. Methods for purifying a polypeptide can be found, for example, in U.S. Pat. No. 5,849,883, incorporated by reference in its entirety.

Various techniques suitable for use in peptide purification are well known in the art. These include, for example, precipitation with ammonium sulfate, PEG, antibodies, and the like; heat denaturation, followed by centrifugation; chromatography steps such as ion exchange, gel filtration, reverse phase, hydroxlyapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the peptides always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed, utilizing an HPLC apparatus, will generally result in a greater "-fold" purification than the same technique utilizing a low pressure chromatography system. Methods exhibiting a lower degree of relative purification may have advantages in total recovery of protein product, or in maintaining the activity of an expressed protein. Also it is contemplated that a combination of anion exchange and immunoaffinity chromatography may be employed to produce purified peptide compositions of the present invention.

Pharmaceutical Compositions

The present invention also relates to pharmaceutical compositions comprising a therapeutically or prophylactically effective amount of at least AFP-6, AFP-6 agonist or AFP-6 analog of the invention, or a pharmaceutically acceptable salt thereof, together with pharmaceutically acceptable diluents, preservatives, solubilizers, emulsifiers, adjuvants and/or carriers useful in the delivery of AFP-6, AFP-6 agonist or AFP-6 analog. Such compositions may include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., thimersol, benzyl alcohol), and bulking substances (e.g., lactose, mannitol); incorporation of the material into particulate preparations of polymeric compounds, such as polylactic acid, polyglycolic acid, etc., or in association with liposomes. Such compositions will influence the physical state, stability, rate of in vivo release, and rate of in vivo clearance of the present AFP-6 analog. See, e.g., Remington's Pharmaceutical Sciences 1435-712, 18th ed., Mack Publishing Co., Easton, Pa. (1990). Exemplary methods for formulating pharmaceutical compositions can be found in WO 2004/048547, the entire contents of which are incorporated by reference.

As used herein, the phrase "pharmaceutically acceptable" refers to an agent that does not interfere with the effectiveness of the biological activity of an active ingredient, and which may be approved by a regulatory agency of the Federal government or a state government, or is listed in the U.S. Pharmacopeia or other generally recognized pharmacopeia for use in animals, and more particularly for use in humans. Accordingly, suitable pharmaceutically acceptable carriers include agents that do not interfere with the effectiveness of a pharmaceutical composition or produce an adverse, allergic or other untoward reaction when administered to an animal or a human.

As used herein, the phrase "pharmaceutically acceptable salts" refers to salts prepared from pharmaceutically acceptable, preferably nontoxic, acids and bases, including inorganic and organic acids and bases, including but not limited to, sulfuric, citric, maleic, acetic, oxalic, hydrochloride, hydro bromide, hydro iodide, nitrate, sulfate, bisulfite, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Pharmaceutically acceptable salts include those formed with free amino groups such as, but not limited to, those derived from hydrochloric, phosphoric, acetic, oxalic, and tartaric acids. Pharmaceutically acceptable salts also include those formed with free carboxyl groups such as, but not limited to, those derived from sodium, potassium, ammonium, sodium lithium, calcium, ferric hydroxides, isopropylamine, triethylamine, 2-ethylamino ethanol, histidine, and procaine.

The present AFP-6, AFP-6 agonist or AFP-6 analog may be formulated for peripheral administration, including formulation for injection, oral administration, nasal administration, pulmonary administration, topical administration, or other types of administration as one skilled in the art will recognize. More particularly, administration of the pharmaceutical compositions according to the present invention may be via any common route so long as the target tissue is available via that route. In a preferred embodiment, the pharmaceutical compositions may be introduced into the subject by any conventional peripheral method, e.g., by intravenous, intradermal, intramusclar, intramammary, intraperitoneal, intrathecal, retrobulbar, intrapulmonary (e.g., term release); by oral, sublingual, nasal, anal, vaginal, or transdermal delivery, or by surgical implantation at a particular site. Examples include, intravenous or subcutaneous injection; nasal, oral or muscosal administration; and pulmonary inhalation by nose or mouth. The treatment may consist of a single dose or a plurality of doses over a period of time. Controlled continual release of the compositions of the present invention is also contemplated.

The pharmaceutical compositions suitable for injectable use include sterile aqueous solutions or dispersions and sterile powders for the extemporaneous preparation of sterile injectable solutions or dispersions. In all cases, the form should be sterile and should be fluid to the extent that is easily syringable. It is also desirable for the polypeptide of the invention to be stable under the conditions of manufacture and storage and must be preserved against the contaminating action of microorganisms, such as bacteria and fungi. The carrier can be a solvent or dispersion medium containing, for example, water, ethanol, polyol (e.g., sorbitol, glycerol, propylene glycol, and liquid polyethylene glycol, and the like), dimethylacetamide, cremorphor EL, suitable mixtures thereof, and oils (e.g., soybean, sesame, castor, cottonseed, ethyl oleate, isopropyl myristate, glycofurol, corn). The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, meta-cresol, benzyl alcohol, parabens (methyl, propyl, butyl), chlorobutanol, phenol, phenylmercuric salts (acetate, borate, nitrate), sorbic acid, thimerosal, and the like. In many cases, tonicity agents (for example, sugars, sodium chloride) will be included in the compositions. Prolonged absorption of the injectable compositions can be brought about by the use in the compositions of agents delaying absorption (for example, aluminum monostearate and gelatin).

In one embodiment, the pharmaceutical compositions of the present invention are formulated so as to be suitable for parenteral administration, e.g., via injection or infusion. In one embodiment, the AFP-6 analog is suspended in an aqueous carrier, for example, in an isotonic buffer solution at a pH of about 3.0 to about 8.0, in another embodiment at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. A form of repository or "depot" slow release preparation may be used so that therapeutically effective amounts of the preparation are delivered into the bloodstream over many hours or days following transdermal injection or delivery.

Generally, a therapeutically or prophylactically effective amount of the present AFP-6, AFP-6 agonist or AFP-6 analog will be determined by the age, weight, and condition or severity of the diseases or metabolic conditions or disorders of the recipient. See, e.g., Remington's Pharmaceutical Sciences 697-773. See also Wang and Hanson, Parenteral Formulations of Proteins and Peptides: Stability and Stabilizers, Journal of Parenteral Science and Technology, Technical Report No. 10, Supp. 42:2 S (1988). Typically, a dosage of between about 0.001 µg/kg body weight to about 1000 µg/kg body weight, may be used, but more or less, as a skilled practitioner will recognize, may be used. Dosing may be one or more times daily, or less frequently, and may be in conjunction with other compositions as described herein. It should be noted that the present invention is not limited to the dosages recited herein.

Appropriate dosages may be ascertained through the use of established assays for determining level of metabolic conditions or disorders in conjunction with relevant dose-response data. The final dosage regimen will be determined by the attending physician, considering factors that modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

An effective dose will typically be in the range of about 1 to 30 µg to about 5 mg/day, alternatively about 10 to 30 µg to about 2 mg/day and in additional embodiments from about 5 to 100 µg to about 1 mg/day, or about 5 µg to about 500 µg/day, for a 50 kg patient, administered in a single or divided doses or controlled continued release. Exemplary dosages are between about 0.01 to about 100 µg/kg/dose. Administration should begin whenever the suppression of nutrient availability, food intake, weight, blood glucose or plasma lipid lowering or blood pressure lowering or increasing is desired, for example, at the first sign of symptoms or shortly after diagnosis of obesity, diabetes mellitus, insulin-resistance syndrome, hypertension or hypotension. Administration may be by any route, e.g., injection (including subcutaneous or intramuscular), oral, nasal, transdermal, etc. Dosages for certain routes, for example oral administration, may be increased to account for decreased bioavailability, for example, by about 5-100 fold.

In one embodiment where the pharmaceutical formulation is to be administered parenterally, the composition may be formulated so as to deliver a dose of AFP-6, AFP-6 agonist, or AFP-6 analog ranging from 0.01 µg/kg to 100 mg/kg body weight/day, or at a range of about 0.01 µg/kg to about 500 µg/kg per dose, about 0.05 µg/kg to about 250 µg/kg or below about 50 µg/kg. Another exemplary dose range is from 0.1 mg/kg to about 50 mg/kg body weight/day. Dosages in these ranges will vary with the potency of each analog or derivative, of course, and may be determined by one of skill in the art. Exemplary body weights contemplated in for the dosing regimen can be about 40, 50, 60, 70, 80, 90, or 100 kg or more. Parenteral administration may be carried out with an initial bolus followed by continuous infusion to maintain therapeutic circulating levels of drug product. Those of ordinary skill in the art can readily optimize effective dosages and administration regimens as determined by good medical practice and the clinical condition of the individual patient.

In the methods of the present invention, the polypeptides may be administered separately or together with one or more other compounds and compositions that exhibit a long term or short-term action or complementary action, i.e., combination therapy. For example, an additional compound may be added to AFP-6, AFP-6 agonist or AFP-6 analog that also reduces nutrient availability, such compounds include, but are not limited to an amylin or amylin analog agonist, salmon calcitonin, a cholecystokinin (CCK) or CCK agonist, a leptin (OB protein) or leptin agonist, an exendin or exendin agonist or analog agonist, or a GLP-1 or GLP-1 agonist or analog agonist or a PYY or PYY agonist or analog, or a PYY related polypeptide. Suitable amylin agonists include, for example, $[^{25,28,29}\text{Pro}]$-human amylin (also known as "pramlintide," and described in U.S. Pat. Nos. 5,686,511 and 5,998,367). The CCK used is, for example, CCK octapeptide (CCK-8). Leptin is discussed, for example, in Pelleymounter et al. (1995) *Science* 269:540-543, Halaas et al. (1995) *Science* 269:543-546, and Campfield et al. (1995) *Science* 269:546-549. Suitable exendins include exendin-3 and exendin-4, and exendin agonist compounds including, for example, those described in PCT Publications WO 99/07404, WO 99/25727, and WO 99/25728. Suitable PYY polypeptides and analogs include those described in U.S. Application Nos. 60/543,406 and 60/543,407, PCT publications WO 03/026591 and WO 03/057235.

It will be appreciated that the pharmaceutical compositions and treatment methods of the invention maybe useful in fields of human medicine and veterinary medicine. Thus, the subject to be treated may be a mammal, for example a human or other animals. For veterinary purposes, subjects include for example, farm animals including cows, sheep, pigs, horses and goats, companion animals such as dogs and cats, exotic and/or zoo animals, laboratory animals including mice, rats, rabbits, guinea pigs and hamsters; and poultry such as chickens, turkeys, ducks and geese.

In addition, the present invention contemplates a kit comprising AFP-6, AFP-6 agonist or AFP-6 analog, components suitable for preparing said compounds for pharmaceutical application, instructions for using said compounds and components for pharmaceutical application.

To assist in understanding the present invention, the following Examples are included. The experiments relating to this invention should not be construed as specifically limiting the invention and such variations of the invention, now known or later developed, which would be within the purview of one skilled in the art are considered to fall within the scope of the invention as described herein and hereinafter claimed.

EXAMPLES

The present invention is described in more detail with reference to the following non-limiting examples, which are offered to more fully illustrate the invention, but are not to be construed as limiting the scope thereof. The examples illustrate the preparation of the AFP-6 analogs (which includes derivatives) and the testing of these AFP-6 analogs in vitro and/or in vivo. Those of skill in the art will understand that the techniques described in these examples are only representative techniques described by the inventors that function in the practice of the invention. It should be appreciated that those of skill in the art should, in light of the present disclosure, appreciate that many changes can be made in the specific methods that are disclosed and still obtain a like or similar result without departing from the spirit and scope of the invention.

Example 1

AFP-6 Nucleic Acid Molecules and Polypeptides

1A. Identification of AFP-6 in Mouse and Human

A BlastP was performed with human adrenomedullin (SwissProt Accession Number P35318), restricting the search to mouse proteins and all other parameters set to default, to find the mouse homolog to human adrenomedullin. The top two sequences returned by the BlastP search were mouse adrenomedullin from Genbank and from SwissProt, the fourth sequence was CGRPII (CGRPI was #8 on the hits list). Unexpectedly, the third sequence on the list was hypothetical protein XP_147916. The match to the query sequence adrenomedullin (SEQ ID NO:43) spanned almost exactly the region of the adrenomedullin mature peptide (SEQ ID NO:44) and is shown in FIG. 1A.

The homology in the matched region is 44% with 32% identity as shown in FIG. 1B. Alignment of the mouse sequence (SEQ ID NO:45) with human adrenomedullin precursor (SEQ ID NO:46) shows that the homology across the entire protein is 25% (15% identity; all alignments performed with the AlignX® program (Vector NTI® Advance suite, purchased from Invitrogen Inc., Carlsbad, Calif.).

Two signal sequence detection programs, SignalP and PSort, were used to determine if this putative protein contained a cleavable signal. Both programs predicted a signal peptide cleaving between residues 25 and 26. The EST used to support the Refseq entity XP_147916 was BG918210.1 and had been cloned from mouse virgin mammary gland, infiltrating ductal carcinoma. The sequence of the entire protein XP_147916 (hereinafter referred to as mouse Amylin Family Polypeptide-6 or mAFP-6 precursor) in FASTA format is shown in FIG. 2 and is designated SEQ ID NO:45.

NCBI Blink is an automatically generated Blast available for most Genbank entries that indicates likely relationships to other proteins. The mAFP-6 precursor showed no matches at all. A BlastP search (limited to metazoa), however, performed with mAFP-6 precursor showed homology to mAFP-6 precursor itself, and, with much lower scores, to adrenomedullin from a variety of species (best expect score for this group was e=0.59). This BlastP, therefore, did not show any hits to a human ortholog although the apparent paralog, adrenomedullin itself, was detected in a variety of species.

To investigate if the XMI147916 transcript might encode another ORF with a closer homology to another protein, a BlastX was performed. BlastX translates a query sequence in 6 frames and compares it to a protein database. A match was detected to a human hypothetical protein FLJ21135, but not in the frame of the mouse transcript encoding the Amylin Family Polypeptide-6 sequence.

However, in silico translation of the transcripts AK024788 and NM_024866 encoding the hypothetical protein FLJ21135 showed that they also contain an upstream ORF that does match XP_147916. A longer transcript, AK090635, also contains an upstream ORF that matches XP_147916. The sequence surrounding the start codon of the upstream ORF is a better match to the Kozak consensus than is the sequence around the annotated start Met, compare: CCG CCC GCC ATG G (SEQ ID NO: 47) to CTC TCC GGG ATG G (SEQ ID NO: 48) (Classic Kozak is GCC GCC PuCC ATG G (SEQ ID NO: 49) (Kozak (1987) *J. Mol. Biol.* 196:947 and Kozak (1987) *Nucl. Acids Res.* 15:8125). This adrenomedullin-like ORF of AK024788 shows 67% similarity and 62% identity overall to mAFP-6 precursor. Hereinafter, the human predicted protein will be referred to as hAFP-6 precursor. The in silico translations of transcripts AK024788 and NM_024866 are designated herein hAFP-6 short precursor (SEQ ID NO:51) and the in silico translation of AK090635, which contains an insertion is designated hAFP-6 long (SEQ ID NO:50). An alignment of mouse and human AFP-6 precursor is shown in FIG. 3.

Alignment of human adrenomedullin precursor with the hAFP-6, NM_024866 ORF, shows that they have 26% similarity and 16% identity overall. However, they have greater homology over the region of the AFP-6 predicted peptide: 39% similarity and 32% identity. Alignment between human adrenomedullin precursor (SEQ ID NO:46) and hAFP-6 short form (NM24866/FLJ21135) (SEQ ID NO:51) is shown in FIG. 4.

BLAT (BLAT—The BLAST-Like Alignment Tool. Kent (2002) *Genome Res.* 12:656-664) analysis of these sequences against the human genome as assembled by the International Human Genome Sequencing Consortium (http://genome.ucsc.edu/), the UCSC genome bioinformatics website, indicates that hAFP-6 precursor is located on human chromosome 22, at 22q13. A Unigene entry exists matching hAFP-6 precursor and interestingly the SAGE data from the Unigene Contig Hs. 196985 shows the highest virtual score is for SAGE Pane 91 16113 pancreas epithelium ductal adenocarcinoma non-normalized bulk EST.

Adrenomedullin is part of the Amylin/Calcitonin/CGRP peptide family. Comparison to other members of this extended peptide family is shown in FIG. 5. Human AFP-6 has 27% identity to human amylin peptide, 25% identity to human CGRP peptide and 24% identity to human calcitonin peptide.

AFP-6 precursor is likely to encode a bona fide peptide hormone, with homologs at least in mouse and man. Based on the expected use of dibasic and monobasic sites for cleavage of mature peptides, and with guidance from the homology with adrenomedullin, the likely mature bioactive peptides are shown in FIG. 6.

1B. Cloning of Mouse and Human AFP-6 cDNAs

A 646 bp portion of the mouse AFP-6 cDNA containing the relevant open reading frame, was cloned by designing oligonucleotides to the database sequence XM147916 described above. These oligonucleotides (forward oligo 5'-AGC TTT GCC AGC TGT CTC CAG AT-3' (SEQ ID NO:52) and reverse oligo 5'-GGT ATC CAA AGC CAC GAG GAA TG-3' (SEQ ID NO:53)) were used to amplify this sequence from both mouse lung cDNA and 7-day embryo cDNA reverse transcribed at 42° C. using oligo dT as the primer from RNA purchased from BD Biosciences Clontech. The sequence was confirmed using ABI Big Dye Terminator cycle sequencing run on the ABI PRISM 310 Genetic Analyzer, demonstrating the existence of this transcript in the mouse embryo and lung. This sequence was then used as a probe to determine which other mouse tissues contain this transcript via northern analysis (described below).

An 886 bp portion of the human AFP-6 cDNA, containing only the 3' end of the relevant open reading frame, was cloned by designing oligos (forward oligo 5'-CCG ACC TGT GGT CTG GAA GCT T-3' (SEQ ID NO:54) and reverse oligo 5'-ATC CAG GTG GAG TCT CCA TGG C-3' (SEQ ID NO:55)) to the database sequence NM024866 described above. This sequence was amplified from human pancreas cDNA made from RNA obtained from BD Biosciences Clontech, which was reverse transcribed at 65° C. using Thermoscript reverse transcriptase (Invitrogen, Carlsbad, Calif.) with oligo dT as the primer. The hAFP-6 sequence was confirmed using ABI Big Dye Terminator cycle sequencing run on the ABI PRISM 310 Genetic Analyzer. Although clones obtained from this experiment did not contain the entire reading frame of interest, this sequence was used as a probe for northern blots to determine which other human tissues contain this transcript. It was also discovered that all four clones obtained from pancreas cDNA (which came from 15 male/female donors) corresponded to sequence that translates to the AFP-6 long form of the protein (shown in the alignment in FIG. 3).

An approximately 1.6 kb portion of the human AFP-6 cDNA containing the entire open reading frame of interest plus a large amount of 3' untranslated sequence was cloned from human prostate cDNA made with a high temperature reverse transcription enzyme (Thermoscript from Invitrogen). This was necessary due to the CpG island at the 5' end of this gene. The amplification was performed using the Advantage-GC kit (Clontech) to enhance recovery of GC rich sequences that tend to be difficult to amplify due to secondary structure. In the 5' untranslated regions (UTR) of three clones recovered from this experiment, there is a 72 bp sequence deletion relative to NM_024866 (between nucleotides 209 and 281 in FIG. 7) that may represent an alternatively spliced intron, or an intron inappropriately retained in the NM_024866 clone. A potential 5' donor site, GT, and 3' acceptor site, AG, are shown in gray in FIG. 7.

1C. Expression Analysis

Northern analysis from mouse and human: The 646 bp mouse insert and the 886 partial human cDNA clone insert were isolated, labeled with 32PdCTP and used to probe northern blots to determine which tissues express AFP-6 mRNA. Data is summarized in Table 4.

TABLE 4

| Tissue/Transcript | Mouse 1.6 kb | Mouse 1.2 kb | Human 4.7 kb | Human 1.8 kb |
|---|---|---|---|---|
| Adrenal Cortex | n.d. | n.d. | − | − |
| Adrenal Medulla | n.d. | n.d. | − | − |
| Brain | − | − | + | − |
| Cervix | n.d. | n.d. | − | − |
| Colon | n.d. | n.d. | ++ | − |
| Heart | − | − | n.d. | n.d. |
| Ileum | n.d. | n.d. | +++ | − |
| Jejunum | n.d. | n.d. | +++ | + |
| Kidney | +++ | +++ | ++ | + |
| Large Intestine | − | − | n.d. | n.d. |
| Liver | − | + | n.d. | n.d. |
| Lung** | − | − | ++ | − |
| Pancreas | n.d. | n.d. | ++++ | − |
| Placenta | n.d. | n.d. | + | − |
| Prostate | − | +++ | ++++ | − |
| Rectum | n.d. | n.d. | ++ | − |
| Salivary Gland | − | ++++ | ++++ | − |
| Skeletal Muscle | − | − | n.d. | n.d. |
| Small Intestine* | n.d. | n.d. | −/+ | −/+ |
| Spleen | − | − | − | − |
| Stomach | − | ++ | ++++/++ | +/− |
| Testis | − | − | − | − |
| Thyroid | − | ++ | ++++ | + |

TABLE 4-continued

| Tissue/Transcript | Mouse 1.6 kb | Mouse 1.2 kb | Human 4.7 kb | Human 1.8 kb |
|---|---|---|---|---|
| Thymus | − | − | − | − |
| Uterus | − | − | − | − |
| 7-day embryo | ++++ | − | n.d. | n.d. |
| 11-day embryo | − | − | n.d. | n.d. |
| 15-day embryo | − | − | n.d. | n.d. |
| 17-day embro | − | + | n.d. | n.d. | n.d. = not determined
+ = very weak expression (after more than 3 week exposure)
++ = weak expression (best seen after 3-5 day exposure)
+++ = mid level expression
++++ = strong expression
*No signal was seen in small intestine on the Clontech blot (BD Biosciences/Clontech, San Jose, CA), while the sections of the small intestine (ileum and jejunum) came up positive on the BioChain blot (BioChain, Hayward, CA). This may be due to amounts of poly A+ RNA on the blot (3 μg for Biochain vs 2 μg for Clontech)
**Although there was no signal for AFP-6 in mouse lung, it is possible to RT-PCR the cDNA from this tissue.

In human tissues, the major band expressed in the prostate, salivary gland, pancreas, thyroid, stomach, jejunum, ileum, and colon is larger than expected (about 4.7 kb rather than 2.6 kb for AK090635, which is the largest cDNA in the public database). The smaller band seen in the thyroid lane on the Clontech blot was calculated to be approximately 1.8 kb, similar in size to NM_024866, which is about 1.7 kb. Thus, there appears to be two forms of the AFP-6 transcript. Tissues that express AFP-6 weakly, requiring long exposures, were brain, lung, rectum, placenta and kidney. Tissues that did not express AFP-6 from this analysis were spleen, cervix, uterus, adrenal medulla, adrenal cortex, testis, and thymus. There was no signal on the Clontech endocrine blot from small intestine, but there is a signal on the BioChain blot for both jejunum and ileum. This is most likely due to different amounts of RNA on the blots, as previously discussed.

In tissues obtained from mice, the embryonic northern (from Clontech) revealed a 1.64 kb transcript expressed at 7 days, whereas a 1.28 kb transcript appeared at 17 days. Neither form was present at day 11 or 13. The 1.28 kb band was a little larger than expected as the Genbank sequence (XM_147916) is 765 bp. The difference in size may be due to several factors such as an expanded 5' or 3' UTR or a very long poly A tail. The hybridization conditions used reveal at least two different-sized transcripts that were identified with this probe. The larger transcript may represent a possible alternative splice.

Tissues with the strongest expression on the mouse adult blot were prostate and salivary gland, while from the human blots, prostate, salivary gland, pancreas, thyroid, stomach and intestine were the strongest. Weak expression on the mouse adult blot was thyroid and stomach. The pancreas was not analyzed by northern in mouse tissue; however, a dot blot in mouse tissue showed a positive signal for AFP-6, but this does not indicate which form is present in the pancreas. Tissues that did not express AFP-6 on this adult mouse northern blot were large intestine, thymus and uterus.

A second mouse northern was hybridized with the mouse AFP-6 probe. AFP-6 appeared to be present in kidney and perhaps at a very low level in liver. It was not detected in heart, brain, spleen, lung, skeletal muscle, or testis on this blot. Kidney expressed both forms of AFP-6 identified in the mouse (above). Previously, the larger form was only found in early embryogenesis (day 7 embryo). Size analysis confirms that the two bands found in the kidney corresponded to the larger embryonic form and the smaller adult form discussed above. There also appeared to be two forms of AFP-6 in the human, but the size difference between the two forms is much greater than is found in the mouse.

In situ analysis of mouse tissues. The same mouse AFP-6 probe described for the Northern analysis was used for in situ hybridization of mouse tissue sections to determine which cells in these tissues express the AFP-6 mRNA. Tissues were fixed in 4% paraformaldehyde in phosphate buffered saline (PBS) overnight, dehydrated and infiltrated with paraffin. 5 to 7 micron serial sections were mounted on gelatinized slides. One to three sections were mounted per slide, deparaffinized in xylene, re-hydrated, and post-fixed. The sections were digested with proteinase K, post-fixed, treated with triethanolamine/acetic anhydride, washed and dehydrated. The cRNA transcripts were synthesized according to manufacturer's conditions (Maxiscript Kit (T7) Ambion Inc., Austin, Tex.) and labelled with $^{35}$S-UTP (>1000 Ci/mmol; Amersham Biosciences, Piscataway, N.J.). cRNA transcripts larger than 200 nucleotides were subjected to alkali hydrolysis to give a mean size of 70 bases for efficient hybridization. Sections were hybridized overnight at 52° C. in 50% deionized formamide, 0.3 M NaCl, 20 mM Tris-HCl pH 7.4, 5 mM EDTA, 10 mM NaPO$_4$, 10% dextran sulfate, IX Denhardt's, 50 µg/ml total yeast RNA, and 50-75,000 cpm/µl $^{35}$S-labelled cRNA probe. The tissue was subjected to stringent washing at 65° C. in 50% formamide, 2×SSC, 10 mM DTT and washed in PBS before treatment with 20 µg/ml RNAse A at 37° C. for 30 minutes. Following washes in 2×SSC and 0.1×SSC for 10 minutes at 37° C., the slides were dehydrated and dipped in Kodak NTB-2 nuclear track emulsion and exposed for one week in light-tight boxes with dessicant at 4° C. Photographic development was carried out in Kodak D-19. Slides were counterstained lightly with toluidine blue and analyzed using both light- and darkfield optics of a Zeiss Axiophot microscope. Sense control cRNA probes (identical to the mRNAs) always gave background levels of hybridization signal.

Results indicate that in the mouse embryo at stages E9.5 and E12.5, days of embryonic development, the mRNA was widespread with uniform expression in all structures. At E17.5, the mRNA was still expressed widely, but expression was slightly higher in salivary gland, kidney and intestine. In the adult, AFP-6 mRNA was detected in Paneth cells in the crypts of Lieberkuhn of the small intestine, the gastric glands of the stomach epithelium, the acinar cells of the pancreas, the adenomeres of a salivary gland, the epithelium of the prostate, and the convoluted tubules of the kidney cortex. All of these cell types are secretory in nature. Representative pictures from pancreas, prostate and salivary gland are shown in FIGS. 8A-8I. The specific AFP-6 mRNA signal is seen in the Darkfield anti-sense images in the middle column.

Tissues analyzed in these experiments indicate that the AFP-6 mRNA for the peptide precursor has a tissue distribution pattern consistent with a secretory or exocrine function.

1D. Synthesis of AFP-6 Polypeptides

The following polypeptides can be synthesized using standard polypeptide synthesis methods. Such methods are described below and in U.S. Pat. Nos. 6,610,824 and 5,686,411 and in patent application Ser. No. 454,533 (filed Dec. 6, 1999), the entireties of which are incorporated herein by reference.

Polypeptides were synthesized on a Pioneer continuous flow peptide synthesizer (Applied Biosystems) using PAL-PEG-PS resin (Applied Biosystems) with a loading of 0.2 mmol/g (0.25 mmole scale). Fmoc amino acid (4.0 eq, 1.0 mmol) residues were activated using 4.0 eq HBTU, 4.0 eq of HOBT, 8.0 eq DIEA and coupled to the resin for 1 hour. The Fmoc group was removed by treatment with 20% (v/v) piperidine in dimethylformamide. Final deprotection and cleavage of the peptide from the solid support was performed by treatment of the resin with reagent B (93% TFA, 3% phenol, 3% water and 1% triisopropylsilane) for 2-3 hours. The cleaved peptide was precipitated using tert-butyl methyl ether, pelleted by centrifugation and lyophilized. The pellet was re-dissolved in water (10-15 mL), filtered and purified via reverse phase HPLC using a C-18 column and an acetonitrile/water gradient containing 0.1% TFA. The purified product was lyophilized and analyzed by ESI-LC/MS and analytical HPLC and were demonstrated to be pure (>98%). Mass results all agreed with calculated values.

Alternatively, peptides were assembled on a Symphony® peptide synthesizer (Protein Technologies, Inc., Woburn, Mass.) using Rink amide resin (Novabiochem, San Diego, Calif.) with a loading of 0.43-0.49 mmol/g at 0.050-0.100 mmol. Fmoc amino acid (Applied Biosystems, Inc. 5.0 eq, 0.250-0.500 mmol) residues were dissolved at a concentration of 0.10 M in 1-methyl-2-pyrrolidinone. All other reagents (HBTU, HOBT and N,N-diisopropylethylamine) were prepared as 0.55 M dimethylformamide solutions. The Fmoc protected amino acids were then coupled to the resin-bound amino acid using, HBTU (2.0 eq, 0.100-0.200 mmol), HOBT (1.8 eq, 0.090-0.18 mmol), N,N-diisopropylethylamine (2.4 eq, 0.120-0.240 mmol) for 2 hours. Following the last amino acid coupling, the peptide was deprotected using 20% (v/v) piperidine in dimethylformamide for 1 hour. Once peptide sequence is completed, the Symphony® peptide synthesizer is programmed to cleave the resin. Trifluoroacetic acid (TFA) cleavage of the peptide from resin was carried out using a reagent mixture composed of 93% TFA, 3% phenol, 3% water and 1% triisopropylsilane. The cleaved peptide was precipitated using tert-butyl methyl ether, pelleted by centifugation and lyophilized. The pellet was dissolved in acetic acid, lyophilized and then dissolved in water, filtered and purified via reverse phase HPLC using a C18 column and an acetonitrile/water gradient containing 0.1% TFA. Analytical HPLC was used to assess purity of peptide and identity was confirmed by LC/MS and MALDI-MS.

Example 2

Receptor Bioactivity Analysis

2A. Adrenomedullin-Like Activity of AFP-6 as Determined by cAMP Production in Human Umbilical Vein Endothelial Cells (HUVECs).

Since AFP-6 has the closest homology to adrenomedullin, AFP-6 was tested for bioactivity in HUVECs that contain the adrenomedullin receptor (Kato et. al. (1995) *Eur. J. Pharmacol.* 289:383-385) using the Perkin Elmer AlphaScreen™ assay for cyclic AMP using an optimum of 25-30,000 cells per well. The peptides tested were adrenomedullin, CGRP alpha, and AFP-6. Elevation of cAMP levels was not large for HUVEC compared to CHO cells. CHO cells were chosen as a negative control since they do not express the adrenomedullin receptor.

Figure 9:
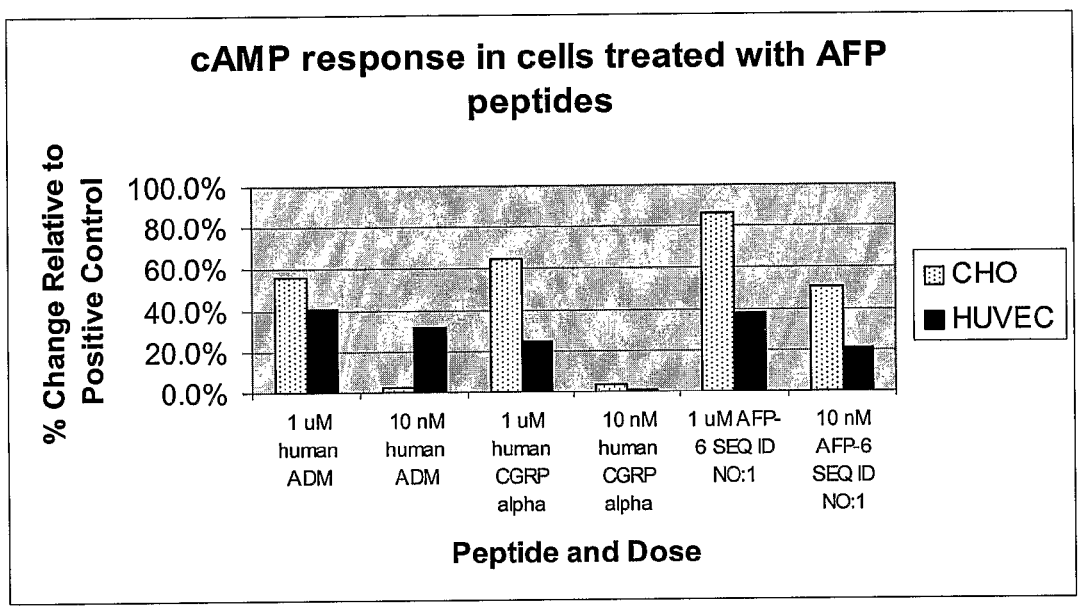
FIG. 9 shows data of elevation of cyclic AMP by AFP-6, hAdrenomedullin and hCGRP 1 at 2 concentrations in HUVEC and CHO cells as measured using the PerkinElmer AlphaScreen™ assay.

The results of the screen, shown in FIG. 9, demonstrate that AFP-6 was active in increasing cAMP levels at concentrations of 1 µM and 10 nM, but was less potent than adrenomedullin on HUVECs. Surprisingly, AFP-6 was more active on CHO cells, which do not contain an adrenomedullin receptor, than on HUVEC cells, which do contain the adrenomedullin receptor. The rank order of potency in HUVECs was as follows: adrenomedullin >AFP-6>>CGRP alpha. The rank order of potency in CHO cells was: AFP-6>adrenomedullin=CGRP alpha.

Thus, AFP-6 interacts with the adrenomedullin receptor but with lower affinity than adrenomedullin itself. Since AFP-6 appears more potent than adrenomedullin at increasing cAMP levels in CHO cells, this interaction is most likely through another receptor, for example the calcitonin receptor (D'Santos et. al. (1992) *Mol. Pharmacol.* 41:894-899).

2B. AFP-6 Peptide Functionally Interacts with the Calcitonin Receptor as Determined by cAMP Production in CHO Cells.

To test whether AFP-6 interacts with the calcitonin receptor, a panel of related peptides was retested in CHO cells and also in T47D cells, which also express the calcitonin receptor (Muff et al. (1992) *Ann. NY Acad. Sci.* 657:106-116 and Kuestner et. al. (1994) *Mol. Phamacol.* 46:246-255). In the CHO cell experiments, AFP-6 was similar in potency to amylin, and more potent than adrenomedullin with a rank order of potency of: calcitonin >AFP-6>amylin >hCGRP alpha>adrenomedullin. The $EC_{50}$ values for the compounds on CHO cells are shown in Table 7A below. The table summarizes $EC_{50}$ values calculated from dose response curves ranging from 1 pM to 1 μM of Amylin Family peptides on cell lines containing the calcitonin receptor, CHO cells (A) and T47D cells (B), respectively. Data from three exemplary independent alpha screen assays are summarized with $EC_{50}$ values calculated in PRISM.

ally by the olfactory tracts and extending at a 45° angle medially from these tracts. This basal forebrain tissue, containing the nucleus accumbens and surrounding regions, was weighed and homogenized in ice-cold 20 mM HEPES buffer (20 mM HEPES acid, pH adjusted to 7.4 with NaOH at 23° C.). Membranes were washed three times in fresh buffer by centrifugation for 15 minutes at 48,000.times.g. The final membrane pellet was resuspended in 20 mM HEPES buffer containing 0.2 mM phenylmethylsulfonyl fluoride (PMSF).

To measure $^{125}$I-amylin binding (see, Beaumont et al. (1995) *Can. J. Physiol. Pharmacol.* 73(7):1025-1029), membranes from 4 mg original wet weight of tissue were incubated with $^{125}$I-amylin at 12-16 μM in 20 mM HEPES buffer containing 0.5 mg/ml bacitracin, 0.5 mg/ml bovine serum albumin, and 0.2 mM PMSF. Solutions were incubated for 60 minutes at 2 C. Incubations were terminated by filtration through GF/B glass fiber filters (Whatman Inc., Clifton, N.J.) that had been presoaked for 4 hours in 0.3% poylethyleneimine in order to reduce nonspecific binding of radiolabeled peptides. Filters were washed immediately before filtration with 5 ml cold PBS, and immediately after filtration with 15 ml cold PBS. Filters were removed and radioactivity assessed in a gamma-counter at a counting efficiency of 77%. Competition curves were generated by measuring binding in the presence of $10^{-12}$ to $10^{-6}$ M unlabeled test compound and

TABLE 7A

| CHO (30,000 cells/well) + Compound | Experiment 1 $EC_{50}$ nM | Experiment 2 $EC_{50}$ nM | Experiment 3 $EC_{50}$ nM | Average $EC_{50}$ nM | SD |
|---|---|---|---|---|---|
| rAmylin | 21.6 | 30.9 | 19.6 | 24.03 | 6.03 |
| (hCalcitonin) | 0.077 | 0.14 | 0.075 | 0.097 | 0.03 |
| (Adrenomedullin) | 999 | 3600 | 622 | 1740.33 | 1621.51 |
| AFP-6 | 11.3 | 10.6 | 7 | 9.63 | 2.30 |
| (hCGRP) | 70.3 | 81.2 | 89.7 | 80.4 | 9.72 |

TABLE 7B

| T47D (7500 cells/well) + Compound | Experiment 1 $EC_{50}$ nM | Experiment 2 $EC_{50}$ nM | Experiment 3 $EC_{50}$ nM | Average $EC_{50}$ nM | SD |
|---|---|---|---|---|---|
| rAmylin | 0.72 | 5 | 2.3 | 2.67 | 2.16 |
| (hCalcitonin) | 0.001 | 0.029 | 0.014 | 0.014 | 0.01 |
| (Adrenomedullin) | 37.7 | 124 | 69.8 | 77.16 | 43.61 |
| AFP-6 | 10.4 | 20.7 | 9.5 | 13.53 | 6.22 |
| (hCGRP) | 11.9 | 66.7 | 27.8 | 35.46 | 28.19 |

AFP-6 also increased cAMP production in T47D cells. The $EC_{50}$ values for the compounds on T47D cells are shown in Table 7B above and establish a rank order of potency similar to that seen in CHO-K1 cells: calcitonin>amylin >AFP-6=hCGRP alpha>adrenomedullin. These data demonstrate that AFP-6 interacts with the calcitonin receptor, not as well as calcitonin itself, but with an affinity equivalent to that of amylin and much better than that of adrenomedullin.

2C: AFP-6 Interacts with the Amylin and CGRP Receptors as Determined by Radioligand Binding.

Evaluation of the binding of some exemplary compounds of the invention to amylin receptors was carried out as follows in nucleus accumbens membranes prepared from rat brain. $^{125}$I-rat amylin was Bolton-Hunter labeled from Amersham Corporation Arlington Heights, Ill.). Unlabeled peptides were obtained from BACHEM Inc. (Torrance, Calif.).

Male Sprague-Dawley® rats (200-250) grams were sacrificed by decapitation. Brains were removed and place in cold phosphate-buffered saline (PBS). From the ventral surface, cuts were made rostral to the hypothalamus, bounded later-were analyzed by nonlinear regression using a 4-parameter logistic equation (INPLOT program; GRAPHPAD Software, San Diego, Calif.).

Evaluation of the binding of compounds of the invention to CGRP receptors was essentially as described for amylin except using membranes prepared from SK-N-MC cells, known to express CGRP receptors (Muff, R. et. al. Ann NY Acad. Sci. 1992: 657, 106-16). Binding assays were performed as described for amylin except using 13,500 cpm 125I-hCGRP/well or 21.7 pM/well (Amersham).

Figure 10:
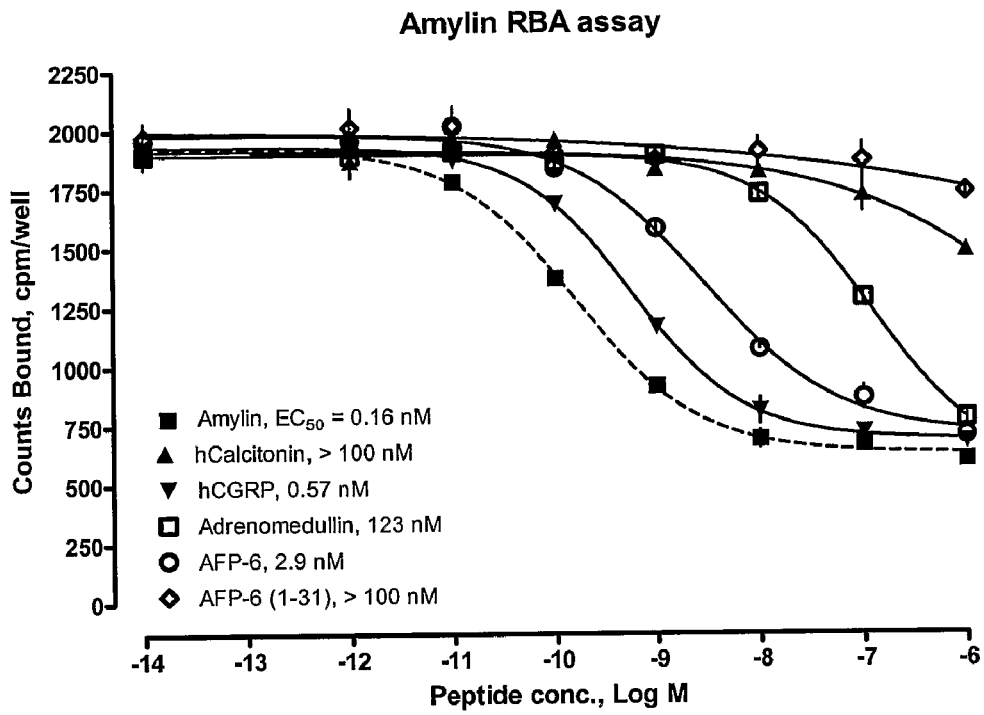
FIG. 10 shows results of an amylin radioligand binding assay (RBA). The graph depicts displacement of radiolabeled amylin binding with calculated inhibitory concentration ($IC_{50}$) values for AFP-6, hAdrenomedullin, hCGRP 1, hCalcitonin, and rAmylin at the amylin receptor.

IC50 values for the displacement of bound amylin shown in FIG. 10 establish a rank order of potency of: amylin >CGRP>AFP-6 >>adrenomedullin>calcitonin, showing that AFP-6 is a potent ligand at the amylin receptor, much more so than adrenomedullin, but not as potent as amylin itself.

Figure 11:
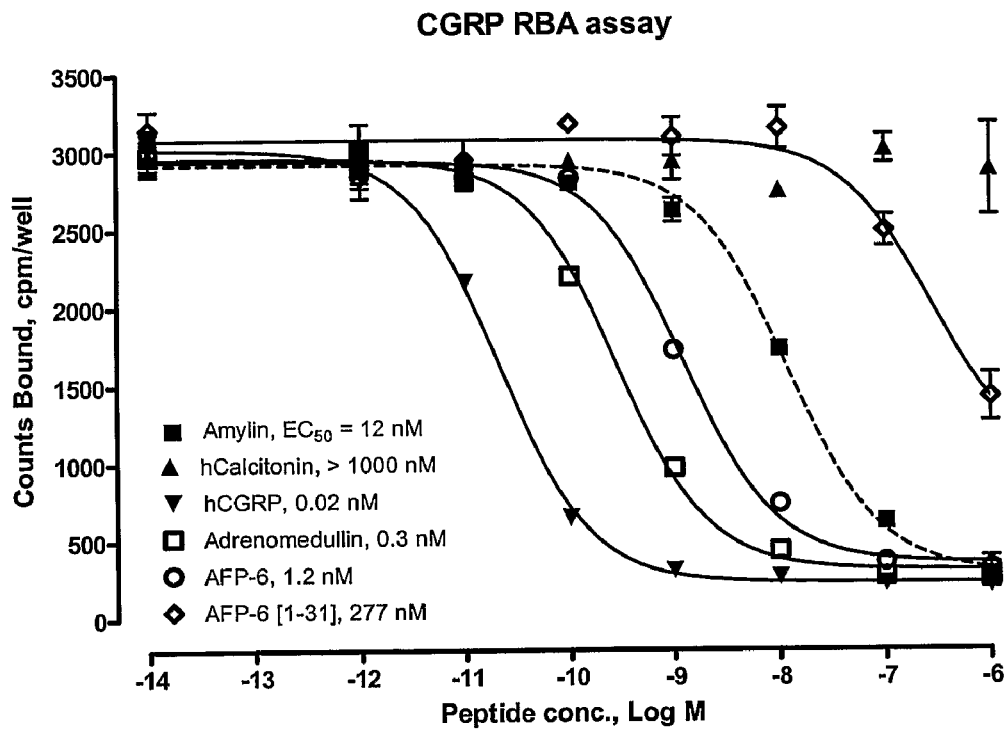
FIG. 11 shows results of a CGPR radioligand binding assay (RBA). The graph depicts displacement of radiolabeled CGRP binding with calculated $IC_{50}$ values for AFP-6, hAdrenomedullin, hCGRP 1, hCalcitonin, and rAmylin at the CGRP receptor.

Similarly, FIG. 11 shows IC50 values for the displacement of CGRP, with a rank order of: CGRP >adrenomedullin >AFP-6 >amylin>>calcitonin, showing that AFP-6 is a potent ligand at the CGRP receptor, but not as potent as CGRP itself or adrenomedullin.

Relative binding potencies of the Amylin Family of polypeptides are shown in Table 4. AFP-6 is a promiscuous ligand, having high potency at multiple receptors.

Example 3

Effects on Caloric Intake

The effect of AFP-6 on food intake was investigated using an acute food intake assay. This assay measured food consumption in lean, group-housed, overnight-fasted NIH/Swiss mice. 12 mice were housed 3 to a cage. The sample compound, in this case AFP-6, was injected IP in mice and food intake was measured during the next 2-hours. Decreased, as well as increased, food intake can be measured. Testing various doses of the compound generated ED50's. The assay was performed as follows: 1. Remove food (water ad libitum) at 5:00 pm the evening before the study. 2. Weigh food pellets (3 pellets/cage). 3. Inject animals intraperitoneally with 200 ul of appropriate solution, t=0. 4. Immediately add pre-weighed food to each cage (away from water bottle spout) and allow animals to feed undisturbed. 5. At 30, 60, and 120 minutes, collect and weigh food. 6. Analyze data. Data points represent mean ±sd of n=12.

Figure 12:
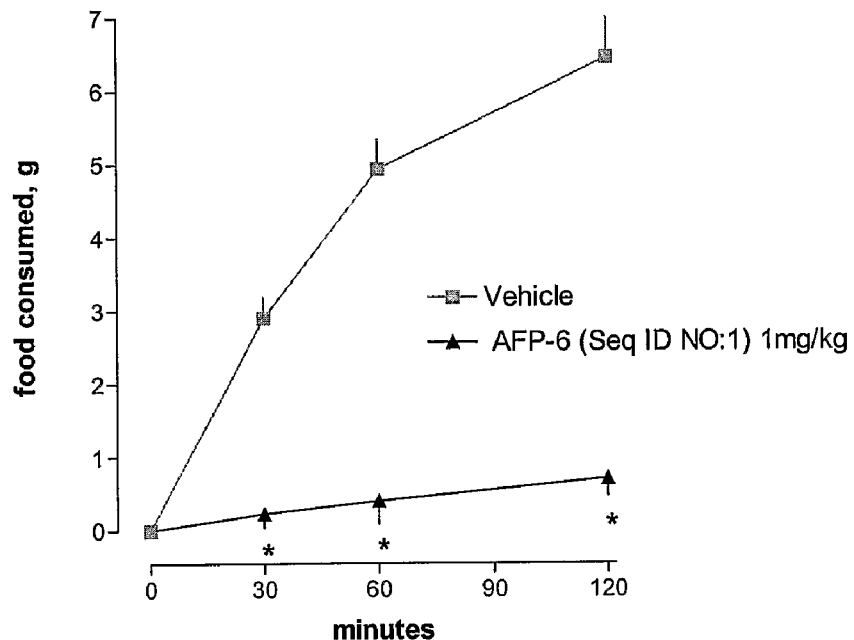
FIG. 12 shows the effect of AFP-6 on short-term food intake in mice.

In FIG. 12, AFP-6, at 1 mg/kg, is shown to inhibit food intake by 91%. Rat calcitonin at 0.63 mg/kg did not inhibit food intake significantly (16%). In contrast, rat amylin, with as little as 0.1 mg/kg, inhibited food intake by 30-40%. Adrenomedullin inhibited food intake up to 71%, with an $ED_{50}$ of 13 nmol/kg for this effect. Adrenomedullin, when administered intracerebroventricularly, does inhibit food intake in rats, but purportedly through activation of CGRP receptors (Taylor et. al. (1996) *Endocrinology* 137:3260-3264).

Thus, it appears that while AFP-6 can interact with the calcitonin receptor, it is not this pharmacological interaction which mediates the effects of AFP-6 on food intake, since calcitonin itself does not have an effect on food intake. Relative potencies of the Amylin Family of polypeptides are shown in Table 4. Whilst calcitonin is not effective at reducing food intake, AFP-6 is as effective as amylin, CGRP and adrenomedullin.

Figure 13:
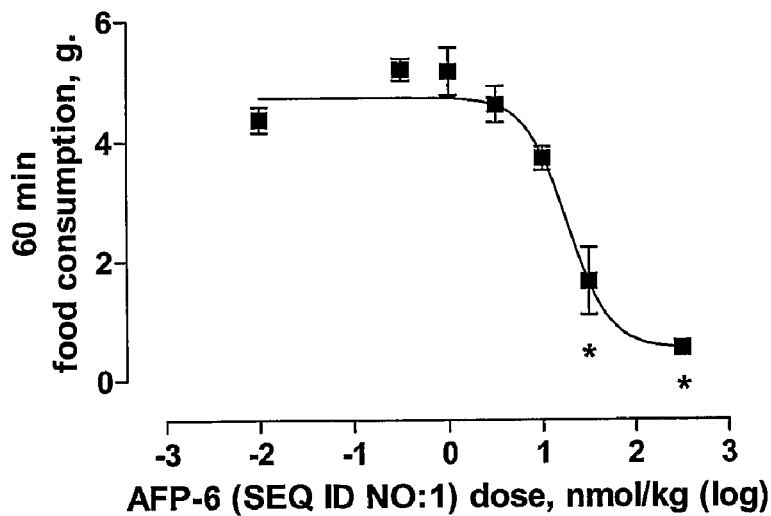
FIG. 13 shows a dose response of AFP-6 on short-term food intake in mice.

Following the above procedure, FIG. 13 shows a dose response of AFP-6 on short-term food intake. Twelve mice were injected IP at t=0 for each dose, 0.3, 1, 3, 10, 30, 100, or 300 nmol/kg of AFP-6 (Amylin Pharmaceuticals, Inc.) (n=12/group). Food was introduced immediately after injection and amount consumed measured at t=30, 60, and 120 min. From non-linear regression: ED50=19 nmol/kg at the 60 min time point.

Example 4

Activity of AFP-6 on Gastric Emptying Rate

Figure 14A:
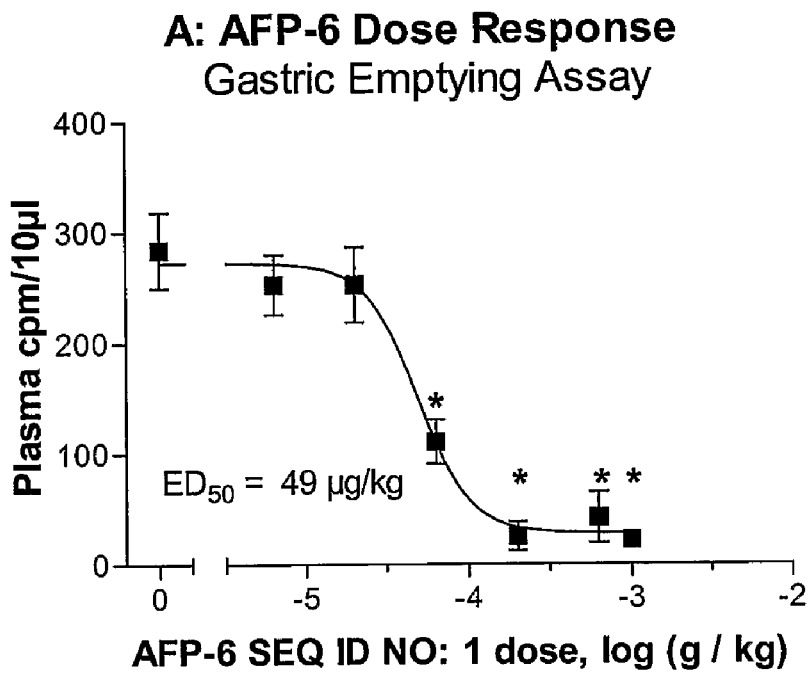
FIGS. 14A and 14B show the effect of AFP-6 and rAmylin, respectively, on the rate of gastric emptying in rats.
Figure 14B:
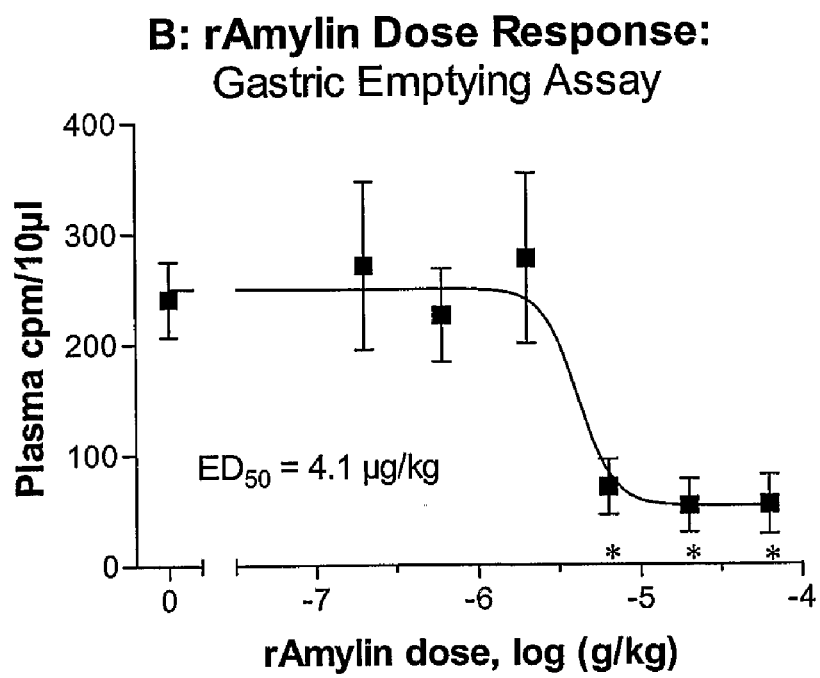

Male Harlan Sprague Dawley® rats, 237-317 g, were housed with a 12:12 hour light:dark cycle. The experiment was carried out during the light cycle. At time=0 min, test peptide (amylin or AFP-6) at 6.3, 20, 63, 200, 632, and 1122 µg/kg or vehicle was injected (subcutaneous) into conscious rats (n=6/group). At t=5 min, a solution of 1 mL sterile water containing 5 µCi D-[3-$^3$H] glucose was gavaged by oropharyngeal tube to conscious rats. Blood samples were collected 30 min after gavage and assayed for counts per minute (CPM) in plasma. 20% benzocaine liquid topical anesthetic was used to eliminate pain during sampling. (Gedulin et al. (1995) *Gastroenterology* 108:A604). The appearance of counts in plasma is a reflection of the rate of gastric emptying. Significance of difference (p<0.05) was determined by ANOVA. As can be seen in FIG. 14A, AFP-6 inhibits gastric emptying with an $ED_{50}$ of 49 µg/kg. FIG. 14B shows that rat amylin also inhibits gastric emptying, decreasing the appearance of counts in plasma, with an $ED_{50}$ of 4 µg/kg.

Example 5

Activity of AFP-6 on Total Plasma Calcium

Figure 15A:
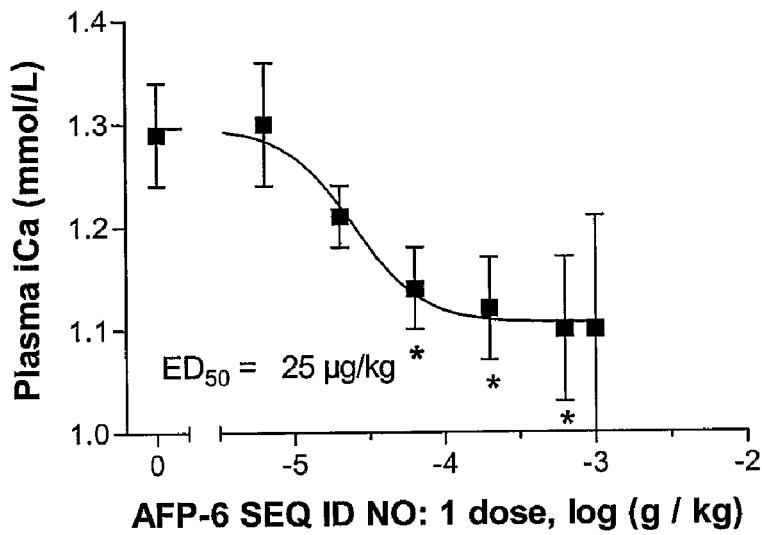
FIGS. 15A and 15B show the effect of AFP-6 and rAmylin, respectively, on plasma ionized calcium levels in rats.
Figure 15B:
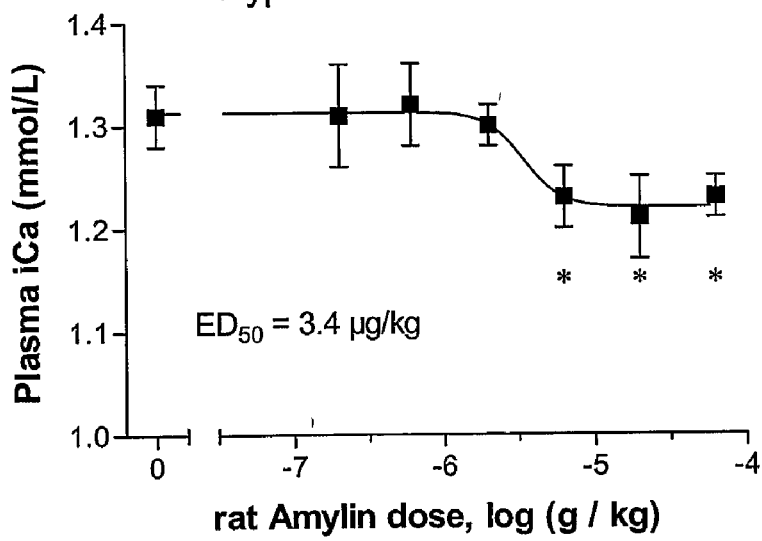

Using the samples obtained from Example 4, ionized calcium was measured in plasma samples obtained from gastric emptying experiments described above, using an ion selective electrode, Ciba/Corning 634 Ca/pH analyzer (Ciba/Corning, Inc., Medfield, Mass.). FIGS. 15A and B show that, like amylin, AFP-6 also decreases plasma ionized calcium with an $ED_{50}$ of 25 µg/kg.

Example 6

Chemical Characterization and Activity of Some AFP-6 Analogs

6A: Chemical Characterization of Some Exemplary AFP-6 Analogs.

The purified analogs, synthesized according to the procedures described in Example ID were analyzed by ESI-LC/MS and analytical HPLC and were demonstrated to be pure (>98%). Mass results all agreed with calculated values and are shown in Table 5.

6B: Effects of Some AFP-6 analogs on Receptor Binding Activity and Food Intake.

Some exemplary AFP-6 analogs were tested for receptor bioactivity and food intake, essentially as described in Examples 2 and 3. Results are shown in Tables 5 and 6, food intake and receptor binding, respectively.

TABLE 5

AFP-6 Polypeptide analogs: Food Intake data and analytical data

| SEQ ID NO: | Sequence | FI Inhibition (%) | MS [M + H] + Calcd | MS [M + H] + Found |
|---|---|---|---|---|
| 1 | TQAQLLRVGCVLGTCQVQNLSHRLW QLMGPAGRQDSAPVDPSSPHSY-NH2 | −42.5 | 5100.78 | 5100.9 |
| 2 | VGCVLGTCQVQNLSHRLWQLMGPAG RQDSAPVDPSSPHSY-NH2 | −47 | 4289.83 | 4290.2 |
| 10 | RVGCVLGTCQVQNLSHRLWQLMGPA GRQDSAPVDPSSPHSY-NH2 | −35 | 4446.02 | 4447.4 |

TABLE 5-continued

AFP-6 Polypeptide analogs: Food Intake data and analytical data

| SEQ ID NO: | Sequence | FI Inhibition (%) | MS [M + H]+ Calcd | MS [M + H]+ Found |
|---|---|---|---|---|
| 11 | GCVLGTCQVQNLSHRLWQLMGPAGRQDSAPVDPSSPHSY-NH2 | −40 | 4190.1 | 4190.9 |
| 12 | CVLGTCQVQNLSHRLWQLMGPAGRQDSAPVDPSSPHSY-NH2 | −41 | 4133.65 | 4134.5 |
| 16 | TQAQLLRVGCVLGTCQVQNLSHRLWQLRQDSAPVDPSSPHSY-NH2 | −35 | 4687.28 | 4686.4 |
| 17 | TQAQLLRVGCVLGTCQVQNLSHRLWQLDSAPVDPSSPHSY-NH2 | −17 | 4402.97 | 4402.4 |
| 18 | VGCVLGTCQVQNLSHRLWQLRQDSAPVDPSSPHSY-NH2 | −33 | 3876.34 | 3878.65 |
| 19 | CVLGTCQVQNLSHRLWQLRQESAPVEPSSPHSY-NH2 | −27 | 3748.21 | 3750.0 |
| 20 | TQAQLLRVGCSNLSTCQVQNLSHRLWQLMGPAGRQDSAPVDPSSPHSY- | −23 | 5232.86 | 5234.9 |
| 21 | TQAQLLRVGCNTATCQVQNLSHRLWQLMGPAGRQDSAPVDPSSPHSY-NH2 | −41 | 5117.8 | 5118.25 |
| 22 | RVGCGNLSTCQVQNLSHRLWQLMGPAGRQDSAPVDPSSPHSY-NH2 | −37 | 4550.08 | 4550.4 |
| 27 | VGMVLGTMQVQNLSHRLWQLRQDSAPVDPSSPHSY-NH2 | −12 | 3934.46 | 3934.5 |
| 28 | RVGCGNLSTCQVQNLSHRLWQLMGPAGRQDSAPVDPSSPHSY-NH2 | −37 | 4550.08 | 4550.4 |
| 29 | VGCGNLSTCQVQNLSHRLWQLRQDSAPVDPSSPHSY-NH2 | −13 | 3978.38 | 3979.05 |
| 30 | VCNTATCQVQNLSHRLWQLRQDSAPVDPSSPHSY-NH2 | −26.5 | 3836.23 | 3837.05 |
| 31 | GCNTATCQVQNLSHRLWQLRQDSAPVDPSSPHSY-NH2 | −18 | 3794.15 | 3794.05 |
| 32 | TQAQLLRVGCVLGTCQVQNLSHRLWQLMGPAGRQESAPVEPSSPHSY-NH2 | −33 | 5128.83 | 5130.25 |
| 35 | VGCVLGTCQVQNLSHRLWQLMGPAGRQDSAPVEPSSPHSY-NH2 | −35.5 | 4303.86 | 4305.4 |
| 36 | VGCVLGTCQVQNLSHRLWQLRQDSAPVEPSSPHSY-NH2 | −17 | 3890.36 | 3809.75 |
| 37 | GCNTATCQVQNLSHRLWQLRQDSAPVEPSSPHSY-NH2 | −12 | 3808.17 | 3809.75 |
| 39 | GCGNLSTCQVQNLSHRLWQLRQDSAPVEPSSPHSY-NH2 | −10 | 3893.28 | 3893.7 |
| 40 | GCVLGTCQVQNLSHRLWQLRQESAPVEPSSPHSY-NH2 | −12 | 3805.26 | 3806.7 |

TABLE 6

AFP-6 Polypeptide analogs: Receptor Binding data

| SEQ ID | Sequence | Amylin (nM) | CGRP (nM) | CT (nM) | ADM (nM) |
|---|---|---|---|---|---|
| 1 | TQAQLLRVGCVLGTCQVQNLSHRLWQLMGPAGRQDSAPVDPSSPHSY-NH2 | 13 | 3 | 32 | 19.9 |
| 2 | VGCVLGTGQVQNLSHRLWQLMGPAGRQDSAPVDPSSPHSY-NH2 | 12 | 1 | 24 | 6.4 |

TABLE 6-continued

AFP-6 Polypeptide analogs:
Receptor Binding data

| SEQ ID | Sequence | Amylin (nM) | CGRP (nM) | CT (nM) | ADM (nM) |
|---|---|---|---|---|---|
| 10 | RVGCVLGTCQVQNLSHRLWQLMGPAGRQDSAPVDPSSPHSY-NH2 | 5.1 | 1.4 | 55 | 7.1 |
| 11 | GCVLGTCQVQNLSHRLWQLMGPAGRQDSAPVDPSSPHSY-NH2 | 7.7 | 0.93 | 27 | 11 |
| 12 | CVLGTCQVQNLSHRLWQLMGPAGRQDSAPVDPSSPHSY-NH2 | 9.8 | 2.2 | 198 | 18 |
| 14 | VQNLSHRLWQLMGPAGRQDSAPVDPSSPHSY-NH2 | >1000 | >1000 | >1000 | 59 |
| 16 | TQAQLLRVGCVLGTCQVQNLSHRLWQLRQDSAPVDPSSPHSY-NH2 | 21 | 1.5 | 22 | 1000 |
| 17 | TQAQLLRVGCVLGTCQVQNLSHRLWQLDSAPVDPSSPHSY-NH2 | 209 | 10.5 | >1000 | 304 |
| 18 | VGCVLGTCQVQNLSHRLWQLRQDSAPVDPSSPHSY-NH2 | 18 | 3.6 | 24 | 1000 |
| 19 | CVLGTCQVQNLSHRLWQLRQESAPVEPSSPHSY-NH2 | 29 | 12.7 | 247 | 1000 |
| 20 | TQAQLLRVGCSNLSTCQVQNLSHRLWQLMGPAGRQDSAPVDPSSPHSY-NH2 | 1.9 | 25 | 16 | 36 |
| 21 | TQAQLLRVGCNTATCQVQNLSHRLWQLMGPAGRQDSAPVDPSSPHSY-NH2 | 8.3 | 8.5 | 17 | 47 |
| 22 | RVGCGNLSTCQVQNLSHRLWQLMGPAGRQDSAPVDPSSPHSY-NH2 | 2.4 | 35 | 7.3 | 19 |
| 25 | TQAQLLRVGMVLGTMQVQNLSHRLWQLMGPAGRQDSAPVDPSSPHSY-NH2 | 139 | 80 | >1000 | 120 |
| 26 | GMVLGTMQVQNLSHRLWQLMGPAGRQDSAPVDPSSPHSY-NH2 | 48 | 26 | >1000 | 37 |
| 27 | VGMVLGTMQVQNLSHRLWQLRQDSAPVDPSSPHSY-NH2 | >1000 | >1000 | >1000 | 1000 |
| 28 | RVGCGNLSTCQVQNLSHRLWQLMGPAGRQDSAPVDPSSPHSY-NH2 | 2.4 | 35 | 7.3 | 19 |
| 29 | VGCGNLSTCQVQNLSHRLWQLRQDSAPVDPSSPHSY-NH2 | 7.5 | 111 | 9 | 1000 |
| 30 | VCNTATCQVQNLSHRLWQLRQDSAPVDPSSPHSY-NH2 | 19 | 37 | 128 | 1000 |
| 31 | GCNTATCQVQNLSHRLWQLRQDSAPVDPSSPHSY-NH2 | 12 | 18 | 51 | 1000 |
| 32 | TQAQLLRVGCVLGTCQVQNLSHRLWQLMGPAGRQESAPVEPSSPHSY-NH2 | 16 | 2.3 | 1000 | 7.1 |
| 35 | VGCVLGTCQVQNLSHRLWQLMGPAGRQDSAPVEPSSPHSY-NH2 | 17 | 4.7 | 153 | 37 |
| 36 | VGCVLGTCQVQNLSHRLWQLRQDSAPVEPSSPHSY-NH2 | 39 | 14 | 198 | 1000 |
| 37 | GCNTATCQVQNLSHRLWQLRQDSAPVEPSSPHSY-NH2 | 39 | 130 | 121 | 1000 |
| 38 | GCSNLSTCQVQNLSHRLWQLRQDSAPVEPSSPHSY-NH2 | 9.9 | 208 | 17 | n.d. |
| 39 | GCGNLSTCQVQNLSHRLWQLRQDSAPVEPSSPHSY-NH2 | 14 | >1000 | 31 | 1000 |
| 40 | GCVLGTCQVQNLSHRLWQLRQESAPVEPSSPHSY-NH2 | >1000 | >1000 | >1000 | 1000 |

Example 7

Effects of AFP-6 on the Cardiovascular System

Telemetry allows for real-time hemodynamic readings including arterial pressure, heart rate, arterial dP/dt, ECG (with waveform intervals) and core temperature via an implanted radio transmitter in conscious, non-anesthetized, unrestrained rats. The rats were injected with either saline, 10 nmol/kg rat amylin, 10 nmol/kg rat adrenomedullin, or 10 nmol/kg AFP-6 by remote intravenous dosing. Remote intravenous dosing is achieved through in-dwelling vascular access ports.

Figure 16A:
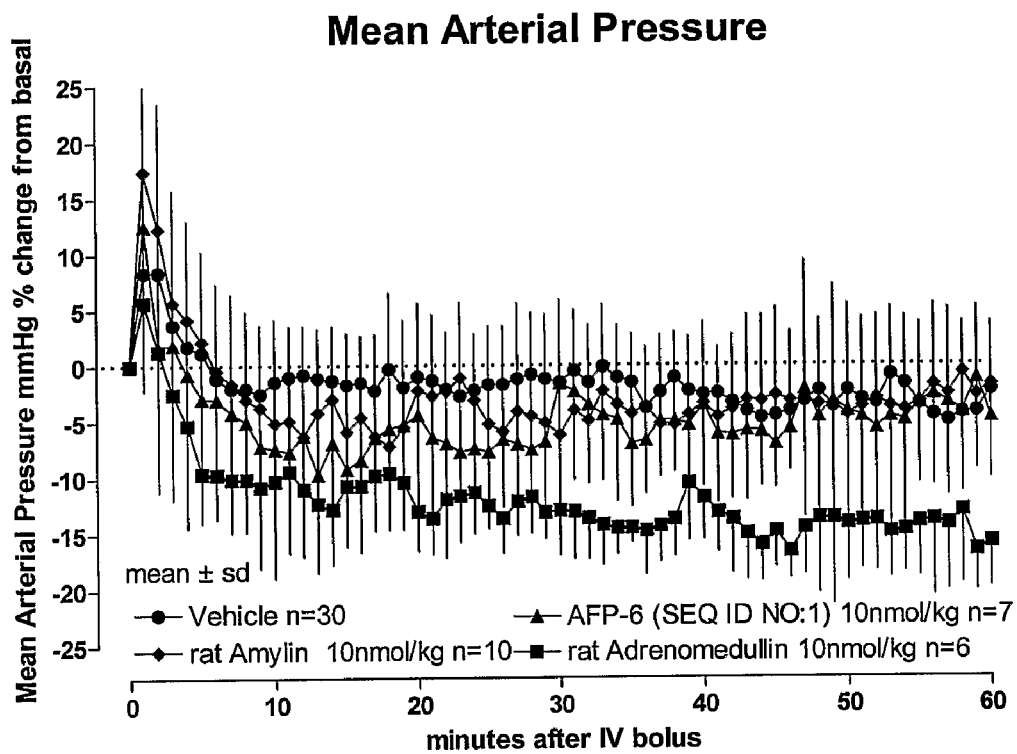
FIGS. 16A-16C show the effects of rAmylin, AFP-6, and rat adrenomedullin on several cardiac parameters, mean arterial pressure (MAP), heart rate (HR) and dp/dt, in male rats.
Figure 16B:
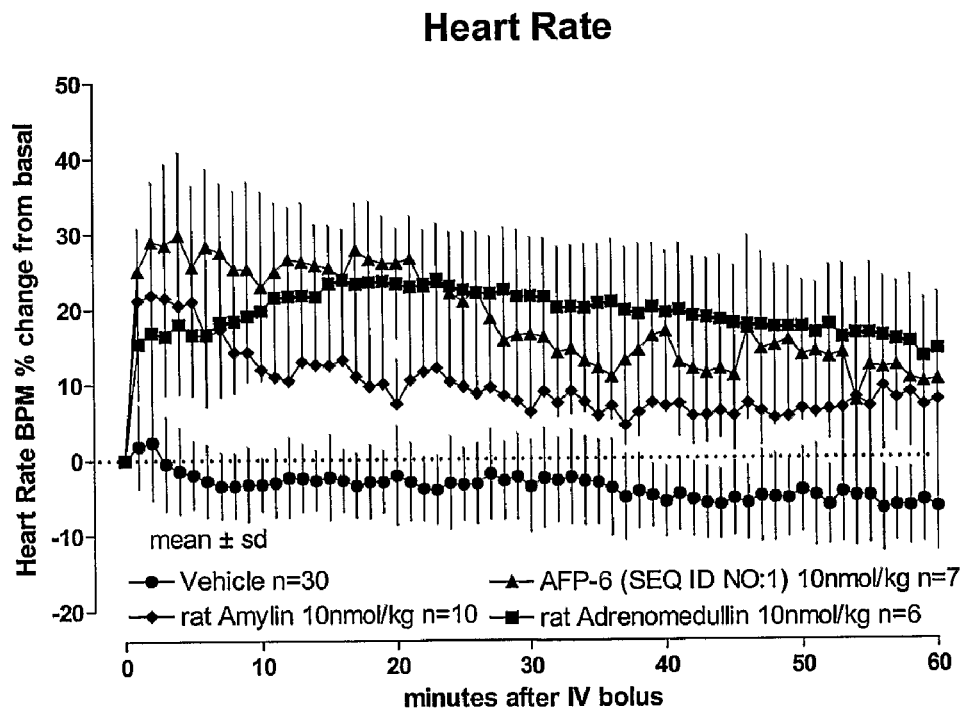
Figure 16C:
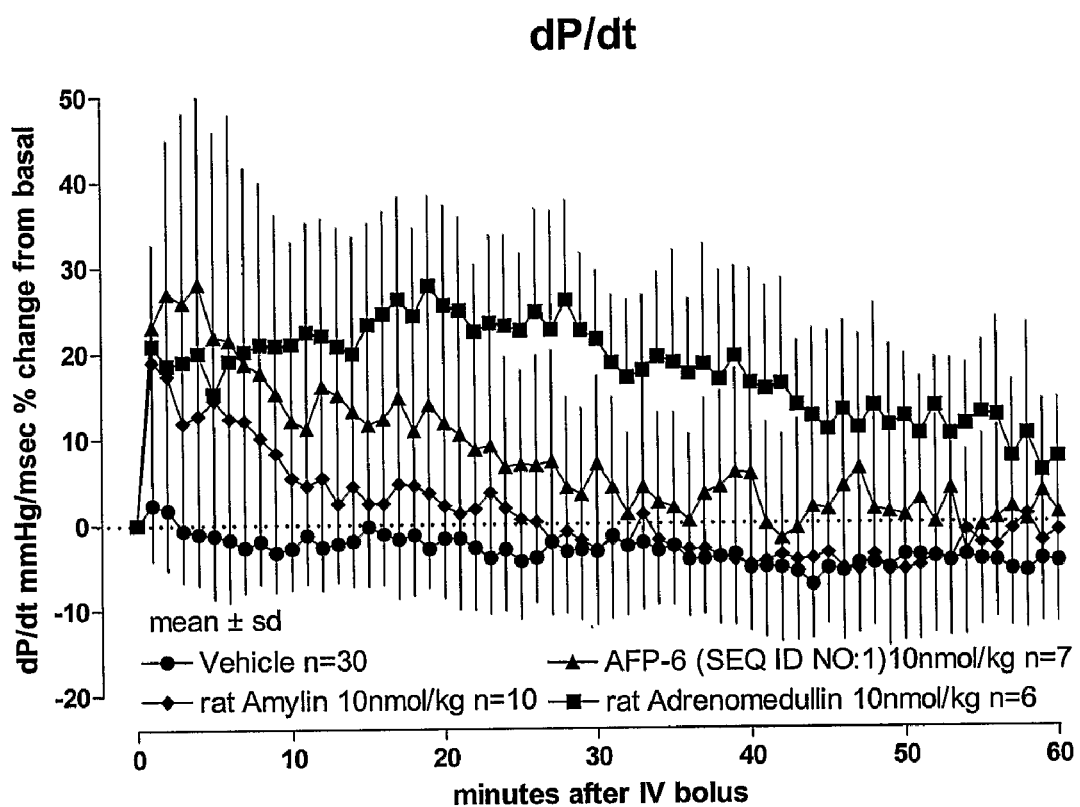

As shown in FIGS. 16 A-C, amylin increases mean arterial pressure (MAP) acutely and then may lower MAP in the first 30 minutes, while adrenomedullin decreases MAP throughout the 1-hour time period. For heart rate, all three peptides increase the number of beats per minute over the hour. Finally, amylin again acutely increases the dp/dt, but the effect tapers off over time, while adrenomedullin has a sustained increase in dp/dt over the hour. It appears that for all three cardiovascular parameters, AFP-6 has a profile more amylin-like than adrenomedullin like.

Example 8

Effects of AFP-6 on Food Intake and Body Weight in Rats

Individually housed male Sprague-Dawley® rats (beginning weight=310 g; 12-h light/dark cycle) were maintained on a high fat (HF) diet (Research Diet 58% kcal from fat). Rats were fattened for 34 days. At the end of the fattening period, 7-day osmotic pumps (Durect Corp.) were implanted interscapularly under anesthesia (body weight at time of implant=403 g). The rats received pumps delivering compound or vehicle (50% DMSO). The following compounds were examined at a 75 nmol/kg/day dose: AFP-6, and an AFP-6 analog SEQ ID NO:32. Food intake and body weight measurements were obtained on day 2 and day 7. Group differences were analyzed using analysis of variance (ANOVA) and Fisher's Least-Significant Difference test.

Figures 17A, 17B:
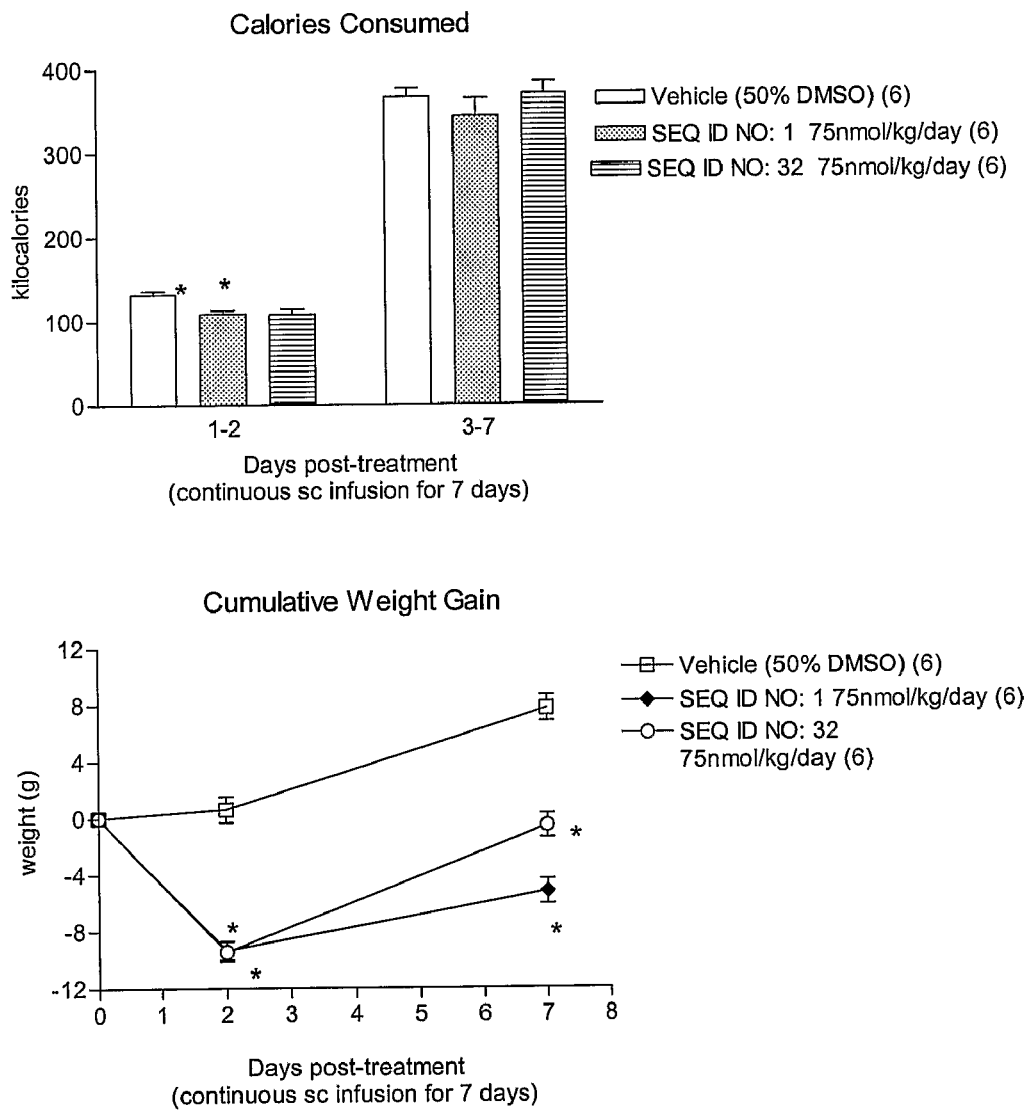
FIGS. 17A and 17B show the effect of 1-week continuous subcutaneous infusion of AFP-6, SEQ ID NO:1, or an exemplary analog of AFP-6, SEQ ID NO:32, on food intake and body weight gain in High Fat-Fed Rats.

FIGS. 17A and 17B show that both AFP-6 and the exemplary AFP-6 analog significantly reduced food intake compared to the Vehicle group after 2 days of treatment. By Day 7, food intake in both groups was equivalent to the Vehicle-treated group. Both peptides showed significantly less body weight gain than Vehicle on Day 7; the percent body weight loss on Day 7 for AFP-6 and the AFP-6 analog (vehicle-corrected) was 3.2% and 2.1%, respectively.

While the present invention has been described in terms of preferred examples and embodiments, it is understood that variations and modifications will occur to those skilled in the art. Therefore, it is intended that the appended claims cover all such equivalent variations that come within the scope of the invention as claimed.

What is claimed is:

1. An Amylin Family Polypeptide-6 (AFP-6) agonist analog having the amino acid sequence:

$X_1$-$X_2$-$X_3$-$X_4$-$X_5$-$X_6$-$X_7$-$X_8$-QVQNLSHRLWQL-$X_{21}$-$X_{22}$-$X_{23}$-$X_{24}$-$X_{25}$-$X_{26}$-$X_{27}$-$X_{28}$-SAPV-$X_{33}$-PSSPHSY (SEQ ID NO: 41)

wherein $X_1$ is absent, TQAQLLRVG (SEQ ID NO: 42), any of one or more consecutive amino acids of SEQ ID NO:42, N-aryl, or N-acyl with a substituent selected from a C1-C18 alkyl, a substituted alkyl or a heteroaryl moiety;

$X_2$ is M, S, C, substituted L, K, D or E, where the side chain can be linked via an amide bond, or any amino acid that can form a bond with $X_8$;

$X_3$ is V, D, L, G, N, A, or S;

$X_4$ is V, D, L, G, N, A, S or T;

$X_5$ is V, D, L, G, N, A, or S;

$X_6$ is V, D, L, G, N, A, S, or absent;

$X_7$ is T, S, homoserine, (S)-2-Amino-3-hydroxy-3-methylbutanoic acid (Ab) or (2R,3R)-2-Amino-3-hydroxy-4-methylpentanoic acid (Ap);

$X_8$ is M, S, C, substituted L, K, D or E, or any amino acid that can form a bond with $X_2$;

$X_{21}$ is M, G, P, A, or absent;

$X_{22}$ is M, G, P, A, or absent;

$X_{23}$ is M, G, P, A, or absent;

$X_{24}$ is M, G, P, A, or absent;

$X_{25}$ is M, G, P, A, or absent;

$X_{26}$ is R or absent, wherein when $X_{26}$ is absent, $X_{27}$ is absent;

$X_{27}$ is Q or absent, wherein when $X_{27}$ is absent, $X_{26}$ is absent;

$X_{28}$ is D or E;

$X_{33}$ is D or E;

wherein the amino acid sequence is not SEQ ID NO: 1 or SEQ ID NO: 2.

2. The AFP-6 agonist analog according to claim 1, comprising the amino acid sequence of any one of SEQ ID NOs: 10-12, 16-33 and 35-40.

3. The AFP-6 agonist analog according to claim 1 wherein the C-terminus is amidated.

4. A composition comprising at least one AFP-6 agonist analog according to claim 1 in a pharmaceutically acceptable carrier.

5. A method of treating or preventing a condition or disease that can be alleviated by reducing caloric or nutrient intake or availability in a subject in need thereof comprising administering to the subject an amount of an AFP-6 agonist analog according to claim 1 therapeutically effective to reduce caloric or nutrient intake or availability.

6. The method according to claim 5 wherein the condition or disease is obesity, insulin resistance, metabolic syndrome or diabetes mellitus.

7. The method according to claim 5 wherein the condition or disease is a cardiovascular condition or disease.

8. The AFP-6 agonist analog according to claim 2, wherein the amino acid sequence is SEQ ID NO:22.

9. The AFP-6 agonist analog according to claim 1, wherein $X_1$ is RVG.

10. An Amylin Family Polypeptide-6 (AFP-6) agonist analog comprising the amino acid sequence of SEQ ID NO:22.

11. A pharmaceutical composition comprising the AFP-6 agonist analog of claim 10.

12. A method for treating obesity, insulin resistance, metabolic syndrome, or diabetes mellitus in a patient in need thereof comprising administering a therapeutically effective amount of the AFP-6 agonist analog of claim 10 to the patient to treat obesity, insulin resistance, metabolic syndrome, or diabetes mellitus.

13. The method of claim 12, wherein the method is for treating obesity.

14. The method of claim 12, wherein the method is for treating diabetes mellitus.

15. The AFP-6 agonist analog according to claim 2, wherein the amino acid sequence is SEQ ID NO:21.

16. An Amylin Family Polypeptide-6 (AFP-6) agonist analog comprising the amino acid sequence of SEQ ID NO:21.

* * * * *

```
                        SEQUENCE LISTING

<160> NUMBER OF SEQ ID NOS: 58

<210> SEQ ID NO 1
<211> LENGTH: 47
<212> TYPE: PRT
<213> ORGANISM: Homo sapiens

<400> SEQUENCE: 1

Thr Gln Ala Gln Leu Leu Arg Val Gly Cys Val Leu Gly Thr Cys Gln
1               5                   10                  15

Val Gln Asn Leu Ser His Arg Leu Trp Gln Leu Met Gly Pro Ala Gly
            20                  25                  30

Arg Gln Asp Ser Ala Pro Val Asp Pro Ser Ser Pro His Ser Tyr
        35                  40                  45

<210> SEQ ID NO 2
<211> LENGTH: 40
<212> TYPE: PRT
<213> ORGANISM: Homo sapiens

<400> SEQUENCE: 2

Val Gly Cys Val Leu Gly Thr Cys Gln Val Gln Asn Leu Ser His Arg
1               5                   10                  15

Leu Trp Gln Leu Met Gly Pro Ala Gly Arg Gln Asp Ser Ala Pro Val
            20                  25                  30

Asp Pro Ser Ser Pro His Ser Tyr
        35                  40

<210> SEQ ID NO 3
<211> LENGTH: 47
<212> TYPE: PRT
<213> ORGANISM: Mus musculus

<400> SEQUENCE: 3

Pro His Ala Gln Leu Leu Arg Val Gly Cys Val Leu Gly Thr Cys Gln
1               5                   10                  15

Val Gln Asn Leu Ser His Arg Leu Trp Gln Leu Val Arg Pro Ala Gly
            20                  25                  30

Arg Arg Asp Ser Ala Pro Val Asp Pro Ser Ser Pro His Ser Tyr
        35                  40                  45

<210> SEQ ID NO 4
<211> LENGTH: 40
<212> TYPE: PRT
<213> ORGANISM: Mus musculus

<400> SEQUENCE: 4

Val Gly Cys Val Leu Gly Thr Cys Gln Val Gln Asn Leu Ser His Arg
1               5                   10                  15

Leu Trp Gln Leu Val Arg Pro Ala Gly Arg Arg Asp Ser Ala Pro Val
            20                  25                  30

Asp Pro Ser Ser Pro His Ser Tyr
        35                  40
```

```
<210> SEQ ID NO 5
<211> LENGTH: 37
<212> TYPE: PRT
<213> ORGANISM: Homo sapiens

<400> SEQUENCE: 5

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Thr Asn Val
            20                  25                  30

Gly Ser Asn Thr Tyr
        35

<210> SEQ ID NO 6
<211> LENGTH: 32
<212> TYPE: PRT
<213> ORGANISM: Homo sapiens

<400> SEQUENCE: 6

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 7
<211> LENGTH: 36
<212> TYPE: PRT
<213> ORGANISM: Homo sapiens

<400> SEQUENCE: 7

Ala Cys Asp Thr Ala Thr Cys Val Thr His Arg Leu Ala Gly Leu Leu
1               5                   10                  15

Ser Arg Ser Gly Gly Trp Lys Asn Asn Phe Val Pro Thr Asn Val Gly
            20                  25                  30

Ser Lys Ala Phe
        35

<210> SEQ ID NO 8
<211> LENGTH: 37
<212> TYPE: PRT
<213> ORGANISM: Homo sapiens

<400> SEQUENCE: 8

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ala Phe
        35

<210> SEQ ID NO 9
<211> LENGTH: 52
<212> TYPE: PRT
<213> ORGANISM: Homo sapiens

<400> SEQUENCE: 9

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30
```

Phe Thr Asp Lys Asp Lys Asp Asn Val Ala Pro Arg Ser Lys Ile Ser
            35                  40                  45

Pro Gln Gly Tyr
    50

<210> SEQ ID NO 10
<211> LENGTH: 41
<212> TYPE: PRT
<213> ORGANISM: Artificial Sequence
<220> FEATURE:
<223> OTHER INFORMATION: Synthetic amino acid sequence

<400> SEQUENCE: 10

Arg Val Gly Cys Val Leu Gly Thr Cys Gln Val Gln Asn Leu Ser His
1               5                   10                  15

Arg Leu Trp Gln Leu Met Gly Pro Ala Gly Arg Gln Asp Ser Ala Pro
            20                  25                  30

Val Asp Pro Ser Ser Pro His Ser Tyr
        35                  40

<210> SEQ ID NO 11
<211> LENGTH: 39
<212> TYPE: PRT
<213> ORGANISM: Artificial Sequence
<220> FEATURE:
<223> OTHER INFORMATION: Synthetic amino acid sequence

<400> SEQUENCE: 11

Gly Cys Val Leu Gly Thr Cys Gln Val Gln Asn Leu Ser His Arg Leu
1               5                   10                  15

Trp Gln Leu Met Gly Pro Ala Gly Arg Gln Asp Ser Ala Pro Val Asp
            20                  25                  30

Pro Ser Ser Pro His Ser Tyr
        35

<210> SEQ ID NO 12
<211> LENGTH: 38
<212> TYPE: PRT
<213> ORGANISM: Artificial Sequence
<220> FEATURE:
<223> OTHER INFORMATION: Synthetic amino acid sequence

<400> SEQUENCE: 12

Cys Val Leu Gly Thr Cys Gln Val Gln Asn Leu Ser His Arg Leu Trp
1               5                   10                  15

Gln Leu Met Gly Pro Ala Gly Arg Gln Asp Ser Ala Pro Val Asp Pro
            20                  25                  30

Ser Ser Pro His Ser Tyr
        35

<210> SEQ ID NO 13
<211> LENGTH: 32
<212> TYPE: PRT
<213> ORGANISM: Artificial Sequence
<220> FEATURE:
<223> OTHER INFORMATION: Synthetic amino acid sequence

<400> SEQUENCE: 13

Gln Val Gln Asn Leu Ser His Arg Leu Trp Gln Leu Met Gly Pro Ala
1               5                   10                  15

Gly Arg Gln Asp Ser Ala Pro Val Asp Pro Ser Ser Pro His Ser Tyr
            20                  25                  30

```
<210> SEQ ID NO 14
<211> LENGTH: 31
<212> TYPE: PRT
<213> ORGANISM: Artificial Sequence
<220> FEATURE:
<223> OTHER INFORMATION: Synthetic amino acid sequence

<400> SEQUENCE: 14

Val Gln Asn Leu Ser His Arg Leu Trp Gln Leu Met Gly Pro Ala Gly
1               5                   10                  15

Arg Gln Asp Ser Ala Pro Val Asp Pro Ser Ser Pro His Ser Tyr
            20                  25                  30

<210> SEQ ID NO 15
<211> LENGTH: 30
<212> TYPE: PRT
<213> ORGANISM: Artificial Sequence
<220> FEATURE:
<223> OTHER INFORMATION: Synthetic amino acid sequence

<400> SEQUENCE: 15

Val Gln Asn Leu Ser His Arg Leu Gln Leu Met Gly Pro Ala Gly Arg
1               5                   10                  15

Gln Asp Ser Ala Pro Val Asp Pro Ser Ser Pro His Ser Tyr
            20                  25                  30

<210> SEQ ID NO 16
<211> LENGTH: 42
<212> TYPE: PRT
<213> ORGANISM: Artificial Sequence
<220> FEATURE:
<223> OTHER INFORMATION: Synthetic amino acid sequence

<400> SEQUENCE: 16

Thr Gln Ala Gln Leu Leu Arg Val Gly Cys Val Leu Gly Thr Cys Gln
1               5                   10                  15

Val Gln Asn Leu Ser His Arg Leu Trp Gln Leu Arg Gln Asp Ser Ala
            20                  25                  30

Pro Val Asp Pro Ser Ser Pro His Ser Tyr
        35                  40

<210> SEQ ID NO 17
<211> LENGTH: 40
<212> TYPE: PRT
<213> ORGANISM: Artificial Sequence
<220> FEATURE:
<223> OTHER INFORMATION: Synthetic amino acid sequence

<400> SEQUENCE: 17

Thr Gln Ala Gln Leu Leu Arg Val Gly Cys Val Leu Gly Thr Cys Gln
1               5                   10                  15

Val Gln Asn Leu Ser His Arg Leu Trp Gln Leu Asp Ser Ala Pro Val
            20                  25                  30

Asp Pro Ser Ser Pro His Ser Tyr
        35                  40

<210> SEQ ID NO 18
<211> LENGTH: 35
<212> TYPE: PRT
<213> ORGANISM: Artificial Sequence
<220> FEATURE:
<223> OTHER INFORMATION: Synthetic amino acid sequence
```

-continued

```
<400> SEQUENCE: 18

Val Gly Cys Val Leu Gly Thr Cys Gln Val Gln Asn Leu Ser His Arg
1               5                   10                  15

Leu Trp Gln Leu Arg Gln Asp Ser Ala Pro Val Asp Pro Ser Ser Pro
            20                  25                  30

His Ser Tyr
        35

<210> SEQ ID NO 19
<211> LENGTH: 33
<212> TYPE: PRT
<213> ORGANISM: Artificial Sequence
<220> FEATURE:
<223> OTHER INFORMATION: Synthetic amino acid sequence

<400> SEQUENCE: 19

Cys Val Leu Gly Thr Cys Gln Val Gln Asn Leu Ser His Arg Leu Trp
1               5                   10                  15

Gln Leu Arg Gln Glu Ser Ala Pro Val Glu Pro Ser Ser Pro His Ser
            20                  25                  30

Tyr

<210> SEQ ID NO 20
<211> LENGTH: 48
<212> TYPE: PRT
<213> ORGANISM: Artificial Sequence
<220> FEATURE:
<223> OTHER INFORMATION: Synthetic amino acid sequence

<400> SEQUENCE: 20

Thr Gln Ala Gln Leu Leu Arg Val Gly Cys Ser Asn Leu Ser Thr Cys
1               5                   10                  15

Gln Val Gln Asn Leu Ser His Arg Leu Trp Gln Leu Met Gly Pro Ala
            20                  25                  30

Gly Arg Gln Asp Ser Ala Pro Val Asp Pro Ser Ser Pro His Ser Tyr
        35                  40                  45

<210> SEQ ID NO 21
<211> LENGTH: 47
<212> TYPE: PRT
<213> ORGANISM: Artificial Sequence
<220> FEATURE:
<223> OTHER INFORMATION: Synthetic amino acid sequence

<400> SEQUENCE: 21

Thr Gln Ala Gln Leu Leu Arg Val Gly Cys Asn Thr Ala Thr Cys Gln
1               5                   10                  15

Val Gln Asn Leu Ser His Arg Leu Trp Gln Leu Met Gly Pro Ala Gly
            20                  25                  30

Arg Gln Asp Ser Ala Pro Val Asp Pro Ser Ser Pro His Ser Tyr
        35                  40                  45

<210> SEQ ID NO 22
<211> LENGTH: 42
<212> TYPE: PRT
<213> ORGANISM: Artificial Sequence
<220> FEATURE:
<223> OTHER INFORMATION: Synthetic amino acid sequence
```

```
<400> SEQUENCE: 22

Arg Val Gly Cys Gly Asn Leu Ser Thr Cys Gln Val Gln Asn Leu Ser
1               5                   10                  15

His Arg Leu Trp Gln Leu Met Gly Pro Ala Gly Arg Gln Asp Ser Ala
            20                  25                  30

Pro Val Asp Pro Ser Ser Pro His Ser Tyr
        35                  40

<210> SEQ ID NO 23
<211> LENGTH: 47
<212> TYPE: PRT
<213> ORGANISM: Artificial Sequence
<220> FEATURE:
<223> OTHER INFORMATION: Synthetic amino acid sequence

<400> SEQUENCE: 23

Thr Gln Ala Gln Leu Leu Arg Val Gly Cys Asp Thr Ala Thr Cys Gln
1               5                   10                  15

Val Gln Asn Leu Ser His Arg Leu Trp Gln Leu Met Gly Pro Ala Gly
            20                  25                  30

Arg Gln Asp Ser Ala Pro Val Asp Pro Ser Ser Pro His Ser Tyr
        35                  40                  45

<210> SEQ ID NO 24
<211> LENGTH: 48
<212> TYPE: PRT
<213> ORGANISM: Artificial Sequence
<220> FEATURE:
<223> OTHER INFORMATION: Synthetic amino acid sequence

<400> SEQUENCE: 24

Thr Gln Ala Gln Leu Leu Arg Val Gly Cys Gly Asn Leu Ser Thr Cys
1               5                   10                  15

Gln Val Gln Asn Leu Ser His Arg Leu Trp Gln Leu Met Gly Pro Ala
            20                  25                  30

Gly Arg Gln Asp Ser Ala Pro Val Asp Pro Ser Ser Pro His Ser Tyr
        35                  40                  45

<210> SEQ ID NO 25
<211> LENGTH: 47
<212> TYPE: PRT
<213> ORGANISM: Artificial Sequence
<220> FEATURE:
<223> OTHER INFORMATION: Synthetic amino acid sequence

<400> SEQUENCE: 25

Thr Gln Ala Gln Leu Leu Arg Val Gly Met Val Leu Gly Thr Met Gln
1               5                   10                  15

Val Gln Asn Leu Ser His Arg Leu Trp Gln Leu Met Gly Pro Ala Gly
            20                  25                  30

Arg Gln Asp Ser Ala Pro Val Asp Pro Ser Ser Pro His Ser Tyr
        35                  40                  45

<210> SEQ ID NO 26
<211> LENGTH: 39
<212> TYPE: PRT
<213> ORGANISM: Artificial Sequence
<220> FEATURE:
<223> OTHER INFORMATION: Synthetic amino acid sequence
```

-continued

<400> SEQUENCE: 26

Gly Met Val Leu Gly Thr Met Gln Val Gln Asn Leu Ser His Arg Leu
1               5                   10                  15

Trp Gln Leu Met Gly Pro Ala Gly Arg Gln Asp Ser Ala Pro Val Asp
            20                  25                  30

Pro Ser Ser Pro His Ser Tyr
        35

<210> SEQ ID NO 27
<211> LENGTH: 35
<212> TYPE: PRT
<213> ORGANISM: Artificial Sequence
<220> FEATURE:
<223> OTHER INFORMATION: Synthetic amino acid sequence

<400> SEQUENCE: 27

Val Gly Met Val Leu Gly Thr Met Gln Val Gln Asn Leu Ser His Arg
1               5                   10                  15

Leu Trp Gln Leu Arg Gln Asp Ser Ala Pro Val Asp Pro Ser Ser Pro
            20                  25                  30

His Ser Tyr
        35

<210> SEQ ID NO 28
<211> LENGTH: 42
<212> TYPE: PRT
<213> ORGANISM: Artificial Sequence
<220> FEATURE:
<223> OTHER INFORMATION: Synthetic amino acid sequence

<400> SEQUENCE: 28

Arg Val Gly Cys Gly Asn Leu Ser Thr Cys Gln Val Gln Asn Leu Ser
1               5                   10                  15

His Arg Leu Trp Gln Leu Met Gly Pro Ala Gly Arg Gln Asp Ser Ala
            20                  25                  30

Pro Val Asp Pro Ser Ser Pro His Ser Tyr
        35                  40

<210> SEQ ID NO 29
<211> LENGTH: 36
<212> TYPE: PRT
<213> ORGANISM: Artificial Sequence
<220> FEATURE:
<223> OTHER INFORMATION: Synthetic amino acid sequence

<400> SEQUENCE: 29

Val Gly Cys Gly Asn Leu Ser Thr Cys Gln Val Gln Asn Leu Ser His
1               5                   10                  15

Arg Leu Trp Gln Leu Arg Gln Asp Ser Ala Pro Val Asp Pro Ser Ser
            20                  25                  30

Pro His Ser Tyr
        35

<210> SEQ ID NO 30
<211> LENGTH: 34
<212> TYPE: PRT
<213> ORGANISM: Artificial Sequence
<220> FEATURE:
<223> OTHER INFORMATION: Synthetic amino acid sequence -continued

```
<400> SEQUENCE: 30

Val Cys Asn Thr Ala Thr Cys Gln Val Gln Asn Leu Ser His Arg Leu
1               5                   10                  15

Trp Gln Leu Arg Gln Asp Ser Ala Pro Val Asp Pro Ser Pro His
            20                  25                  30

Ser Tyr

<210> SEQ ID NO 31
<211> LENGTH: 34
<212> TYPE: PRT
<213> ORGANISM: Artificial Sequence
<220> FEATURE:
<223> OTHER INFORMATION: Synthetic amino acid sequence

<400> SEQUENCE: 31

Gly Cys Asn Thr Ala Thr Cys Gln Val Gln Asn Leu Ser His Arg Leu
1               5                   10                  15

Trp Gln Leu Arg Gln Asp Ser Ala Pro Val Asp Pro Ser Ser Pro His
            20                  25                  30

Ser Tyr

<210> SEQ ID NO 32
<211> LENGTH: 47
<212> TYPE: PRT
<213> ORGANISM: Artificial Sequence
<220> FEATURE:
<223> OTHER INFORMATION: Synthetic amino acid sequence

<400> SEQUENCE: 32

Thr Gln Ala Gln Leu Leu Arg Val Gly Cys Val Leu Gly Thr Cys Gln
1               5                   10                  15

Val Gln Asn Leu Ser His Arg Leu Trp Gln Leu Met Gly Pro Ala Gly
            20                  25                  30

Arg Gln Glu Ser Ala Pro Val Glu Pro Ser Ser Pro His Ser Tyr
        35                  40                  45

<210> SEQ ID NO 33
<211> LENGTH: 47
<212> TYPE: PRT
<213> ORGANISM: Artificial Sequence
<220> FEATURE:
<223> OTHER INFORMATION: Synthetic amino acid sequence

<400> SEQUENCE: 33

Thr Gln Ala Gln Leu Leu Arg Val Gly Cys Val Leu Gly Thr Cys Gln
1               5                   10                  15

Val Gln Asn Leu Ser His Arg Leu Trp Gln Leu Met Gly Pro Ala Gly
            20                  25                  30

Arg Gln Asp Ser Ala Pro Val Glu Pro Ser Ser Pro His Ser Tyr
        35                  40                  45

<210> SEQ ID NO 34
<211> LENGTH: 30
<212> TYPE: PRT
<213> ORGANISM: Artificial Sequence
<220> FEATURE:
<223> OTHER INFORMATION: Synthetic amino acid sequence
```

-continued

<400> SEQUENCE: 34

Gly Thr Met Gln Val Gln Asn Leu Ser His Arg Leu Trp Gln Leu Arg
1               5                   10                  15

Gln Asp Ser Ala Pro Val Glu Pro Ser Ser Pro His Ser Tyr
            20                  25                  30

<210> SEQ ID NO 35
<211> LENGTH: 40
<212> TYPE: PRT
<213> ORGANISM: Artificial Sequence
<220> FEATURE:
<223> OTHER INFORMATION: Synthetic amino acid sequence

<400> SEQUENCE: 35

Val Gly Cys Val Leu Gly Thr Cys Gln Val Gln Asn Leu Ser His Arg
1               5                   10                  15

Leu Trp Gln Leu Met Gly Pro Ala Gly Arg Gln Asp Ser Ala Pro Val
            20                  25                  30

Glu Pro Ser Ser Pro His Ser Tyr
        35                  40

<210> SEQ ID NO 36
<211> LENGTH: 35
<212> TYPE: PRT
<213> ORGANISM: Artificial Sequence
<220> FEATURE:
<223> OTHER INFORMATION: Synthetic amino acid sequence

<400> SEQUENCE: 36

Val Gly Cys Val Leu Gly Thr Cys Gln Val Gln Asn Leu Ser His Arg
1               5                   10                  15

Leu Trp Gln Leu Arg Gln Asp Ser Ala Pro Val Glu Pro Ser Ser Pro
            20                  25                  30

His Ser Tyr
        35

<210> SEQ ID NO 37
<211> LENGTH: 34
<212> TYPE: PRT
<213> ORGANISM: Artificial Sequence
<220> FEATURE:
<223> OTHER INFORMATION: Synthetic amino acid sequence

<400> SEQUENCE: 37

Gly Cys Asn Thr Ala Thr Cys Gln Val Gln Asn Leu Ser His Arg Leu
1               5                   10                  15

Trp Gln Leu Arg Gln Asp Ser Ala Pro Val Glu Pro Ser Ser Pro His
            20                  25                  30

Ser Tyr

<210> SEQ ID NO 38
<211> LENGTH: 35
<212> TYPE: PRT
<213> ORGANISM: Artificial Sequence
<220> FEATURE:
<223> OTHER INFORMATION: Synthetic amino acid sequence -continued

```
<400> SEQUENCE: 38

Gly Cys Ser Asn Leu Ser Thr Cys Gln Val Gln Asn Leu Ser His Arg
1               5                   10                  15

Leu Trp Gln Leu Arg Gln Asp Ser Ala Pro Val Glu Pro Ser Ser Pro
            20                  25                  30

His Ser Tyr
        35

<210> SEQ ID NO 39
<211> LENGTH: 35
<212> TYPE: PRT
<213> ORGANISM: Artificial Sequence
<220> FEATURE:
<223> OTHER INFORMATION: Synthetic amino acid sequence

<400> SEQUENCE: 39

Gly Cys Gly Asn Leu Ser Thr Cys Gln Val Gln Asn Leu Ser His Arg
1               5                   10                  15

Leu Trp Gln Leu Arg Gln Asp Ser Ala Pro Val Glu Pro Ser Ser Pro
            20                  25                  30

His Ser Tyr
        35

<210> SEQ ID NO 40
<211> LENGTH: 34
<212> TYPE: PRT
<213> ORGANISM: Artificial Sequence
<220> FEATURE:
<223> OTHER INFORMATION: Synthetic amino acid sequence

<400> SEQUENCE: 40

Gly Cys Val Leu Gly Thr Cys Gln Val Gln Asn Leu Ser His Arg Leu
1               5                   10                  15

Trp Gln Leu Arg Gln Glu Ser Ala Pro Val Glu Pro Ser Ser Pro His
            20                  25                  30

Ser Tyr

<210> SEQ ID NO 41
<211> LENGTH: 40
<212> TYPE: PRT
<213> ORGANISM: Artificial Sequence
<220> FEATURE:
<223> OTHER INFORMATION: Synthetic amino acid sequence
<220> FEATURE:
<221> NAME/KEY: MISC_FEATURE
<222> LOCATION: (1)..(1)
<223> OTHER INFORMATION: absent, SEQIDNO:42, any of one or more
      consecutive amino acids of SEQIDNO:42, N-aryl, or N-acyl with a
      substituent selected from a C1-C18 alkyl, a substituted alkyl or a
      heteroaryl moiety
<220> FEATURE:
<221> NAME/KEY: MISC_FEATURE
<222> LOCATION: (2)..(2)
<223> OTHER INFORMATION: M, S, C, substituted L, K, D or E, where the
      side chain can be linked via an amide bond, or any amino acid that
      can form a bond with X at position 8
<220> FEATURE:
<221> NAME/KEY: MISC_FEATURE
<222> LOCATION: (3)..(3)
<223> OTHER INFORMATION: V, D, L, G, N, A, or S
<220> FEATURE:
<221> NAME/KEY: MISC_FEATURE
<222> LOCATION: (4)..(4)
<223> OTHER INFORMATION: V, D, L, G, N, A, S or T
<220> FEATURE:
<221> NAME/KEY: MISC_FEATURE
<222> LOCATION: (5)..(5)
<223> OTHER INFORMATION: V, D, L, G, N, A, or S
```

```
<220> FEATURE:
<221> NAME/KEY: MISC_FEATURE
<222> LOCATION: (6)..(6)
<223> OTHER INFORMATION: V, D, L, G, N, A, S, or absent
<220> FEATURE:
<221> NAME/KEY: MISC_FEATURE
<222> LOCATION: (7)..(7)
<223> OTHER INFORMATION: T, S, homoserine, (S)-2-Amino-3-hydroxy-3-
      methybutanoic acid, or (2R,3R)-2-Amino-3-hydroxy-4-methylpentanoic
      acid
<220> FEATURE:
<221> NAME/KEY: MISC_FEATURE
<222> LOCATION: (8)..(8)
<223> OTHER INFORMATION: M, S, C, substituted L, K, D or E, or any amino
      acid that can form a bond with X at position 2
<220> FEATURE:
<221> NAME/KEY: MISC_FEATURE
<222> LOCATION: (21)..(21)
<223> OTHER INFORMATION: M, G, P, A, or absent
<220> FEATURE:
<221> NAME/KEY: MISC_FEATURE
<222> LOCATION: (22)..(22)
<223> OTHER INFORMATION: M, G, P, A, or absent
<220> FEATURE:
<221> NAME/KEY: MISC_FEATURE
<222> LOCATION: (23)..(23)
<223> OTHER INFORMATION: M, G, P, A, or absent
<220> FEATURE:
<221> NAME/KEY: MISC_FEATURE
<222> LOCATION: (24)..(24)
<223> OTHER INFORMATION: M, G, P, A, or absent
<220> FEATURE:
<221> NAME/KEY: MISC_FEATURE
<222> LOCATION: (25)..(25)
<223> OTHER INFORMATION: M, G, P, A, or absent
<220> FEATURE:
<221> NAME/KEY: MISC_FEATURE
<222> LOCATION: (26)..(26)
<223> OTHER INFORMATION: R or absent; when absent, X at position 27 is
      absent
<220> FEATURE:
<221> NAME/KEY: MISC_FEATURE
<222> LOCATION: (27)..(27)
<223> OTHER INFORMATION: Q or absent; when absent, X at position 26 is
      absent
<220> FEATURE:
<221> NAME/KEY: MISC_FEATURE
<222> LOCATION: (28)..(28)
<223> OTHER INFORMATION: D or E
<220> FEATURE:
<221> NAME/KEY: MISC_FEATURE
<222> LOCATION: (33)..(33)
<223> OTHER INFORMATION: D or E

<400> SEQUENCE: 41

Xaa Xaa Xaa Xaa Xaa Xaa Xaa Xaa Gln Val Gln Asn Leu Ser His Arg
1               5                   10                  15

Leu Trp Gln Leu Xaa Xaa Xaa Xaa Xaa Xaa Xaa Xaa Ser Ala Pro Val
            20                  25                  30

Xaa Pro Ser Ser Pro His Ser Tyr
        35                  40

<210> SEQ ID NO 42
<211> LENGTH: 9
<212> TYPE: PRT
<213> ORGANISM: Artificial Sequence
<220> FEATURE:
<223> OTHER INFORMATION: Synthetic amino acid sequence

<400> SEQUENCE: 42

Thr Gln Ala Gln Leu Leu Arg Val Gly
1               5
```

```
<210> SEQ ID NO 43
<211> LENGTH: 73
<212> TYPE: PRT
<213> ORGANISM: Homo sapiens

<400> SEQUENCE: 43

Gly Ala Ser Arg Ser Pro Glu Asp Ser Ser Pro Asp Ala Ala Arg Ile
1               5                   10                  15

Arg Val Lys Arg Tyr Arg Gln Ser Met Asn Asn Phe Gln Gly Leu Arg
                20                  25                  30

Ser Phe Gly Cys Arg Phe Gly Thr Cys Thr Val Gln Lys Leu Ala His
            35                  40                  45

Gln Ile Tyr Gln Phe Thr Asp Lys Asp Lys Asp Asn Val Ala Pro Arg
    50                  55                  60

Ser Lys Ile Ser Pro Gln Gly Tyr Gly
65                  70

<210> SEQ ID NO 44
<211> LENGTH: 64
<212> TYPE: PRT
<213> ORGANISM: Mus musculus

<400> SEQUENCE: 44

Gly Gly Ser Arg His Pro Gly Pro Gln Arg Pro Thr Gly Ser Arg Arg
1               5                   10                  15

Pro His Ala Gln Leu Leu Arg Val Gly Cys Val Leu Gly Thr Cys Gln
                20                  25                  30

Val Gln Asn Leu Ser His Arg Leu Trp Gln Leu Val Arg Pro Ala Gly
            35                  40                  45

Arg Arg Asp Ser Ala Pro Val Asp Pro Ser Ser Pro His Ser Tyr Gly
    50                  55                  60

<210> SEQ ID NO 45
<211> LENGTH: 150
<212> TYPE: PRT
<213> ORGANISM: Mus musculus

<400> SEQUENCE: 45

Met Ala Gln Leu Leu Met Val Thr Val Thr Leu Gly Cys Ile Ser Leu
1               5                   10                  15

Leu Tyr Leu Leu Pro Gly Thr Leu Ser Gly Ser Leu Lys Gly Leu
                20                  25                  30

Arg His Ser Arg Pro Arg Glu Pro Pro Ala Lys Ile Pro Ser Ser Asn
            35                  40                  45

Leu Gln Pro Gly His Pro Ser Leu Gln Pro Val Val Trp Lys Ser Arg
    50                  55                  60

Arg His Ala Pro Gln Pro Gln Gly Arg Gly Asn Arg Ala Leu Ala Met
65                  70                  75                  80

Val His Leu Pro Gln Gly Gly Gly Ser Arg His Pro Gly Pro Gln Arg
                85                  90                  95

Pro Thr Gly Ser Arg Arg Pro His Ala Gln Leu Leu Arg Val Gly Cys
            100                 105                 110

Val Leu Gly Thr Cys Gln Val Gln Asn Leu Ser His Arg Leu Trp Gln
    115                 120                 125

Leu Val Arg Pro Ala Gly Arg Arg Asp Ser Ala Pro Val Asp Pro Ser
130                 135                 140

Ser Pro His Ser Tyr Gly
145                 150
```

```
<210> SEQ ID NO 46
<211> LENGTH: 185
<212> TYPE: PRT
<213> ORGANISM: Homo sapiens

<400> SEQUENCE: 46

Met Lys Leu Val Ser Val Ala Leu Met Tyr Leu Gly Ser Leu Ala Phe
1               5                   10                  15

Leu Gly Ala Asp Thr Ala Arg Leu Asp Val Ala Ser Glu Phe Arg Lys
            20                  25                  30

Lys Trp Asn Lys Trp Ala Leu Ser Arg Gly Lys Arg Glu Leu Arg Met
        35                  40                  45

Ser Ser Ser Tyr Pro Thr Gly Leu Ala Asp Val Lys Ala Gly Pro Ala
    50                  55                  60

Gln Thr Leu Ile Arg Pro Gln Asp Met Lys Gly Ala Ser Arg Ser Pro
65                  70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
        115                 120                 125

Asp Lys Asp Lys Asp Asn Val Ala Pro Arg Ser Lys Ile Ser Pro Gln
    130                 135                 140

Gly Tyr Gly Arg Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
            180                 185

<210> SEQ ID NO 47
<211> LENGTH: 13
<212> TYPE: DNA
<213> ORGANISM: Artificial Sequence
<220> FEATURE:
<223> OTHER INFORMATION: Synthetic construct

<400> SEQUENCE: 47
ccgcccgcca tgg                                                          13

<210> SEQ ID NO 48
<211> LENGTH: 13
<212> TYPE: DNA
<213> ORGANISM: Artificial Sequence
<220> FEATURE:
<223> OTHER INFORMATION: Synthetic construct

<400> SEQUENCE: 48
ctctccggga tgg                                                          13

<210> SEQ ID NO 49
<211> LENGTH: 13
<212> TYPE: DNA
<213> ORGANISM: Artificial Sequence
<220> FEATURE:
<223> OTHER INFORMATION: Synthetic construct

<400> SEQUENCE: 49
gccgccrcca tgg                                                          13
```

<210> SEQ ID NO 50
<211> LENGTH: 148
<212> TYPE: PRT
<213> ORGANISM: Homo sapiens

<400> SEQUENCE: 50

Met Ala Arg Ile Pro Thr Ala Ala Leu Gly Cys Ile Ser Leu Leu Cys
1               5                   10                  15

Leu Gln Leu Pro Gly Ser Leu Ser Arg Ser Leu Gly Gly Asp Pro Arg
            20                  25                  30

Pro Val Lys Pro Arg Glu Pro Pro Ala Arg Ser Pro Ser Ser Ser Leu
        35                  40                  45

Gln Pro Arg His Pro Ala Pro Arg Pro Val Val Trp Lys Leu His Arg
    50                  55                  60

Ala Leu Gln Ala Gln Arg Gly Ala Gly Leu Ala Pro Val Met Gly Gln
65                  70                  75                  80

Pro Leu Arg Asp Gly Gly Arg Gln His Ser Gly Pro Arg Arg His Ser
                85                  90                  95

Gly Pro Arg Arg Thr Gln Ala Gln Leu Leu Arg Val Gly Cys Val Leu
            100                 105                 110

Gly Thr Cys Gln Val Gln Asn Leu Ser His Arg Leu Trp Gln Leu Met
        115                 120                 125

Gly Pro Ala Gly Arg Gln Asp Ser Ala Pro Val Asp Pro Ser Ser Pro
    130                 135                 140

His Ser Tyr Gly
145

<210> SEQ ID NO 51
<211> LENGTH: 142
<212> TYPE: PRT
<213> ORGANISM: Homo sapiens

<400> SEQUENCE: 51

Met Ala Arg Ile Pro Thr Ala Ala Leu Gly Cys Ile Ser Leu Leu Cys
1               5                   10                  15

Leu Gln Leu Pro Gly Ser Leu Ser Arg Ser Leu Gly Gly Asp Pro Arg
            20                  25                  30

Pro Val Lys Pro Arg Glu Pro Pro Ala Arg Ser Pro Ser Ser Ser Leu
        35                  40                  45

Gln Pro Arg His Pro Ala Pro Arg Pro Val Val Trp Lys Leu His Arg
    50                  55                  60

Ala Leu Gln Ala Gln Arg Gly Ala Gly Leu Ala Pro Val Met Gly Gln
65                  70                  75                  80

Pro Leu Arg Asp Gly Gly Arg Gln His Ser Gly Pro Arg Arg Thr Gln
                85                  90                  95

Ala Gln Leu Leu Arg Val Gly Cys Val Leu Gly Thr Cys Gln Val Gln
            100                 105                 110

Asn Leu Ser His Arg Leu Trp Gln Leu Met Gly Pro Ala Gly Arg Gln
        115                 120                 125

Asp Ser Ala Pro Val Asp Pro Ser Ser Pro His Ser Tyr Gly
    130                 135                 140

<210> SEQ ID NO 52
<211> LENGTH: 23
<212> TYPE: DNA
<213> ORGANISM: Artificial Sequence
<220> FEATURE:
<223> OTHER INFORMATION: Synthetic construct

```
<400> SEQUENCE: 52
agctttgcca gctgtctcca gat                                          23

<210> SEQ ID NO 53
<211> LENGTH: 23
<212> TYPE: DNA
<213> ORGANISM: Artificial Sequence
<220> FEATURE:
<223> OTHER INFORMATION: Synthetic construct

<400> SEQUENCE: 53
ggtatccaaa gccacgagga atg                                          23

<210> SEQ ID NO 54
<211> LENGTH: 22
<212> TYPE: DNA
<213> ORGANISM: Artificial Sequence
<220> FEATURE:
<223> OTHER INFORMATION: Synthetic construct

<400> SEQUENCE: 54
ccgacctgtg gtctggaagc tt                                           22

<210> SEQ ID NO 55
<211> LENGTH: 22
<212> TYPE: DNA
<213> ORGANISM: Artificial Sequence
<220> FEATURE:
<223> OTHER INFORMATION: Synthetic construct

<400> SEQUENCE: 55
atccaggtgg agtctccatg gc                                           22

<210> SEQ ID NO 56
<211> LENGTH: 32
<212> TYPE: PRT
<213> ORGANISM: Artificial Sequence
<220> FEATURE:
<223> OTHER INFORMATION: Synthetic amino acid sequence
<220> FEATURE:
<221> NAME/KEY: MISC_FEATURE
<222> LOCATION: (1)..(1)
<223> OTHER INFORMATION: Q or absent
<220> FEATURE:
<221> NAME/KEY: MISC_FEATURE
<222> LOCATION: (2)..(2)
<223> OTHER INFORMATION: V or absent
<220> FEATURE:
<221> NAME/KEY: MISC_FEATURE
<222> LOCATION: (13)..(13)
<223> OTHER INFORMATION: M, G, P, A, or absent
<220> FEATURE:
<221> NAME/KEY: MISC_FEATURE
<222> LOCATION: (14)..(14)
<223> OTHER INFORMATION: M, G, P, A, or absent
<220> FEATURE:
<221> NAME/KEY: MISC_FEATURE
<222> LOCATION: (15)..(15)
<223> OTHER INFORMATION: M, G, P, A, or absent
<220> FEATURE:
<221> NAME/KEY: MISC_FEATURE
<222> LOCATION: (16)..(16)
<223> OTHER INFORMATION: M, G, P, A, or absent
<220> FEATURE:
<221> NAME/KEY: MISC_FEATURE
<222> LOCATION: (17)..(17)
<223> OTHER INFORMATION: M, G, P, A, or absent
<220> FEATURE:
<221> NAME/KEY: MISC_FEATURE
<222> LOCATION: (18)..(18)
<223> OTHER INFORMATION: R or absent; when absent, X at position 19 is
      absent
```

```
<220> FEATURE:
<221> NAME/KEY: MISC_FEATURE
<222> LOCATION: (19)..(19)
<223> OTHER INFORMATION: Q or absent; when absent, X at position 18 is
      absent
<220> FEATURE:
<221> NAME/KEY: MISC_FEATURE
<222> LOCATION: (20)..(20)
<223> OTHER INFORMATION: D or E
<220> FEATURE:
<221> NAME/KEY: MISC_FEATURE
<222> LOCATION: (25)..(25)
<223> OTHER INFORMATION: D or E

<400> SEQUENCE: 56

Xaa Xaa Gln Asn Leu Ser His Arg Leu Trp Gln Leu Xaa Xaa Xaa Xaa
1               5                   10                  15

Xaa Xaa Xaa Xaa Ser Ala Pro Val Xaa Pro Ser Ser Pro His Ser Tyr
            20                  25                  30

<210> SEQ ID NO 57
<211> LENGTH: 202
<212> TYPE: DNA
<213> ORGANISM: Homo sapiens

<400> SEQUENCE: 57
gacggacgcc cgtgcccagc ttgccacgcc cacgcccggc gccccgaccg cggaggactc      60
cccgagcccc gcccgccatg gcccggatcc cgacggccgc cctgggttgc atcagcctcc     120
tctgcctgca gctccctggc tcgctgtccc gcagcctggg cggggacccg cgacccgtca     180
aacccaggga gcccccagcc cg                                              202

<210> SEQ ID NO 58
<211> LENGTH: 480
<212> TYPE: DNA
<213> ORGANISM: Homo sapiens

<400> SEQUENCE: 58
attcagccct ggaggtgcca tcccgggccg cgactccgct ccaggcagga ccccccaaccc    60 gcccagcccc ctccgccttg cgccccggac ccgcggccga ccccagaccc gctgcccgct    120
tcgcgcccga ggcctgcgcc ccgacggacg cccgtgccca gcttgccacg cccacgcccg    180
gcgccccgac cgcggaggac tccccgaggt gccggcggag ggggtggctc gcggctcagg    240
ctgcccccga cgtgcccggc tcaccgcccc ctcccctgca gccccgcccg ccatggcccg    300
gatcccgacg gccgcctgg gttgcatcag cctcctctgc ctgcagctcc ctggctcgct    360
gtcccgcagc ctgggcgggg acccgcgacc cgtcaaaccc agggagcccc cagcccggag    420
cccttccagc agcctgcagc ccaggcaccc cgcaccccga cctgtggtct ggaagcttca    480
```